(12) United States Patent
Dieken et al.

(10) Patent No.: US 12,262,988 B2
(45) Date of Patent: Apr. 1, 2025

(54) RESPIRATION DETECTION

(71) Applicant: INSPIRE MEDICAL SYSTEMS, INC., Golden Valley, MN (US)

(72) Inventors: David Dieken, Minneapolis, MN (US); John Rondoni, Plymouth, MN (US); Nicholas Nesbitt, Minneapolis, MN (US); Christopher Thorp, Minneapolis, MN (US); Darrell Wagner, Ham Lake, MN (US); Kevin Verzal, Lino Lakes, MN (US)

(73) Assignee: INSPIRE MEDICAL SYSTEMS, INC., Golden Valley, MN (US)

(*) Notice: Subject to any disclaimer, the term of this patent is extended or adjusted under 35 U.S.C. 154(b) by 1008 days.

(21) Appl. No.: 16/977,664

(22) PCT Filed: Jul. 24, 2020

(86) PCT No.: PCT/US2020/043500
§ 371 (c)(1),
(2) Date: Sep. 2, 2020

(87) PCT Pub. No.: WO2021/016562
PCT Pub. Date: Jan. 28, 2021

(65) Prior Publication Data
US 2023/0119173 A1    Apr. 20, 2023

Related U.S. Application Data

(60) Provisional application No. 62/878,570, filed on Jul. 25, 2019.

(51) Int. Cl.
*A61B 5/00* (2006.01)
*A61B 5/08* (2006.01)
*A61B 5/11* (2006.01)

(52) U.S. Cl.
CPC .......... *A61B 5/0816* (2013.01); *A61B 5/1116* (2013.01); *A61B 5/1121* (2013.01)

(58) Field of Classification Search
None
See application file for complete search history.

(56) References Cited

U.S. PATENT DOCUMENTS

| 5,010,893 A | 4/1991 | Sholder |
| 5,031,618 A | 7/1991 | Mullett |
| 5,154,180 A | 10/1992 | Blanchet et al. |

(Continued)

FOREIGN PATENT DOCUMENTS

| CN | 105769122 B | 10/2018 |
| CN | 109259733 A | 1/2019 |

(Continued)

OTHER PUBLICATIONS

Redmond et al., "Cardiorespiratory-Based Sleep Staging in Subjects With Obstructive Sleep Apnea," IEEE Transactions on Biomedical Engineering, vol. 53, No. 3, Mar. 2006, pp. 1-12.

(Continued)

*Primary Examiner* — Sana Sahand
(74) *Attorney, Agent, or Firm* — DICKE, BILLIG & CZAJA, PLLC

(57) ABSTRACT

Methods and/or devices to determine patient respiration information are disclosed which comprise sensing acceleration.

15 Claims, 26 Drawing Sheets

(56) References Cited

U.S. PATENT DOCUMENTS

| | | | |
|---|---|---|---|
| 5,233,984 A | 8/1993 | Thompson | |
| 5,280,791 A | 1/1994 | Lavie | |
| 5,304,206 A | 4/1994 | Baker, Jr. et al. | |
| 5,342,409 A | 8/1994 | Mullett | |
| 5,354,317 A | 10/1994 | Alt | |
| 5,472,453 A | 12/1995 | Alt | |
| 5,483,969 A | 1/1996 | Testerman et al. | |
| 5,593,431 A | 1/1997 | Sheldon | |
| 5,722,996 A | 3/1998 | Bonnet et al. | |
| 5,732,696 A | 3/1998 | Rapoport et al. | |
| 5,902,250 A | 5/1999 | Verrier et al. | |
| 5,944,680 A | 8/1999 | Christopherson et al. | |
| 6,044,297 A * | 3/2000 | Sheldon | A61N 1/36542 |
| | | | 600/585 |
| 6,064,910 A | 5/2000 | Andersson et al. | |
| 6,161,041 A | 12/2000 | Stoop et al. | |
| 6,466,821 B1 | 10/2002 | Pianca et al. | |
| 6,641,542 B2 | 11/2003 | Cho et al. | |
| 6,658,292 B2 | 12/2003 | Kroll et al. | |
| 6,731,984 B2 | 5/2004 | Cho et al. | |
| 6,748,272 B2 | 6/2004 | Carlson et al. | |
| 6,773,404 B2 | 8/2004 | Poezevera et al. | |
| 6,964,641 B2 | 11/2005 | Cho et al. | |
| 7,025,729 B2 | 4/2006 | Chazal et al. | |
| 7,117,036 B2 | 10/2006 | Florio | |
| 7,123,954 B2 | 10/2006 | Narayan et al. | |
| 7,149,584 B1 | 12/2006 | Koh et al. | |
| 7,155,278 B2 | 12/2006 | King et al. | |
| 7,167,743 B2 | 1/2007 | Heruth et al. | |
| 7,189,204 B2 | 3/2007 | Ni et al. | |
| 7,252,640 B2 | 8/2007 | Ni et al. | |
| 7,313,440 B2 | 12/2007 | Miesel et al. | |
| 7,330,760 B2 | 2/2008 | Heruth et al. | |
| 7,340,302 B1 | 3/2008 | Falkenberg et al. | |
| 7,343,198 B2 | 3/2008 | Behbehani et al. | |
| 7,366,572 B2 | 4/2008 | Heruth et al. | |
| 7,371,220 B1 | 5/2008 | Koh et al. | |
| 7,395,113 B2 | 7/2008 | Heruth et al. | |
| 7,396,333 B2 | 7/2008 | Stahmann et al. | |
| 7,435,221 B1 | 10/2008 | Bharmi et al. | |
| 7,447,545 B2 | 11/2008 | Heruth et al. | |
| 7,473,227 B2 | 1/2009 | Hsu et al. | |
| 7,491,181 B2 | 2/2009 | Heruth et al. | |
| 7,510,531 B2 | 3/2009 | Lee et al. | |
| 7,530,956 B2 | 5/2009 | Lewicke et al. | |
| 7,542,803 B2 | 6/2009 | Heruth et al. | |
| 7,572,225 B2 | 8/2009 | Stahmann et al. | |
| 7,578,793 B2 | 8/2009 | Todros et al. | |
| 7,590,455 B2 | 9/2009 | Heruth et al. | |
| 7,660,632 B2 | 2/2010 | Kirby et al. | |
| 7,664,546 B2 | 2/2010 | Hartley et al. | |
| 7,678,058 B2 | 3/2010 | Patangay et al. | |
| 7,680,537 B2 | 3/2010 | Stahmann et al. | |
| 7,717,848 B2 | 5/2010 | Heruth et al. | |
| 7,757,690 B2 | 7/2010 | Stahmann et al. | |
| 7,766,842 B2 | 8/2010 | Ni et al. | |
| 7,775,993 B2 | 8/2010 | Heruth et al. | |
| 7,792,583 B2 | 9/2010 | Miesel et al. | |
| 7,853,322 B2 | 12/2010 | Bourget et al. | |
| 7,862,515 B2 | 1/2011 | Chazal et al. | |
| 7,873,413 B2 | 1/2011 | McCabe et al. | |
| 7,881,798 B2 | 2/2011 | Miesel et al. | |
| 7,887,493 B2 | 2/2011 | Stahmann et al. | |
| 7,896,813 B2 | 3/2011 | Sowelam et al. | |
| 7,908,013 B2 | 3/2011 | Miesel et al. | |
| 7,909,771 B2 | 3/2011 | Meyer et al. | |
| 7,957,797 B2 | 6/2011 | Bourget et al. | |
| 7,957,809 B2 | 6/2011 | Bourget et al. | |
| 7,974,689 B2 | 7/2011 | Volpe et al. | |
| 7,976,470 B2 | 7/2011 | Patangay et al. | |
| 8,002,553 B2 | 8/2011 | Hatlestad et al. | |
| 8,016,776 B2 | 9/2011 | Bourget et al. | |
| 8,021,299 B2 | 9/2011 | Miesel et al. | |
| 8,024,044 B2 | 9/2011 | Kirby et al. | |
| 8,055,348 B2 | 11/2011 | Heruth et al. | |
| 8,083,682 B2 | 12/2011 | Dalal et al. | |
| 8,150,531 B2 | 4/2012 | Skelton | |
| 8,175,720 B2 | 5/2012 | Skelton et al. | |
| 8,192,376 B2 | 6/2012 | Lovett et al. | |
| 8,209,028 B2 | 6/2012 | Skelton et al. | |
| 8,219,206 B2 | 7/2012 | Skelton et al. | |
| 8,231,555 B2 | 7/2012 | Skelton et al. | |
| 8,231,556 B2 | 7/2012 | Skelton et al. | |
| 8,265,759 B2 | 9/2012 | Tehrani et al. | |
| 8,282,580 B2 | 10/2012 | Skelton et al. | |
| 8,285,373 B2 | 10/2012 | Ternes et al. | |
| 8,323,204 B2 | 12/2012 | Stahmann et al. | |
| 8,323,218 B2 | 12/2012 | Davis et al. | |
| 8,337,431 B2 | 12/2012 | Heruth et al. | |
| 8,360,983 B2 | 1/2013 | Patangay et al. | |
| 8,366,641 B2 | 2/2013 | Wang et al. | |
| 8,475,388 B2 | 7/2013 | Ni et al. | |
| 8,535,222 B2 | 9/2013 | Ni et al. | |
| 8,548,770 B2 | 10/2013 | Yuen et al. | |
| 8,626,281 B2 | 1/2014 | Ternes et al. | |
| 8,679,030 B2 | 3/2014 | Shinar et al. | |
| 8,688,190 B2 | 4/2014 | Libbus et al. | |
| 8,696,589 B2 | 4/2014 | Kwok et al. | |
| 8,718,783 B2 | 5/2014 | Bolea et al. | |
| 8,738,126 B2 | 5/2014 | Craig | |
| 8,758,242 B2 | 6/2014 | Miesel et al. | |
| 8,801,624 B2 | 8/2014 | Patangay et al. | |
| 8,803,682 B2 | 8/2014 | Wong et al. | |
| 8,836,516 B2 | 9/2014 | Wolfe et al. | |
| 8,838,245 B2 | 9/2014 | Lin et al. | |
| 8,862,226 B2 | 10/2014 | Ternes et al. | |
| 8,870,764 B2 | 10/2014 | Rubin | |
| 8,892,205 B2 | 11/2014 | Miller, III et al. | |
| 8,905,948 B2 | 12/2014 | Davis et al. | |
| 8,909,329 B2 | 12/2014 | Prakash et al. | |
| 8,915,741 B2 | 12/2014 | Hatlestad et al. | |
| 8,934,970 B2 | 1/2015 | Ternes et al. | |
| 8,938,299 B2 | 1/2015 | Christopherson et al. | |
| 8,956,295 B2 | 2/2015 | Ni et al. | |
| 8,961,413 B2 | 2/2015 | Teller et al. | |
| 8,972,197 B2 | 3/2015 | Jangle et al. | |
| 8,992,436 B2 | 3/2015 | Pu et al. | |
| 9,026,223 B2 | 5/2015 | Skelton et al. | |
| 9,031,650 B2 | 5/2015 | McCabe et al. | |
| 9,056,195 B2 | 6/2015 | Sabesan | |
| 9,060,880 B2 | 6/2015 | Van Beest | |
| 9,159,223 B2 | 10/2015 | Proud | |
| 9,204,798 B2 | 12/2015 | Proud | |
| 9,218,574 B2 | 12/2015 | Phillipps et al. | |
| 9,302,109 B2 | 4/2016 | Sabesan | |
| 9,320,434 B2 | 4/2016 | Proud | |
| 9,320,435 B2 | 4/2016 | Proud | |
| 9,327,070 B2 | 5/2016 | Skelton et al. | |
| 9,339,188 B2 | 5/2016 | Proud | |
| 9,345,404 B2 | 5/2016 | Proud | |
| 9,380,941 B2 | 7/2016 | Proud | |
| 9,381,358 B2 | 7/2016 | Ternes et al. | |
| 9,392,939 B2 | 7/2016 | Proud | |
| 9,393,419 B2 | 7/2016 | Libbus et al. | |
| 9,398,854 B2 | 7/2016 | Proud | |
| 9,486,628 B2 | 11/2016 | Christopherson et al. | |
| 9,498,627 B2 | 11/2016 | Rosenberg et al. | |
| 9,510,775 B2 | 12/2016 | Morren et al. | |
| 9,526,422 B2 | 12/2016 | Proud | |
| 9,538,954 B2 | 1/2017 | Patangay et al. | |
| 9,545,227 B2 | 1/2017 | Selvaraj et al. | |
| 9,566,436 B2 | 2/2017 | Hoffer et al. | |
| 9,582,748 B2 | 2/2017 | Proud et al. | |
| 9,586,048 B2 | 3/2017 | Ternes et al. | |
| 9,610,030 B2 | 4/2017 | Proud | |
| 9,623,248 B2 | 4/2017 | Heruth et al. | |
| 9,655,559 B2 | 5/2017 | Chan et al. | |
| 9,656,082 B2 | 5/2017 | Denk | |
| 9,662,015 B2 | 5/2017 | Proud et al. | |
| 9,662,045 B2 | 5/2017 | Skelton et al. | |
| 9,675,268 B2 | 6/2017 | Bauer et al. | |
| 9,675,281 B2 | 6/2017 | Arnold et al. | |
| 9,675,282 B2 | 6/2017 | Morren | |
| 9,681,838 B2 | 6/2017 | Halperin et al. | |

(56) References Cited

U.S. PATENT DOCUMENTS

| | | |
|---|---|---|
| 9,687,177 B2 | 6/2017 | Ramanan et al. |
| 9,700,243 B2 | 7/2017 | Nakayama et al. |
| 9,704,209 B2 | 7/2017 | Proud et al. |
| 9,704,372 B2 | 7/2017 | Oorschot et al. |
| 9,706,957 B2 | 7/2017 | Wu et al. |
| 9,717,846 B2 | 8/2017 | Skelton et al. |
| 9,731,126 B2 | 8/2017 | Ferree et al. |
| 9,737,719 B2 | 8/2017 | Skelton et al. |
| 9,743,848 B2 | 8/2017 | Breslow et al. |
| 9,750,415 B2 | 9/2017 | Breslow et al. |
| 9,763,767 B2 | 9/2017 | Abramson et al. |
| 9,773,196 B2 | 9/2017 | Sachs et al. |
| 9,776,008 B2 | 10/2017 | Skelton et al. |
| 9,788,762 B2 | 10/2017 | Auerbach |
| 9,814,429 B2 | 11/2017 | Lee et al. |
| 9,821,165 B2 | 11/2017 | Gross |
| 9,833,171 B2 | 12/2017 | Mn et al. |
| 9,883,809 B2 | 2/2018 | Klap et al. |
| 9,889,299 B2 | 2/2018 | Ni et al. |
| 9,907,959 B2 | 3/2018 | Skelton et al. |
| 9,919,159 B2 | 3/2018 | Skelton et al. |
| 9,943,234 B2 | 4/2018 | Dalal et al. |
| 9,974,959 B2 | 5/2018 | Moffitt et al. |
| 9,987,488 B1 | 6/2018 | Gelfrand et al. |
| 9,993,179 B2 | 6/2018 | Beest et al. |
| 9,993,197 B2 | 6/2018 | Proud |
| 9,999,351 B2 | 6/2018 | Proud |
| 10,004,451 B1 | 6/2018 | Proud |
| 10,010,253 B2 | 7/2018 | Eyal et al. |
| 10,028,699 B2 | 7/2018 | Libbus et al. |
| 10,071,197 B2 | 9/2018 | Skelton et al. |
| 10,105,092 B2 | 10/2018 | Franceschetti et al. |
| 10,105,538 B2 | 10/2018 | Bolea et al. |
| 10,159,421 B2 | 12/2018 | Heneghan |
| 10,230,699 B2 | 3/2019 | Juels |
| 10,300,230 B2 | 5/2019 | Flower et al. |
| 10,328,267 B2 | 6/2019 | Hatlestad et al. |
| 10,357,163 B1 | 7/2019 | Selvaraj et al. |
| 10,471,264 B2 | 11/2019 | Bourget et al. |
| 10,531,944 B2 | 1/2020 | Lamraoui |
| 10,632,306 B2 | 4/2020 | Bolea et al. |
| 10,639,488 B2 | 5/2020 | Kalgren et al. |
| RE48,024 E | 6/2020 | Bolea et al. |
| 10,758,164 B2 | 9/2020 | Derkx |
| 10,881,331 B2 | 1/2021 | Yu et al. |
| 10,898,709 B2 | 1/2021 | Wagner et al. |
| 11,123,023 B2 | 9/2021 | Babaeizadeh |
| 11,324,950 B2 | 5/2022 | Dieken et al. |
| 11,510,611 B2 | 11/2022 | Heneghen et al. |
| 11,738,197 B2 | 8/2023 | Verzal et al. |
| 11,864,928 B2 | 1/2024 | Maile et al. |
| 11,998,303 B2 | 6/2024 | Sarkar et al. |
| 2003/0105497 A1 | 6/2003 | Zhu et al. |
| 2005/0027216 A1 | 2/2005 | Guilemaud et al. |
| 2005/0061320 A1 | 3/2005 | Lee et al. |
| 2005/0080349 A1 | 4/2005 | Okada et al. |
| 2005/0085738 A1 | 4/2005 | Stahmann et al. |
| 2005/0148897 A1 | 7/2005 | Cho et al. |
| 2005/0197588 A1 | 9/2005 | Freeberg |
| 2005/0222503 A1 | 10/2005 | Dunlop et al. |
| 2005/0288728 A1 | 12/2005 | Libbus et al. |
| 2006/0247729 A1* | 11/2006 | Tehrani ............... A61N 1/3601 607/42 |
| 2007/0032733 A1 | 2/2007 | Burton |
| 2007/0115277 A1 | 5/2007 | Wang et al. |
| 2007/0233194 A1 | 10/2007 | Craig |
| 2007/0240723 A1 | 10/2007 | Hong et al. |
| 2008/0021504 A1 | 1/2008 | McCabe et al. |
| 2008/0033304 A1 | 2/2008 | Dalal et al. |
| 2008/0051669 A1 | 2/2008 | Meyer et al. |
| 2008/0214963 A1* | 9/2008 | Guillemaud ....... A61B 5/02444 600/595 |
| 2008/0234556 A1 | 9/2008 | Brooke et al. |
| 2009/0062628 A1 | 3/2009 | Yamamoto et al. |
| 2009/0264789 A1 | 10/2009 | Molnar et al. |
| 2010/0010380 A1 | 1/2010 | Panken et al. |
| 2010/0030085 A1 | 2/2010 | Ojeda et al. |
| 2010/0094379 A1 | 4/2010 | Meadows et al. |
| 2010/0174335 A1 | 7/2010 | Stahmann et al. |
| 2010/0286545 A1 | 11/2010 | Wolfe et al. |
| 2011/0015702 A1 | 1/2011 | Ternes et al. |
| 2011/0034811 A1 | 2/2011 | Naujokat et al. |
| 2011/0046498 A1* | 2/2011 | Klap ..................... A61B 5/0205 600/534 |
| 2011/0046499 A1 | 2/2011 | Klewer et al. |
| 2011/0060215 A1* | 3/2011 | Tupin, Jr. ............. A61B 5/1075 600/407 |
| 2011/0066041 A1 | 3/2011 | Pandia et al. |
| 2011/0066064 A1 | 3/2011 | Jangle et al. |
| 2011/0172744 A1 | 7/2011 | Davis et al. |
| 2011/0172927 A1 | 7/2011 | Sahasrabudhe et al. |
| 2012/0065524 A1* | 3/2012 | Morren ................ A61B 5/1102 73/514.01 |
| 2012/0179061 A1 | 7/2012 | Ramanan et al. |
| 2012/0184825 A1 | 7/2012 | Ben David |
| 2012/0192874 A1 | 8/2012 | Bolea et al. |
| 2012/0265279 A1 | 10/2012 | Zhu |
| 2012/0290032 A1 | 11/2012 | Cho et al. |
| 2013/0172769 A1 | 4/2013 | Arvind |
| 2013/0116602 A1 | 5/2013 | Van Den Heuvel et al. |
| 2013/0165994 A1 | 6/2013 | Ternes et al. |
| 2013/0245502 A1 | 9/2013 | Lange et al. |
| 2013/0253616 A1 | 9/2013 | Libbus et al. |
| 2013/0345585 A1 | 12/2013 | Gopal Samy et al. |
| 2014/0088373 A1 | 3/2014 | Phillips et al. |
| 2014/0358825 A1 | 12/2014 | Phillipps et al. |
| 2014/0364770 A1 | 12/2014 | Slonneger et al. |
| 2014/0371817 A1 | 12/2014 | Mashiach et al. |
| 2015/0065047 A1 | 3/2015 | Wu et al. |
| 2015/0073232 A1 | 3/2015 | Ahmad et al. |
| 2015/0094962 A1 | 4/2015 | Hoegh et al. |
| 2015/0119741 A1 | 4/2015 | Zigel et al. |
| 2015/0164380 A1 | 6/2015 | O'Dwyer et al. |
| 2015/0164411 A1 | 6/2015 | Selvaraj et al. |
| 2015/0173672 A1 | 6/2015 | Goldstein et al. |
| 2015/0190089 A1 | 7/2015 | Christopherson et al. |
| 2015/0208955 A1 | 7/2015 | Smith |
| 2015/0224307 A1* | 8/2015 | Bolea ................. A61N 1/36057 607/42 |
| 2015/0238103 A1 | 8/2015 | Younes |
| 2015/0238138 A1 | 8/2015 | Lehmann et al. |
| 2015/0238304 A1 | 8/2015 | Lamraoui |
| 2015/0238766 A1 | 8/2015 | McCabe et al. |
| 2015/0273177 A1 | 10/2015 | Tizuka |
| 2015/0283381 A1 | 10/2015 | Denk |
| 2015/0283382 A1 | 10/2015 | Denk et al. |
| 2015/0374279 A1 | 12/2015 | Takakura et al. |
| 2016/0022204 A1 | 1/2016 | Mostov |
| 2016/0029969 A1 | 2/2016 | Landesberg et al. |
| 2016/0082262 A1 | 3/2016 | Parramon et al. |
| 2016/0199215 A1 | 7/2016 | Kopelman |
| 2016/0213309 A1 | 7/2016 | Sannholm et al. |
| 2016/0250490 A1 | 9/2016 | Hoffman et al. |
| 2016/0256692 A1 | 9/2016 | Baru |
| 2016/0310046 A1 | 10/2016 | Heinrich et al. |
| 2016/0338648 A1 | 11/2016 | Faisal et al. |
| 2016/0354602 A1 | 12/2016 | Keenan et al. |
| 2016/0354603 A1 | 12/2016 | Hansen et al. |
| 2016/0354608 A1 | 12/2016 | Keenan et al. |
| 2016/0379041 A1 | 12/2016 | Rhee et al. |
| 2017/0042471 A1 | 2/2017 | Meriheina |
| 2017/0046563 A1 | 2/2017 | Kim et al. |
| 2017/0056669 A1 | 3/2017 | Kane et al. |
| 2017/0071533 A1 | 3/2017 | Warren et al. |
| 2017/0076474 A1 | 3/2017 | Fu et al. |
| 2017/0087371 A1 | 3/2017 | Freeman et al. |
| 2017/0172459 A1 | 6/2017 | Bernstein et al. |
| 2017/0172494 A1 | 6/2017 | Warren et al. |
| 2017/0181691 A1 | 6/2017 | Olivier |
| 2017/0258374 A1 | 9/2017 | Ly et al. |
| 2017/0290528 A1 | 10/2017 | Ternes et al. |
| 2017/0290548 A1* | 10/2017 | Tarsaud ............... A61B 5/4818 |
| 2017/0312515 A1 | 11/2017 | Ferree et al. |
| 2017/0319109 A1 | 11/2017 | Skelton et al. |

(56) References Cited

U.S. PATENT DOCUMENTS

| | | |
|---|---|---|
| 2017/0347969 A1 | 12/2017 | Thakur et al. |
| 2017/0367646 A1 | 12/2017 | Schmidt et al. |
| 2018/0015282 A1 | 1/2018 | Waner et al. |
| 2018/0064372 A1 | 3/2018 | Beest et al. |
| 2018/0064388 A1 | 3/2018 | Heneghan et al. |
| 2018/0078174 A1 | 3/2018 | Chan et al. |
| 2018/0103895 A1 | 4/2018 | Yao |
| 2018/0153476 A1 | 6/2018 | Annoni et al. |
| 2018/0185660 A1 | 7/2018 | Eddy et al. |
| 2018/0221660 A1 | 8/2018 | Suri et al. |
| 2018/0344208 A1 | 12/2018 | Ogasawara et al. |
| 2018/0368758 A1 | 12/2018 | Winter et al. |
| 2019/0008451 A1 | 1/2019 | Horne |
| 2019/0022386 A1 | 1/2019 | Gozani et al. |
| 2019/0076098 A1 | 3/2019 | Li et al. |
| 2019/0099125 A1 | 4/2019 | Schnall |
| 2019/0133499 A1 | 5/2019 | Auerbach |
| 2019/0150772 A1 | 5/2019 | Haraikawa et al. |
| 2019/0150787 A1 | 5/2019 | Murray et al. |
| 2019/0160282 A1 | 5/2019 | Dieken et al. |
| 2019/0175026 A1 | 6/2019 | Verzal et al. |
| 2019/0223782 A1 | 7/2019 | Wen et al. |
| 2019/0231257 A1 | 8/2019 | Javed |
| 2019/0279363 A1 | 9/2019 | Steigauf et al. |
| 2019/0314192 A1 | 10/2019 | Raj et al. |
| 2020/0054289 A1 | 2/2020 | Shimol et al. |
| 2020/0107775 A1 | 4/2020 | de Chazal et al. |
| 2020/0147376 A1 | 5/2020 | Dieken et al. |
| 2020/0163794 A1 | 5/2020 | Goff et al. |
| 2020/0254249 A1 | 8/2020 | Rondoni et al. |
| 2020/0260996 A1 | 8/2020 | Yin et al. |
| 2020/0297273 A1 | 9/2020 | Gollakota et al. |
| 2020/0365271 A1 | 11/2020 | Huang et al. |
| 2020/0391028 A1 | 12/2020 | Verzal et al. |
| 2021/0030295 A1 | 2/2021 | Shute et al. |
| 2021/0038148 A1 | 2/2021 | Schmidt et al. |
| 2021/0038889 A1 | 2/2021 | Suri et al. |
| 2021/0060248 A1 | 3/2021 | Golenberg et al. |
| 2021/0169378 A1* | 6/2021 | Gerard ................ G16H 50/20 |
| 2021/0315479 A1 | 10/2021 | Stahmann |
| 2022/0000435 A1 | 1/2022 | Babaeizadeh |
| 2022/0095931 A1 | 3/2022 | Stahmann et al. |
| 2022/0095952 A1 | 3/2022 | Schipper et al. |
| 2022/0095953 A1 | 3/2022 | Wen et al. |
| 2022/0111201 A1 | 4/2022 | Verzal et al. |
| 2022/0134103 A1 | 5/2022 | Elyahoodayan et al. |
| 2022/0134104 A1 | 5/2022 | Elyahoodayan et al. |
| 2022/0183590 A1 | 6/2022 | Schipper et al. |
| 2022/0386948 A1 | 12/2022 | Javed |
| 2022/0409126 A1 | 12/2022 | Huang et al. |
| 2023/0043406 A1 | 2/2023 | Zhang et al. |
| 2023/0140863 A1 | 5/2023 | Verzal et al. |
| 2023/0270586 A1 | 8/2023 | Goff et al. |
| 2023/0310856 A1 | 10/2023 | Shelton et al. |
| 2024/0081733 A1 | 3/2024 | Gollakota et al. |

FOREIGN PATENT DOCUMENTS

| | | | |
|---|---|---|---|
| EP | 1146433 A1 | 6/1985 | |
| EP | 1938862 | 8/2004 | |
| EP | 1711104 A1 | 10/2006 | |
| EP | 1938862 A2 | 7/2008 | |
| EP | 2008581 A2 | 12/2008 | |
| EP | 2816968 B1 | 8/2018 | |
| JP | 2005066323 A | 3/2005 | |
| JP | 2006-513491 A | 4/2006 | |
| JP | 2009-532072 A | 9/2009 | |
| JP | 2012-509155 A | 4/2012 | |
| JP | 2012-533349 A | 12/2012 | |
| JP | 2014-511250 A | 5/2014 | |
| KR | 20190081320 A | 7/2019 | |
| WO | 2004064288 A2 | 7/2004 | |
| WO | 2005018737 A1 | 3/2005 | |
| WO | 2012154733 A1 | 11/2012 | |
| WO | 2016016469 A1 | 2/2016 | |
| WO | 2016093927 A1 | 6/2016 | |
| WO | 2016195809 A1 | 12/2016 | |
| WO | 2017087681 A1 | 5/2017 | |
| WO | 2017093054 A1 | 6/2017 | |
| WO | 2017098609 A1 | 6/2017 | |
| WO | 2017117335 A1 | 7/2017 | |
| WO | 2017117636 A1 | 7/2017 | |
| WO | 2017136352 A1 | 8/2017 | |
| WO | 2017183039 A1 | 10/2017 | |
| WO | 2017183602 A1 | 10/2017 | |
| WO | 2017184753 A1 | 10/2017 | |
| WO | 2017198787 A1 | 11/2017 | |
| WO | 2017201419 A1 | 11/2017 | |
| WO | 2017210055 A1 | 12/2017 | |
| WO | 2017211396 A1 | 12/2017 | |
| WO | 2017223404 A1 | 12/2017 | |
| WO | 2018006121 A1 | 1/2018 | |
| WO | 2018016392 A1 | 1/2018 | |
| WO | 2018068084 A1 | 4/2018 | |
| WO | 2018081778 A1 | 5/2018 | |
| WO | WO-2019106351 A1 * | 6/2019 | ......... A61B 5/02416 |
| WO | 2020045710 A1 | 3/2020 | |
| WO | 2020132315 A1 | 6/2020 | |
| WO | 2020169424 A1 | 8/2020 | |
| WO | 2022247649 A1 | 12/2022 | |

OTHER PUBLICATIONS

Stein et al., "Heart rate variability, sleep and sleep disorders," Sleep Medicine Reviews, vol. 16, Issue 1, Feb. 2012, pp. 47-66.

PCT International Search Report and Written Opinion, Int'l Appl. No. PCT/US82020/043405, mailed Nov. 5, 2020, pp. 1-10.

PCT International Search Report and Written Opinion, Int'l Appl. No. PCT/US2020/043493, mailed Oct. 22, 2020, pp. 1-13.

Girardin et al., "Sleep detection with an accelerometer actigraph: comparisons with polysomnography," Physiology & Behavior, vol. 72, Issue 1-2, Jan.-Feb. 2001, pp. 21-28.

PCT International Search Report and Written Opinion, Int'l Appl. No. PCT/US2020/043500, mailed Oct. 26, 2020, pp. 1-14.

Invitation to Pay Additional Fees and, Where Applicable, Protest Fee (includes preliminary International Search Report), Int'l Appl. No. PCT/US2020/043442, mailed Oct. 22, 2020, pp. 1-14.

"AASM clarifies hypopnea scoring criteria," American Academy of Sleep Medicine, Sep. 23, 2013, aasm.org/aasm-clarifies-hypopnea-scoring-criteria/.

Epstein et al., "Clinical Guideline for the Evaluation, Management and Long-term Care of Obstructive Sleep Apnea in Adults," Journal of Clinical Sleep Medicine, vol. 5, No. 3, 2009, pp. 263-276.

Immanuel et al., "Respiratory timing and variability during sleep in children with sleep-disordered breathing," J Appl Physiol 113, Sep. 27, 2012, pp. 1635-1642.

Morgenthaler et al., "Practice Parameters for the Medical Therapy of Obstructive Sleep Apnea," Sleep, vol. 29, No. 8, 2006, pp. 1031-1035.

Phurrough et al., "Decision Memo for Continuous Positive Airway Pressure (CPAP) Therapy for Obstructive Sleep Apnea (OSA) (CAG-00093R2)," U.S. Centers for Medicare & Medicaid Services, Mar. 13, 2008, www.cms.gov/medicare-coverage-database/details/nca-decision-memo.aspx?NCA.

Rodriguez, Julia, "What do AHI, RERA, Arousal and RDI mean?," The Sleep Blog, Advanced Sleep Medicine Services, Inc., www.sleepdr.com/the-sleep-blog/what-do-ahi-rera-arousal-and-rdi-mean/ ResMed 2019.

Winnebeck et al., "Dynamics and Ultradian Structure of Human Sleep in Real Life," Current Biology, vol. 28, Jan. 8, 2018, pp. 49-59.

Schwartz et al., Therapeutic Electrical Stimulation of the Hypoglossal Nerve in Obstructive Sleep Apnea, Arch Otolaryngol Head Neck Surg, vol. 127, Oct. 2001, pp. 1216-1223.

Goldstein et al., "Artificial intelligence in sleep medicine: background and implications for clinicians", J Clin Sleep Med., vol. 16, Issue 4, Apr. 15, 2020, pp. 609-618.

Schmickl et al., "The Respiratory Signature: A Novel Concept to Leverage Continuous Positive Airway Pressure Therapy as an Early

(56) References Cited

OTHER PUBLICATIONS

Warning System for Exacerbations of Common Diseases such as Heart Failure", J Clin Sleep Med., vol. 15, Issue 6, Jun. 15, 2019, pp. 923-927.
PCT International Search Report and Written Opinion, Int'l Appl. No. PCT/US2020/043442, mailed Dec. 14, 2020, pp. 1-15.

* cited by examiner

800

ARRANGING THE ACCELERATION SENSOR AS N NUMBER OF ORTHOGONALLY-ARRANGED SINGLE AXIS ACCELERATION SENSING ELEMENTS

IDENTIFYING, VIA THE SENSING, WHICH OF THE N SINGLE AXIS ACCELERATION SENSING ELEMENTS EXHIBITS A REFERENCE ANGULAR ORIENTATION, DURING BREATHING, CLOSEST TO BEING GENERALLY PERPENDICULAR TO AN EARTH GRAVITY VECTOR

DETERMINING THE REFERENCE ANGULAR ORIENTATION OF EACH N AXIS ACCELERATION SENSING ELEMENTS AS AN INCLINATION ANGLE OF A MEASUREMENT AXIS OF EACH RESPECTIVE N AXIS ACCELERATION SENSING ELEMENTS RELATIVE TO THE GRAVITY VECTOR

IMPLEMENTING THE SENSING VIA SENSING AN AC SIGNAL COMPONENT OF THE RESPECTIVE ACCELERATION SENSING ELEMENTS WHILE EXCLUDING A DC SIGNAL COMPONENT OF THE RESPECTIVE ACCELERATION SENSING ELEMENTS

PERFORMING THE DETERMINATION OF RESPIRATION INFORMATION, VIA THE SENSED ROTATIONAL MOVEMENT, USING THE IDENTIFIED SENSING ELEMENT

SENSING AN AC SIGNAL COMPONENT OF THE IDENTIFIED SENSING ELEMENT WITHIN A RANGE OF ANGULAR ORIENTATIONS OF THE IDENTIFIED SENSING ELEMENT, WHEREIN A FIRST END OF THE RANGE OF ORIENTATIONS CORRESPONDS TO A PEAK EXPIRATION AND AN OPPOSITE SECOND END OF THE RANGE OF ORIENTATIONS CORRESPONDS TO A PEAK INSPIRATION

(1) IDENTIFYING WHICH OF THE N SINGLE AXIS ACCELERATION SENSING ELEMENTS EXHIBITS A REFERENCE ANGULAR ORIENTATION, DURING BREATHING, WITHIN A RANGE OF ABOUT 45 DEGREES TO ABOUT 135 DEGREES RELATIVE TO THE GRAVITY VECTOR; (2) SENSING, FOR EACH RESPECTIVE SENSING ELEMENT, A RANGE OF ANGULAR ORIENTATIONS WHEREIN A FIRST END OF THE RANGE CORRESPONDS TO PEAK EXPIRATION AND AN OPPOSITE SECOND END OF THE RANGE CORRESPONDS TO PEAK INSPIRATION; AND (3) DETERMINING WHICH OF THE RESPECTIVE SENSING ELEMENTS EXHIBITS A GREATEST RANGE OF ANGULAR ORIENTATIONS

PERFORMINING THE DETERMINATION OF RESPIRATION INFORMATION, VIA THE SENSED ROTATIONAL MOVEMENT, USING THE IDENTIFIED SENSING ELEMENT DETERMINED TO EXHIBIT THE GREATEST RANGE OF ANGULAR ORIENTATIONS

IDENTIFYING WHICH OF THE N SINGLE AXIS ACCELERATION SENSING ELEMENTS, DURING BREATHING, EXHIBITS A GREATEST RANGE OF VALUES OF AN AC SIGNAL COMPONENT

PERFORMINING THE DETERMINATION OF RESPIRATION INFORMATION, VIA THE SENSED ROTATIONAL MOVEMENT, USING THE IDENTIFIED SENSING ELEMENT DETERMINED TO EXHIBIT THE GREATEST RANGE OF VALUES OF THE AC SIGNAL COMPONENT

SENSING AN AC SIGNAL COMPONENT OF THE IDENTIFIED SENSING ELEMENT, DURING BREATHING, WHEREIN A FIRST END OF A RANGE OF VALUES OF THE SENSED AC SIGNAL COMPONENT CORRESPONDS TO A PEAK EXPIRATION AND AN OPPOSITE SECOND END OF THE RANGE OF VALUES OF THE AC SIGNAL COMPONENT CORRESPONDS TO A PEAK INSPIRATION

FIG. 10L

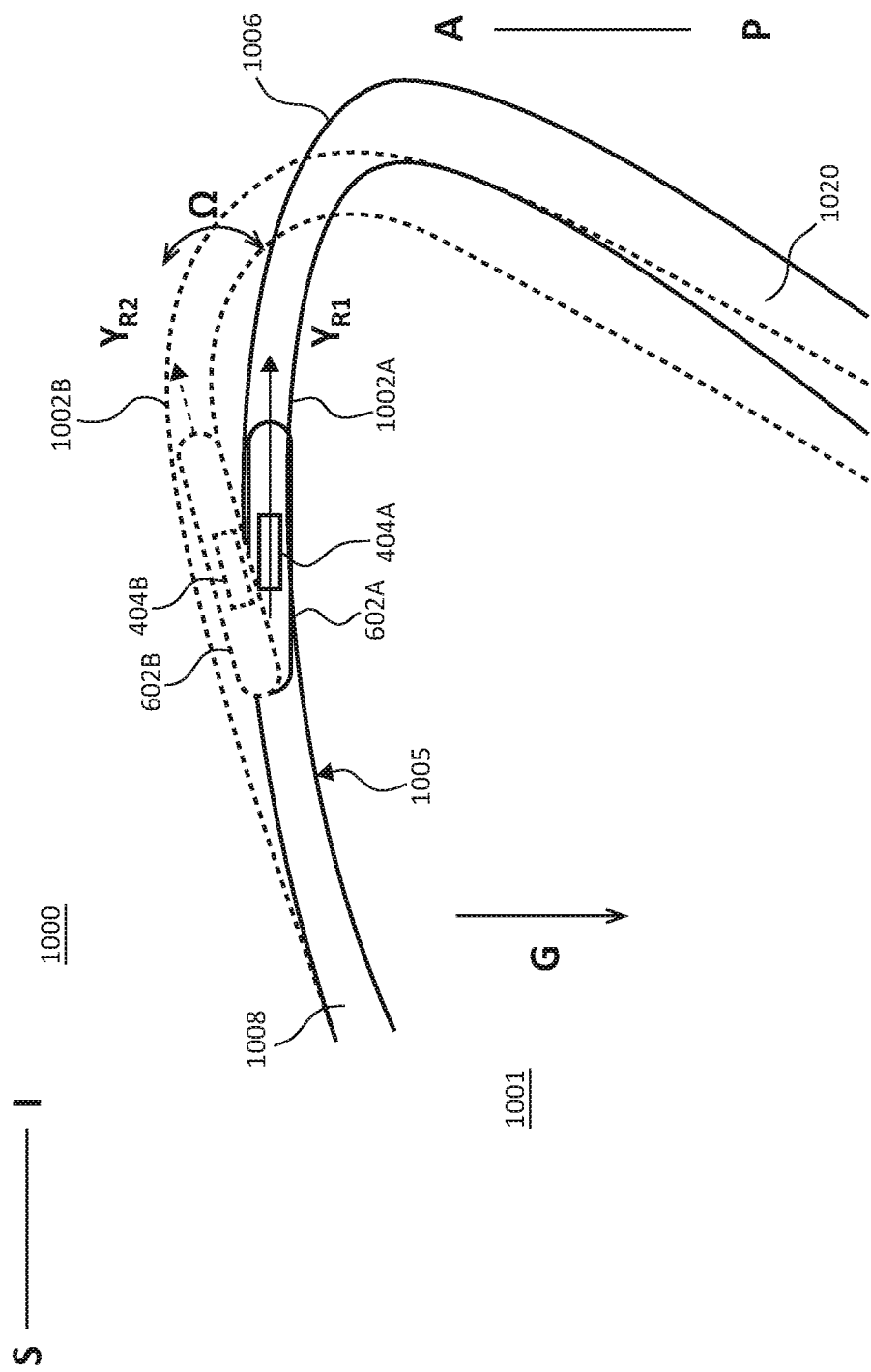

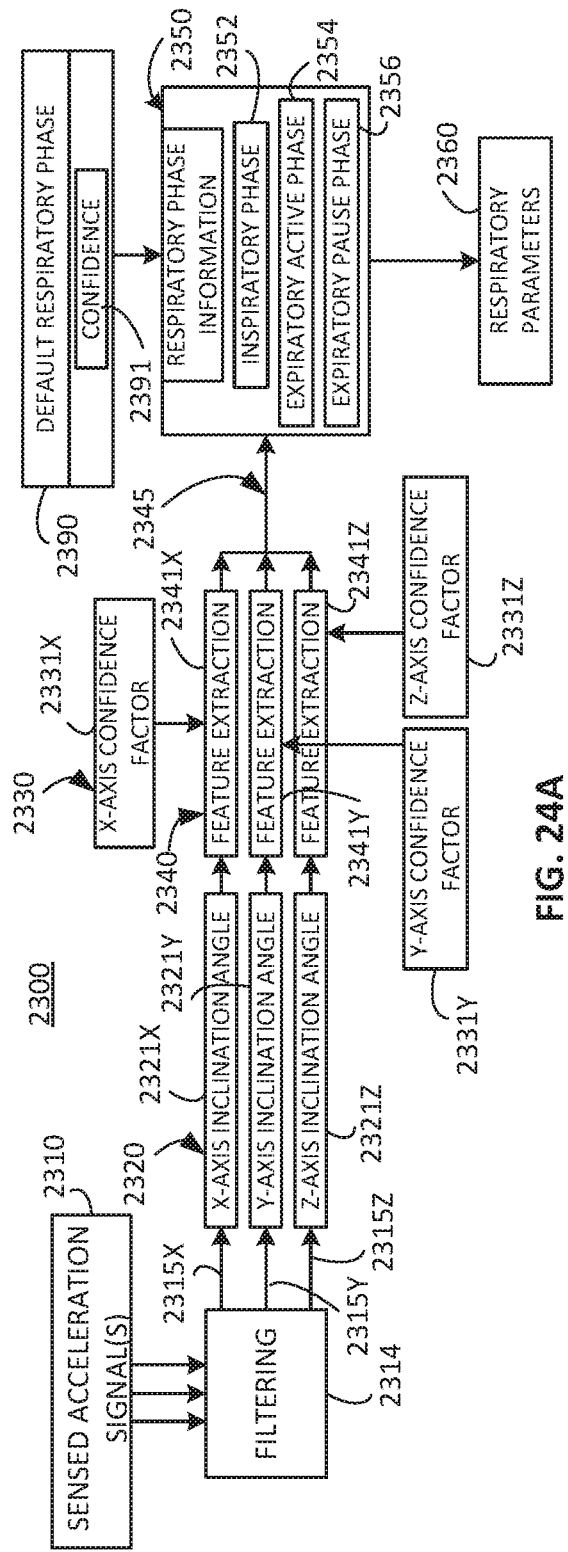
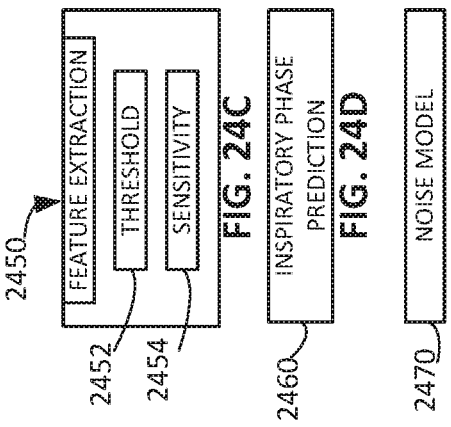
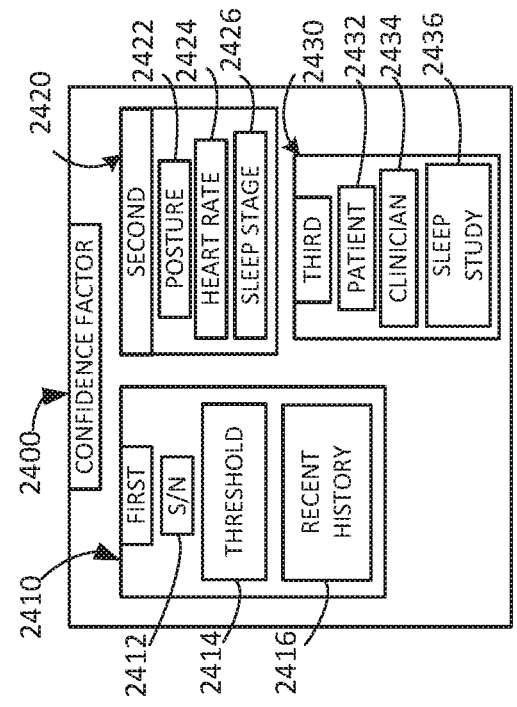
FIG. 24A
FIG. 24B
FIG. 24C
FIG. 24D
FIG. 24E

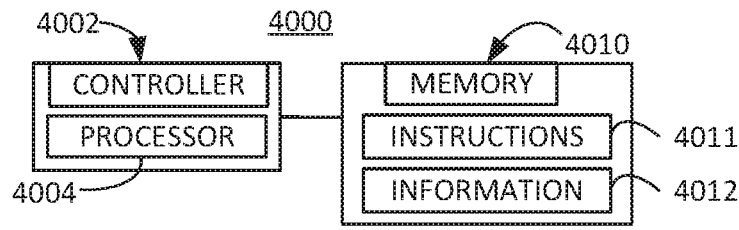
FIG. 25A
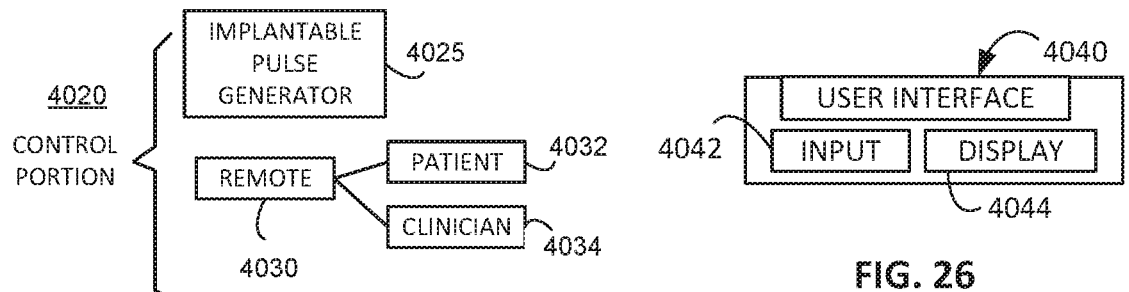
FIG. 25B
FIG. 26
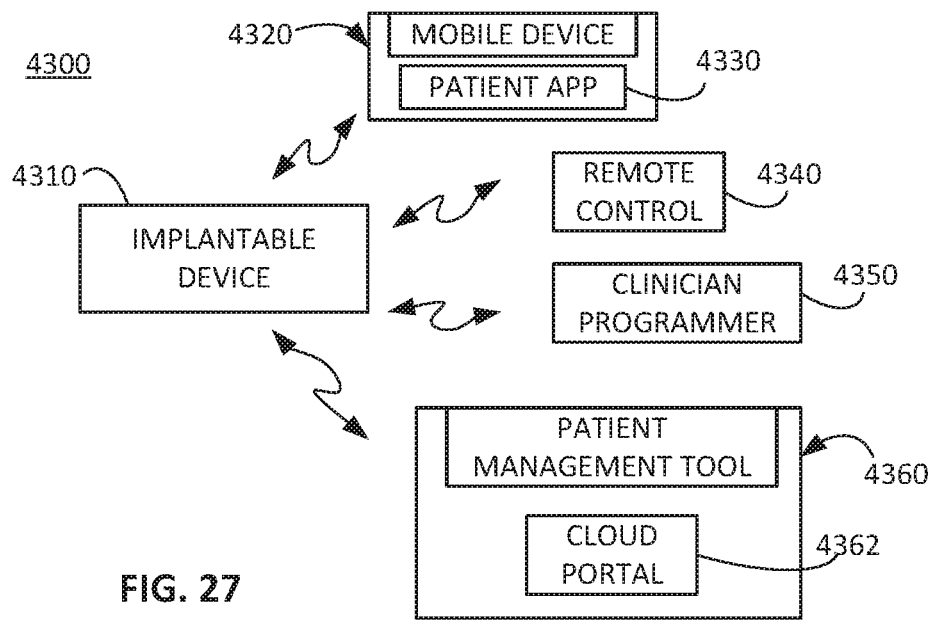
FIG. 27

5000

IMPLANTABLY SECURING AN ACCELERATION SENSOR AT A FIRST PORTION OF A RESPIRATORY BODY PORTION OF A PATIENT; AND

DETERMINING RESPIRATION INFORMATION VIA SENSING, VIA THE ACCELERATION SENSOR, ROTATIONAL MOVEMENT AT THE FIRST PORTION OF THE RESPIRATORY BODY PORTION CAUSED BY BREATHING

IMPLANTABLY SECURING AN ACCELERATION SENSOR AT A FIRST PORTION OF A CHEST WALL OF A PATIENT; AND

DETERMINING RESPIRATION INFORMATION VIA SENSING, VIA THE ACCELERATION SENSOR, ROTATIONAL MOVEMENT AT THE FIRST PORTION OF THE CHEST WALL CAUSED BY BREATHING

SENSING THE ROTATIONAL MOVEMENT RELATIVE TO AN EARTH GRAVITY VECTOR

SENSING THE ROTATIONAL MOVEMENT ACCORDING TO AT LEAST ONE OF THREE INDEPENDENT ORTHOGONAL AXES

COMBINING SENSED ROTATIONAL MOVEMENT INFORMATION FROM AT LEAST TWO OF THE THREE INDEPENDENT ORTHOGONAL AXES

TRACKING CHANGES IN A VALUE OF A FIRST SIGNAL, FOR A FIRST BODY POSITION DURING A TREATMENT PERIOD, OF AT LEAST ONE MEASUREMENT AXIS DURING AT LEAST ONE RESPIRATORY PERIOD

DETERMINING RESPIRATION INFORMATION WITHOUT SEPARATELY IDENTIFYING MEASUREMENT INFORMATION FROM THE SENSOR REGARDING TRANSLATIONAL MOTION OF THE CHEST WALL CAUSED BY BREATHING

SENSING THE ROTATATIONAL MOVEMENT WITHOUT CALIBRATING THE MEASURED INCLINATION ANGLE SIGNAL REGARDING DIFFERENCES BETWEEN AN IDEAL REFERENCE ORIENTATION AND AN ACTUAL IMPLANT ORIENTATION

IDENTIFYING THE ROTATIONAL CHANGES AS AT LEAST ONE OF A PITCH PARAMETER, YAW PARAMETER, AND A ROLL PARAMETER

SELECTING AN IMPLANT LOCATION TO MAXIMIZE A MAGNITUDE OF THE SENSED ROTATIONAL MOVEMENT DURING BREATHING

DETERMINING RESPIRATION INFORMATION, VIA THE SENSED ROTATIONAL MOVEMENT, WHILE EXCLUDING AT LEAST ONE OF CARDIAC INFORMATION, MUSCLE INFORMATION, AND MEASUREMENT/NOISE INFORMATION

INCREASING A SIGNAL-TO-NOISE RATIO OF SENSED RESPIRATORY INFORMATION VIA SUBTRACTING NOISE, ACCORDING TO A NOISE MODEL, FROM THE SENSED ACCELERATION SIGNAL(S)

MEASURING THE AT LEAST ONE ACCELERATION SIGNAL AS MEASURING AN INCLINATION ANGLE OF A FIRST MEASUREMENT AXIS ALIGNED GENERALLY PERPENDICULAR TO AN EARTH GRAVITY VECTOR

PERFORMING THE ACCELERATION SENSING OF ROTATIONAL MOVEMENT WITHOUT DETERMINING A BODY POSITION OCCURING DURING THE SENSING OF ROTATIONAL MOVEMENT

PERFORMING THE SENSING OF ROTATIONAL MOVEMENT, DURING EACH OF SEVERAL DIFFERENT SLEEPING BODY POSITIONS, WITHOUT DETERMINING EACH DIFFERENT SLEEPING BODY POSITION AT THE TIME OF THE SENSING

DETERMINING RESPIRATORY MORPHOLOGY, INCLUDING RESPIRATORY PHASE INFORMATION, BASED ON A PROFILE OVER TIME OF THE RESPECTIVE DETERMINED RANGE OF VALUES

DETERMINING, FROM THE SENSED ROTATIONAL MOVEMENT, RESPIRATORY MORPHOLOGY COMPRISING AN EXPIRATORY ACTIVE PHASE, AN EXPIRATORY PAUSE PHASE, AND INSPIRATORY PHASE

IDENTIFYING A CONFIDENCE LEVEL OF THE DETERMINED EXPIRATORY ACTIVE PHASE, EXPIRATORY PAUSE PHASE, AND INSPIRATORY PHASE

FURTHER DETERMINING THE CONFIDENCE FACTOR BASED ON ADDITIONAL CRITERIA COMPRISING POSTURE INFORMATION, HEART RATE INFORMATION, AND/OR SLEEP STATE INFORMATION

IMPLEMENTING EXTRACTION OF THE RESPECTIVE INSPIRATORY PHASE, EXPIRATORY PHASE, AND EXPIRATORY PAUSE VIA APPLYING A SELECTABLE INSPIRATORY THRESHOLD, SELECTABLE EXPIRATORY PHASE THRESHOLD, AND/OR SELECTABLE EXPIRATORY PAUSE THRESHOLD

ARRANGING THE ACCELERATION SENSOR TO INCLUDE AT LEAST TWO ORTHOGONAL AXES, EACH OF WHICH PRODUCES AT LEAST A PORTION OF THE RESPIRATION INFORMATION DEPENDING ON A FIRST BODY POSITION OF THE PATIENT

FIG. 46

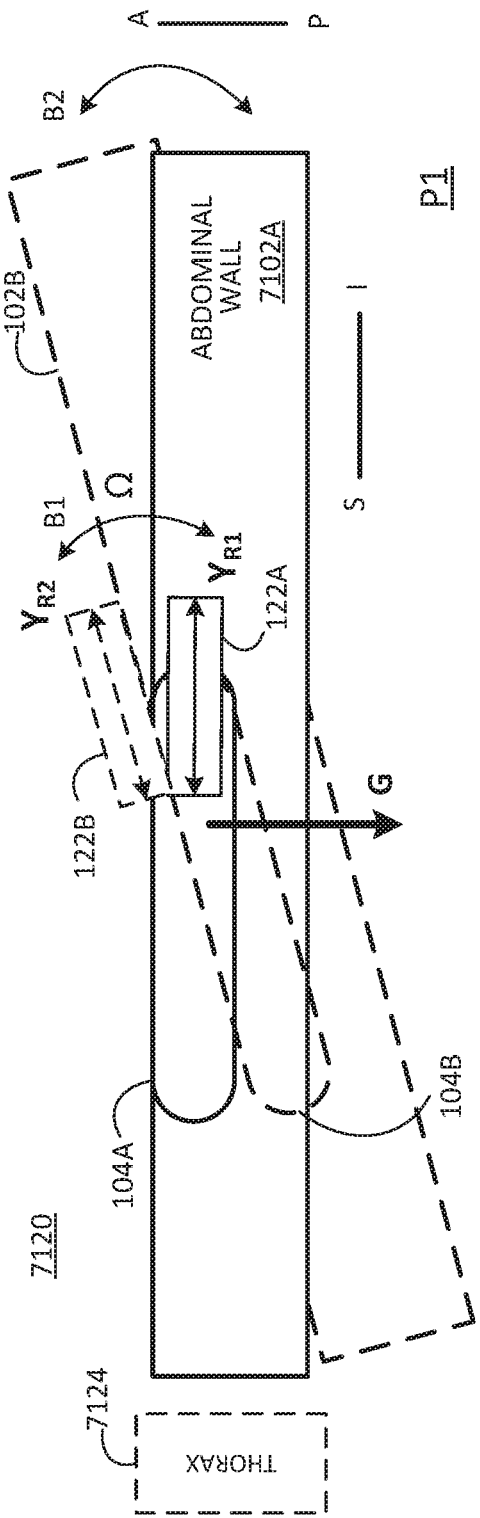

RESPIRATION DETECTION

CROSS REFERENCE TO RELATED APPLICATION

This Utility Patent Application claims priority under 35 U.S.C. § 371 to International Application Serial No. PCT/US20/43500, filed Jul. 24, 2020, which claims the benefit of U.S. Provisional Patent Application Ser. No. 62/878,570, filed Jul. 25, 2019, all of which are incorporated herein by reference.

BACKGROUND

A significant portion of the population suffers from various forms of sleep disordered breathing (SDB). In some patients, external breathing therapy devices and/or mere surgical interventions may fail to treat the sleep disordered breathing behavior.

BRIEF DESCRIPTION OF THE DRAWINGS

FIG. 10B is a diagram schematically representing an example method of arranging an acceleration sensor.

FIG. 10C is a diagram schematically representing an example method of identifying a sensing element in relation to a reference angular orientation.

FIG. 10D is a diagram schematically representing an example method of determining a reference angular orientation.

FIG. 10E is a diagram schematically representing an example method of implementing sensing.

FIG. 10F is a diagram schematically representing an example method of determining respiration information via an identified sensing element.

FIG. 10G is a diagram schematically representing an example method of sensing within a range of angular orientations.

FIG. 10H is a diagram schematically representing an example method of identifying which sensing element exhibits a reference angular orientation.

FIG. 10I is a diagram schematically representing an example method of determining respiration information using an identified sensing element in relation to a greatest range of angular orientations.

FIG. 10J is a diagram schematically representing an example method of identifying a sensing element in relation to a greatest range of values of an AC signal component.

FIG. 10K is a diagram schematically representing an example method of determining respiration information using an identified sensing element in relation to a greatest range of values of an AC signal component.

FIG. 10L is a diagram schematically representing an example method of sensing an AC signal component during breathing.

FIG. 11 is a diagram including a side view of a patient's chest and which schematically represents an example method of determining respiration information based on sensing rotational movement of the chest during breathing.

FIG. 24A is a block diagram schematically representing an example method and/or example device for determining respiration information via a sensed acceleration signal.

FIG. 24B is a block diagram schematically representing an example confidence factor portion.

FIG. 24C is a block diagram schematically representing an example feature extraction portion.

FIG. 24D is a block diagram schematically representing an example inspiratory phase prediction function.

FIG. 24E is a block diagram schematically representing an example noise model parameter.

FIGS. 25A and 25B each are a block diagram schematically representing an example control portion.

FIG. 26 is a block diagram schematically representing an example user interface.

FIG. 27 is a block diagram schematically representing an example communication arrangement between an implantable device and different devices external to the patient.

FIG. 28A is a block diagram schematically representing an example method of determining respiration information in relation to sensing rotation of a respiratory body portion.

FIG. 28B is a block diagram schematically representing an example method of determining respiration information in relation to sensing rotation of a chest wall of patient.

FIG. 29 is a block diagram schematically representing an example method of sensing rotation in relation to an earth gravity vector.

FIGS. 30 and 31 each are a block diagram schematically representing an example method of sensing rotational movement in relation particular orthogonal axes.

FIG. 32 is a block diagram schematically representing an example method of determining respiration information for a first body position.

FIG. 33 is a block diagram schematically representing an example method of determining respiration information without separately identifying translation motion.

FIG. 34 is a block diagram schematically representing an example method of determining respiration information without implant orientation calibration.

FIG. 35 is a block diagram schematically representing an example method of determining respiration information in relation to pitch, yaw, and roll.

FIG. 36 is a block diagram schematically representing an example method of selecting an implant location.

FIG. 37A is a block diagram schematically representing an example method of determining respiration information while excluding information regarding cardiac, muscle, and/or noise.

FIG. 37B is a block diagram schematically representing an example method of determining respiration information via subtracting noise.

FIG. 38 is a block diagram schematically representing an example method of determining respiration information via measuring inclination relative to an earth gravity vector.

FIG. 39 is a block diagram schematically representing an example method of determining respiration information without determining body position.

FIG. 40 is a block diagram schematically representing an example method of determining respiration information while the patient is in different body positions.

FIGS. 41 and 42 each are a block diagram schematically representing an example method of determining respiratory morphology.

FIGS. 43 and 44 each are a block diagram schematically representing an example method of determining respiration information in relation to a confidence information.

FIG. 45 each are a block diagram schematically representing an example method of extracting respiratory phase information in relation to thresholds.

FIG. 46 is a block diagram schematically representing an example method of determining respiration information in relation to body position.

FIG. 47 is a block diagram schematically representing an example method of determining respiration information based on sensing rotational movement of an abdomen.

FIG. 48 is a diagram, including a side view, schematically representing an example method and/or example device for detecting respiration via an acceleration sensor at an abdominal wall.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to detecting respiration information. In some such examples, the detection of respiration may based, at least in part, on sensing rotational movement at a respiratory body portion caused by breathing. In some examples, the respiratory body portion may comprise a chest (e.g. chest wall), abdomen (e.g. abdominal wall), and/or other body portion exhibiting rotational movement indicative of respiration.

Figure 1:
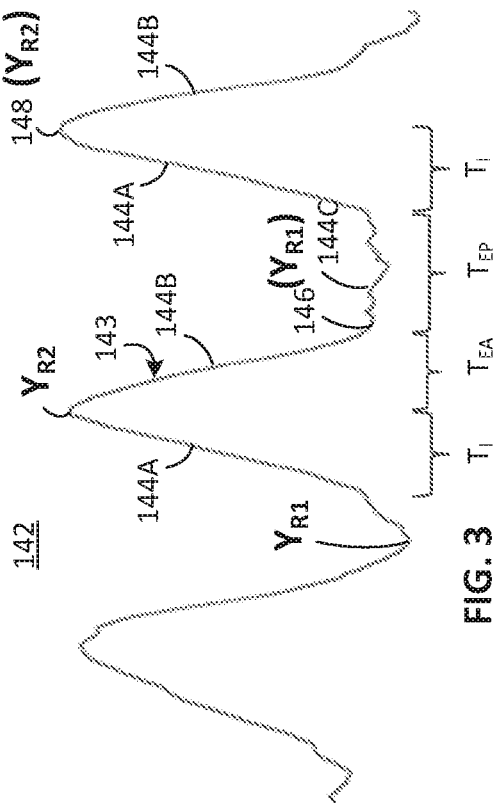
FIG. 1 is a diagram including a side view, schematically representing an example method and/or example device for detecting respiration via an acceleration sensor.
Figure 52:
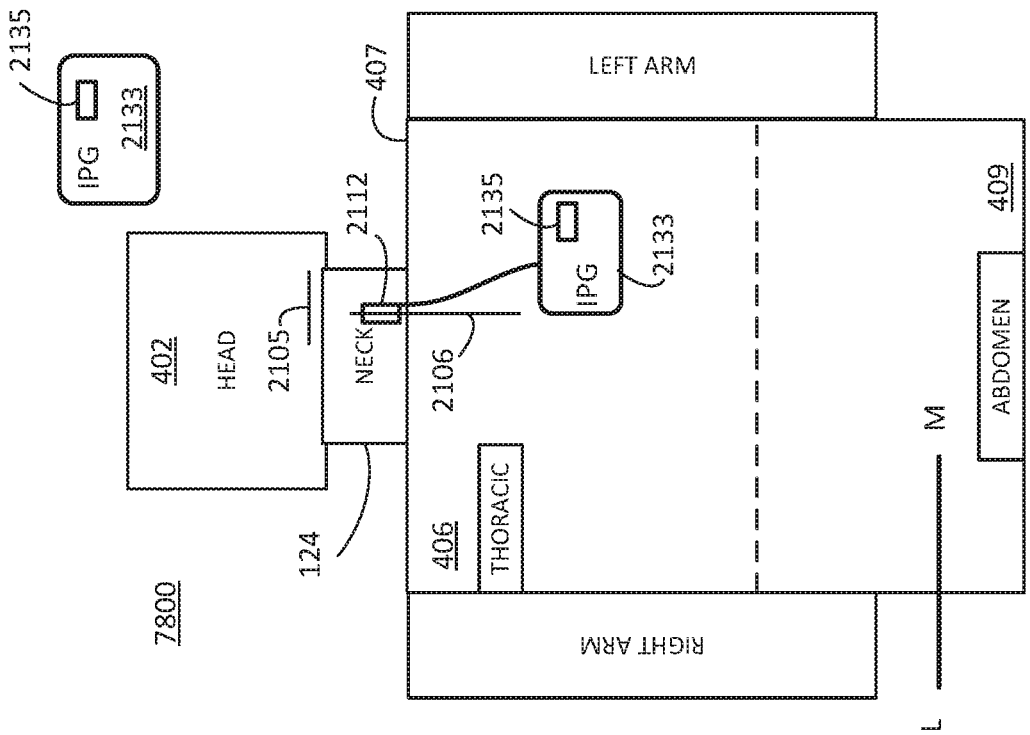
FIG. 52 is a diagram, including a front view, schematically representing an example method and/or example device for treating sleep disordered breathing via a medical device, including an acceleration sensor, implanted in a pectoral region to stimulate a phrenic nerve in the head-and-neck region.

At least these examples, and additional examples, are described in association with at least FIGS. 1-52.

FIG. 1 is a diagram including a side view, schematically representing an example method 100 and/or example device including a sensor 104A. As shown in FIG. 1, example sensor 104A is chronically, subcutaneously implanted within a chest wall 102A of a patient's body. During breathing, the chest wall 102A will exhibit rotational movement (B2) as at least some portions of the chest wall 102A move (e.g. rise and fall) during inhalation and expiration, wherein inspiration corresponds to expansion of the rib cage and expiration corresponds to contraction of the rib cage. During this expansion and contraction of the rib cage during breathing, at least some portions of the chest wall 102A exhibit rotational behavior, which may in turn may be sensed upon the sensor 104A experiencing such rotational movement (as represented via directional arrow B1), which in turn provides respiration information as further described below. It will be understood, as further described later, that the rotational movement of the sensed portion of the chest wall 102A is not necessarily or strictly limited to rotational movement in a single plane.

In some examples, sensor 104A may comprise a portion of a larger device, as further described later in association with at least FIGS. 23A-23B.

As further shown in FIG. 1, the sensor 104A may sense the rotational movement of at least a portion of the chest wall 102 (as represented via directional arrow B2) relative to an earth gravitational field (arrow G), i.e. gravity vector. For illustrative simplicity to depict at least some examples, FIG. 1 depicts the chest wall 102A as if the patient's body was in a generally horizontal sleep position. It will be understood that at least some example devices and/or example methods will be effective in detecting respiration information regardless of whether the generally horizontal sleep position is a supine position, a prone position, or a side-laying (i.e. lateral decubitus) position. Moreover, at least some example methods and/or example devices also will be effective in detecting respiration information if, and when, the patient is in positions other than a generally horizontal position, such as sitting in a chair in a vertically upright position, in a reclining position, etc. as further described later in association with at least FIGS. 6A-7.

Moreover, as described later in association with at least FIG. 39, determining respiration information via acceleration-based sensing of rotational movements (at a portion of a chest wall of the patient) does not include, or depend on, determining (e.g. via sensing) a body position of the patient. Accordingly, while such respiration information may be determined in any one of several different sleeping body positions, such determination may be performed without determining the particular sleeping body position at the time the sensing of the rotational movements is being performed.

However, in some such examples, the particular sleeping body position occurring at the time of the determining the respiration information (via acceleration-based sensing of rotational movements of a portion of a chest wall during breathing) may be determined and used as a parameter to augment the determined respiration information and/or other general patient physiologic information, in some instances.

In some examples, securing the implantable acceleration sensor(s) comprises mechanically coupling the sensor(s) relative to a respiratory body portion. In some examples, securing the implanted acceleration sensor(s) comprises securing the acceleration sensor relative to tissue on top of a muscle layer of the respiratory body portion, while in some examples the sensor may be secured directly to a muscle layer of the respiratory body portion. In some examples, the acceleration sensor may be secured subcutaneously within the respiratory body portion without securing the acceleration sensor on the muscle layers. In some examples, the respiratory body portion may comprise the chest. In some such examples, the respiratory body portion may comprise a portion of the chest, such as but not limited to a portion of a chest wall. In some instances, the portion of the chest wall may correspond to a portion of the rib cage. In some examples, such aspects of securing the sensor(s) relative to a muscle layer or subcutaneously are also applicable to securing the sensor at other respiratory body portions, such as an abdomen (e.g. abdominal wall) physically (e.g. mechanically) couple the sensor relative to the abdomen to sense rotational movement at the abdomen during breathing, as more fully described later in association with at least FIGS. 47-52.

Figure 2:
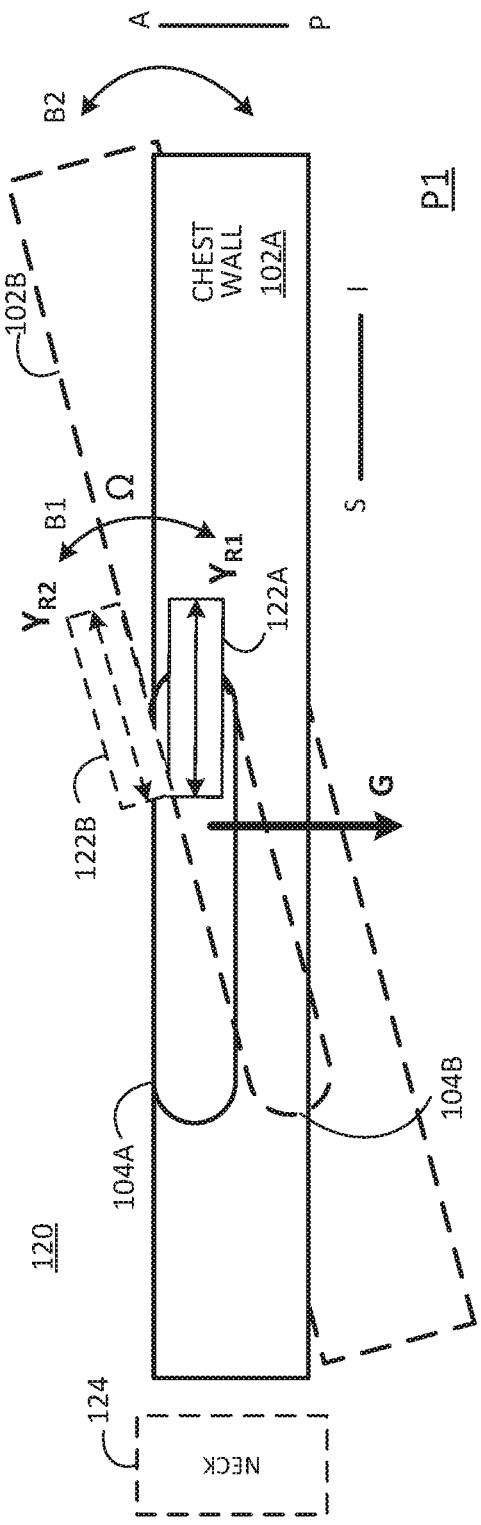
FIG. 2 is a diagram, including a side view, schematically representing an example method and/or example device for detecting respiration via an acceleration sensor at a chest wall.

FIG. 2 is a diagram 120, including a side view, schematically representing an example method and/or example sensor 104A. As shown in FIG. 2, in some examples the sensor 104A may comprise a sensing element 122A, which is arranged to measure an inclination angle ($\Omega$) upon rotational movement of the sensing element 122A caused by breathing. As represented in FIG. 2, upon rotational movement of at least a portion of the chest wall 102A during breathing, the sensing element 122A may rotationally move between a first angular orientation YR1 (shown in solid lines) and a second angular orientation YR2 (shown in dashed lines). In some such examples, the first angular orientation YR1 (shown in solid lines) of sensing element 122A may correspond to a peak expiration of a respiratory cycle (e.g. rib cage contracted) and the second angular orientation YR2 (shown in dashed lines) of sensing element 122A may correspond to a peak inspiration of the respiratory cycle (e.g. rib cage expanded).

With reference to at least FIG. 2, it will understood that the sensing element 122A moves with at least a portion of the chest wall 102A as depicted in dashed lines. Accordingly, sensing element 122A does not move relative to the chest wall 102A, but rather the sensing element 122A rotationally moves along with (e.g. in synchrony with) the rotational movement of at least the portion of the chest wall 102A (in which the sensor 104A, including sensing element 122A), is implanted) during breathing.

In some examples, the sensing element 122A comprises an accelerometer, which may comprise a single axis accelerometer in some examples or which may comprise a multiple-axis accelerometer in some examples. Via the accelerometer, the sensing element 122A can determine absolute rotation of sensor 104A (and therefore rotation of the portion of the chest wall 102A) with respect to gravity (e.g. earth gravity vector G), rather than instantaneous changes in rotation.

In some examples, element 122A may comprise a single axis accelerometer to measure (at least) a value of, and changes in the value of, the above-noted inclination angle ($\Omega$) associated with movement of at least a portion the chest wall 102 caused by breathing.

In some examples, sensing element 122A may comprise an accelerometer and a gyroscope.

Figure 3:
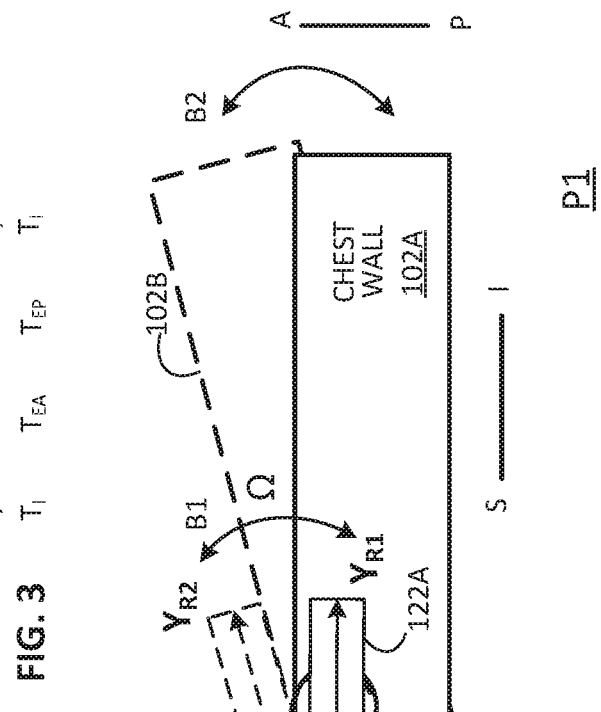
FIG. 3 is a diagram including a graph schematically representing an example filtered, sensed acceleration signal.

FIG. 3 is a diagram including a graph 140 schematically representing a filtered acceleration signal 142 sensed via a sensor, such as sensing element 122A in FIG. 2. As shown in FIG. 3, signal 142 corresponds to a respiratory waveform exhibited through several respiratory cycles during breathing. Each respiratory cycle 143 comprises an inspiratory phase ($T_I$), an expiratory active phase ($T_{EA}$), and an expiratory pause phase ($T_{EP}$). It will be understood that the example respiratory waveform in FIG. 3 represents a typical respiratory waveform for at least some patients during normal breathing, but not necessarily for all patients at all times.

With FIG. 3 in mind, and with further reference to FIG. 2, it will be noted that the first angular orientation YR1 of sensing element 122A (shown in solid lines) may correspond generally to a peak expiration 146 (e.g. end of the expiratory active phase (TEA)) while the second angular orientation YR2 of sensing element 122A (shown in dashed lines) may correspond to a peak 148 of inspiratory phase (TI), i.e. the end of inspiration just at or before the onset of expiration.

With further reference to FIG. 2, upon rotation (B2) of at least a first portion of chest wall 102A, as represented by directional arrow B2 and the depiction of chest wall in dashed lines 102B, such as during inspiration, the sensing element 122A rotates by the inclination angle ($\Omega$) with chest wall 102A to a position or orientation YR2 shown in dashed lines 122B. Upon the end of inspiration, and the ensuing expiration, the chest wall 102 will rotate back into the position shown in solid lines (e.g. end of expiration) such that the sensing element 122A will sense a change in inclination angle ($\Omega$) from the position YR2 (shown in dashed lines) back to the position YR1 (shown in solid lines).

In sensing the inclination angle ($\Omega$) through successive respiratory cycles, the sensing element 122A obtains an entire respiratory waveform, which may comprise information such as the duration, magnitude, etc. of an inspiratory phase (TI), expiratory active phase (TEA), and expiratory pause phase (TEP) of respiratory cycles of the patient, and/or other information (e.g. respiratory rate, etc.) as represented in FIG. 3 and/or as further described later. With this in mind, in some examples the obtained respiratory waveform (e.g. respiration morphology) also comprises a respiratory period, which includes the inspiratory phase, the expiratory active phase, and the expiratory pause phase. In one aspect, the respiratory period corresponds to a duration of a respiratory cycle, with this duration comprising a sum of a duration of the inspiratory phase, a duration of the expiratory active phase, and a duration of the expiratory pause phase.

In some examples, the identified respiration morphology comprises identifying (within the respiratory waveform morphology) a start of the inspiratory phase, i.e. onset of inspiration. In some examples, this start of the inspiratory phase also may at least partially correspond to an expiration-to-inspiration transition. In some examples, a method of identifying the start of the inspiratory phase within the identified respiratory waveform morphology further comprises performing the identification (of the start of the inspiratory phase) without identifying an end (e.g. offset) of the inspiratory phase, which may enhance the accuracy of identification (of the start of the inspiratory phase) in the presence of noise, in contrast to identification of more than one phase transition (e.g. inspiratory-to-expiratory or expiratory-to-inspiratory) per respiratory cycle where each transition is subject to mis-identification due to noise. In some such examples, the end (e.g. offset) of the inspiratory phase corresponds to a start (e.g. onset) of the expiratory active phase.

In some examples, identifying the respiratory waveform morphology may comprise identifying (within the respiratory waveform morphology) a respiratory peak pressure, which predictably occurs a short interval after the end of inspiration and which may be used in aspects of respiration detection and related parameters. In one aspect, this arrangement may enhance the accuracy of identification (of an inspiratory-to-expiratory transition, end of inspiration, etc.) in the presence of noise due to the ease of identification of the relatively high mathematical derivative of the pressure signal associated with the interval following the end of inspiration.

In some examples, the identification of respiratory waveform morphology may comprise identifying (within the respiratory waveform morphology) an end of expiration, which may be used in some aspects of respiration detection and related parameters.

In some examples, at least some aspects of such identification, prediction, etc. of features (e.g. start of inspiratory phase, end of expiration, etc.) within a respiratory waveform may be implemented via at least some of substantially the same features and attributes as later described in association with at least FIGS. 24A-24F and/or various examples throughout the present disclosure, such as but not limited to identifying inspiratory phase (e.g. 2352 in FIG. 24A), inspiratory phase prediction (e.g. 2360 in FIG. 24D), etc.

With further reference to FIG. 2, it will be understood that the second angular orientation YR2 of sensing element 122A is not a fixed position, but rather corresponds to a temporary position at one end (e.g. a second end) of a range of rotational movement of the portion of the chest wall 102A, such as peak inspiration 148 (FIG. 3) during breathing. This second end of the range of rotational movement (and therefore the second angular orientation YR2) may vary depending upon whether the patient is exhibiting normal/relaxed breathing, forced breathing (such as more forceful inspiration), and/or disordered breathing. Moreover, this second end of the range of rotational movement may exhibit some variance from breath-to-breath even during relaxed breathing.

Similarly, the first angular orientation YR1 of sensing element 122A shown in FIG. 2 does not comprise a fixed position, but rather the first angular orientation YR1 corresponds to a temporary position at an opposite other end (e.g. a first end) of a range of rotational movement of the portion of the chest wall 102A, such as peak expiration 146 (FIG. 3) during breathing. This first end of range of rotational movement (and therefore the first angular orientation YR1) may vary depending upon whether the patient is exhibiting normal/relaxed breathing, forced breathing (such as more forceful expiration), and/or disordered breathing. Moreover, this first end of the range of rotational movement may exhibit some variance from breath-to-breath even during normal/relaxed breathing.

While there may be some variances in the exact rotational positions of the respective second angular orientation YR2 and/or the first angular orientation YR1, it will be understood that there consistently will be a significant difference between the first angular orientation YR1 and the second angular orientation YR2, by which respiration morphology (e.g. shown in FIG. 3) can be determined as the sensor moves through the full range of rotational movement between the first and second angular orientations, YR1 and YR2 during patient breathing. Moreover, the variances in the particular rotational position of the first angular orientation YR1, and of the second angular orientation YR2, at the ends of the range of rotational movement of the sensing element 122A may yield valuable information regarding variances in respiration, such as variances in amplitude of inspiration and/or expiration, variances in respiratory rate, etc. In some examples, the ends of the range of angular movement between the two orientations YR1, YR2 may correspond to the ends of a range of values of an AC signal component of the acceleration signal from the sensor.

In some examples, the first angular orientation YR1 may sometimes be referred to as a reference angular orientation, at least to the extent that the first angular orientation YR1 may correspond to an orientation which is the closest to being generally perpendicular to the gravity vector G for at least some sleeping body positions, such as but not limited to a generally horizontal sleep position.

With further reference to FIG. 2, in this example implementation and in general terms, the sensor 104A may be implanted in a manner to cause the first angular orientation YR1 (i.e. base orientation) of the measurement axis of the sensing element 122A to be generally parallel to a superior-inferior (S-I) orientation of at least the chest region of the patient's body, and generally perpendicular to an earth gravitational field G, such as when the patient is in a generally horizontal position. In this example implementation, the measurement axis of the sensing element 122A also may understood as having an orientation generally perpendicular an anterior-posterior (A-P) orientation of at least a portion of the chest region 102A of the patient's body.

In the example of FIG. 2, rotational movement of sensing element 122A, which has a Y-axis orientation, occurs roughly near or within a plane P1 defined by the anterior-posterior orientation (A-P) and by the superior-inferior orientation (S-I) of the patient's body. This rotational movement is primarily indicative of rotational movement of the rib cage during breathing, such as during a treatment period in which a patient is sleeping. Additional examples later describe additional/other aspects in which rotational movements of the rib cage are further indicative of breathing, and therefore respiratory morphology.

It will be understood that, due to patient-to-patient variances in anatomy and/or due to the particular location where the sensor 104 is actually implanted along the chest wall 102A, the sensing element 122A may extend in an orientation which is not exactly parallel to a superior-inferior orientation the chest wall (or entire patient as a whole), and not exactly perpendicular to an anterior-posterior orientation of the patient's body (and gravity vector G when laying in a generally horizontal position).

Nevertheless, in some example implementations, by arranging the measurement axis (Y) of the sensing element 122A to have an orientation as close as possible to being generally perpendicular to the gravity vector (G) for at least some patient body positions (e.g. generally horizontal sleep position), the sensitivity of the AC signal component of the acceleration sensing element 122A is maximized (and absolute value of the DC signal component of minimized), which in turn may increase the effectiveness of measuring changes in the inclination angle ($\Omega$) of sensing element 122A caused by, and during, breathing by the patient. In one aspect, the AC signal component of the acceleration sensing element 122A may be understood as the time-varying portion of the output signal of the acceleration sensing element 122A.

In particular, by arranging the sensing element 122A within the chest wall 102A to be as close as reasonably practical to being generally perpendicular to the earth gravitational field G (at least when the patient is in a primary sleep position), the sensed inclination angle will correspond to a maximum value of a measured AC component of the acceleration signal and a minimum absolute value of measured DC component of the acceleration signal. Stated differently, when a measurement axis of the acceleration sensing element 122A is generally perpendicular (or as close as reasonably practical) to an orientation in which it would otherwise measure a maximum value (e.g. 1 g, such as when parallel to an earth gravity vector), the absolute value of the DC component will be negligible or minimal. In this situation, changes in value of the AC component of the acceleration signal become more prominent, being of a magnitude and/or reflecting significantly measurable changes as an orientation of the (measurement axis of the) acceleration sensing element changes (e.g. inclination angle) as the portion of the chest wall exhibits rotational movement caused by breathing.

It will be understood that based on the particular orientation at which the sensor 104 (e.g. sensing element 122A) is actually implanted, based on the varying position of the patient once the sensor 104 has been implanted, and/or based on other factors described further below, the measurement axis of the sensing element 122A at the chest wall 102A may not be perpendicular to the earth gravitational field G at the time of performing the sensing during breathing and hence the sensitivity of the AC component of the acceleration signal may not be at a maximum value. Nevertheless, at least some example methods (and/or devices) may perform the sensing (e.g. of the inclination angle of the sensing element 122A) to obtain the desired respiration information provided that the sensed signal provides a sufficiently high degree of sensitivity of a measured AC component of the acceleration signal. In some such examples, the methods and/or devices may employ magnitude criteria by which it may be determined if, and/or when, a sufficiently high degree of sensitivity of the measured AC signal is present. For instance, in some non-limiting examples, a sufficiently high degree of sensitivity corresponds to a measured AC signal having adequate signal to noise ratio in order to determine respiration.

In some such examples, an output acceleration signal of sensing element 122A corresponds to a sine of the angle between the accelerometer measurement axis (i.e. orientation of Y) and a generally horizontal orientation (which is generally perpendicular to gravity vector G).

Because of variances in patient-to-patient anatomy, in some example methods/devices, an absolute magnitude of the AC signal component is not used to determine respiration information. Rather, by using the difference in magnitude of the value of the AC signal component between the first angular orientation (YR1) and the second angular orientation (YR2), the example methods/devices can determine a respiratory waveform, morphology, etc.

In some examples, depending on the particular angle at which the device and sensor are implanted in a particular patient, and/or depending on the particular sleeping position in which the patient is arranged, the inspiration identified from the sensed respiratory waveform may have a positive slope or may have a negative slope. In some such examples in which the positive slope may be considered a default or primary mode, the negative slope may be considered to an inverted signal or exhibiting inversion of the respiratory waveform signal. Accordingly, in some examples, the example device/method may comprise a component such as slope inversion parameter 2594 in FIG. 24F for accounting the particular slope of the inspiratory phase of the respiratory waveform exhibited during sensing the signal, such as when a signal inversion may take place. In some such examples, the positive slope or the negative slope of the inspiratory phase may sometimes be referred to as a polarity of the slope of the inspiratory phase. It will be understood that in accounting for the particular slope of the inspiratory phase, the slope of the other phases of the respiratory cycle will be accounted for as well.

With these features in mind regarding the slope of the inspiratory phase of the respiratory waveform signal, at least some of the example methods and/or devices of the present disclosure may accurately capture and determine respiratory information regardless of how the patient may be moving in space, e.g. regardless of the direction of the sensor rotation in space or regardless of rotation of the patient (including the sensor) with respect to gravity. Accordingly, the example methods and/or devices may produce accurate, reliable determination of respiration information.

Accordingly, at least some example methods comprise implanting sensor 104A (including sensing element 122A) in a manner to maximize sensitivity of the AC component of the sensed acceleration signal by establishing an orientation (e.g. YR1) of sensing element 122A which is closest to being generally perpendicular to the gravity vector G, for at least some body positions such as a common sleep position (e.g. generally horizontal). In some situations, the sensor 104A (including sensing element 122A) may be implanted in a position in which the sensitivity of the AC component of the sensed acceleration signal is not maximized but which is sufficient to effectively and reliably determine respiration information based on sensed rotational movement at a first portion of a chest wall (or other physiologic location as described below). In some such examples, a sufficient sensitivity of the AC component of the sensed acceleration signal may comprise having an adequate signal-to-noise ratio.

With further regard to the observation that the device (including the acceleration sensor(s)) may be implanted at various particular orientations (e.g. angles) which are not parallel an ideal reference orientation (e.g. superior-inferior), it will be understand that in some examples, the example methods/devices determine the respiration information (e.g. using acceleration-based sensing of rotational movement of a portion of a chest wall, etc.) without calibrating the measured inclination angle signal (of the acceleration sensor) relative to any difference between the ideal reference orientation (e.g. superior-inferior) and the actual implant orientation (as shown later at 5400 in FIG. 34). However, in some examples, such calibration may be performed and/or such differences may be considered in using the sensed information.

As noted elsewhere, in at least some examples, determining respiration information based on acceleration sensing of rotational movement (of a portion of the chest wall) does not depend on the sensor having an ideal implant orientation, does not depend on knowing the actual implant orientation, and/or does not depend on accounting for differences between the ideal implant orientation and the actual implant orientation.

In some later example implementations, a sensor comprises multiple sensing elements such that the example methods may comprise determining which of the multiple sensing elements has an orientation which is closest to being generally perpendicular to gravity vector, and therefore which may provide the most sensitivity and effectiveness in sensing respiratory information. In some such examples, the multiple sensing elements may be oriented orthogonally relative to each other or may be oriented at other angles (e.g. 45 degrees) relative to each other.

With further reference to at least FIG. 2, in some examples, the term "generally perpendicular" may comprise the first angular orientation YR1 being at some angle relative to the gravity vector G (e.g. 85, 86, 87, 88, 89, 91, 92, 93, 94, 95 degrees) which varies slightly from an exactly perpendicular angle (e.g. 90 degrees) relative to the gravity vector G. Moreover, as noted above and/or further described below, the effectiveness of measuring respiration by changes in the inclination angle (Ω) between the first and second orientations (YR1, YR2) does not strictly depend on the first angular orientation YR1 being exactly perpendicular to the gravity vector G.

However, as further described later in association with at least FIGS. 15-16, the first angular orientation YR1 may be at angles other than generally perpendicular relative to the gravity vector (G), such as in example implementations in which the first angular orientation YR1 of a sensing element (e.g. 122A) is positioned to be about 135 degrees relative to gravity vector G (i.e. 135 degrees to an anterior-posterior (A-P) orientation of patient's body. In some such examples, the second angular orientation YR2 of sensing element 122A would still extend at an angle (Ω) relative to the first angular orientation YR1, with it understood that angle (Ω) varies according to the variances in respiration of the patient which occur in normal breathing, forced breathing, and/or disordered breathing, as previously described. As further described later, establishing the first orientation TR1 at angles other than 135 degrees are contemplated as well.

As further described later in association with at least FIGS. 37A-37B, noise model parameter 2470 in FIG. 24E, and/or noise parameter 2596 in FIG. 24F, the example device(s) and/or example method(s) may perform such measurements in a manner to exclude (e.g. filter) measurements of gross body motion, measurement noise, muscle noise, cardiac noise, other noise, etc. such that the remaining sensed or measured acceleration signal is primarily representative of movement of at least a portion of the chest wall 102. In some such examples, the measured acceleration signal is representative solely of movement of the chest wall 102. In particular, in some such examples, the measured acceleration signal corresponds to rotational movements of at least a portion of the chest wall 102 as sensed by sensor 104 (B1 in FIG. 1) caused by and/or occurring during breathing.

Figure 4A:
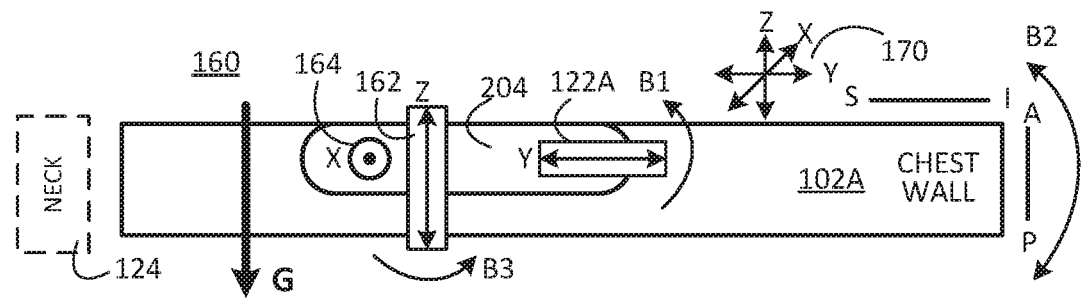
FIGS. 4A and 4B are each a diagram, including a side view, schematically representing an example method and/or example device for detecting respiration via an acceleration sensor.
Figure 4B:
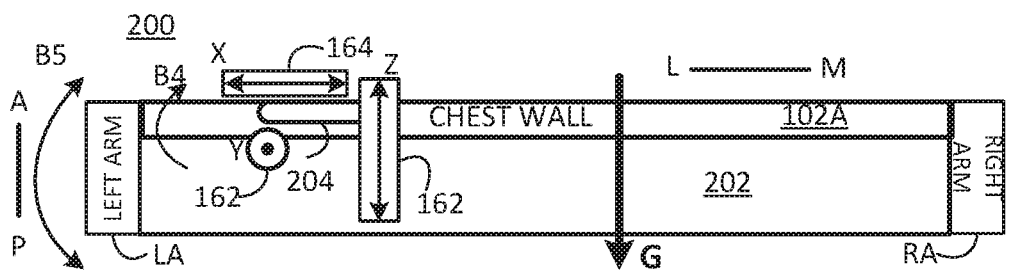
Figure 5:
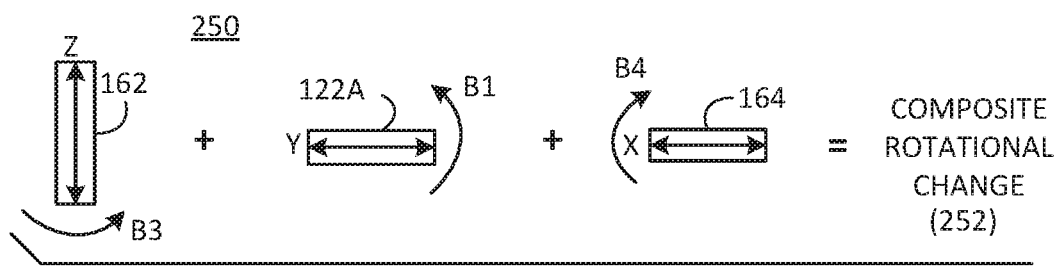
FIG. 5 is a diagram schematically representing example acceleration sensing elements.

FIGS. 4A, 4B, 5 are diagrams which schematically represent an example method and/or example sensor 204 which may comprise three sensing elements 122A (Y), 162 (Z), 164 (X) arranged orthogonally relative to each other. In some examples, the sensor 204 (including at least sensing element 122A) comprises at least some of substantially the same features and attributes as sensor 104A previously described in association with at least FIGS. 1-3 in which just one sensing element 122A (Y) is present. However, as shown in FIGS. 4A-4B, in addition to sensing element 122A (Y), in some examples sensor 204 also may comprise acceleration sensing element 162 having orientation Z (Z-axis) which is perpendicular to sensing element 122A. As implanted, this Z-axis orientation is generally perpendicular to a superior-inferior (S-I) orientation of the chest wall 102A, and is generally parallel to an anterior-posterior (A-P) orientation of the chest wall 102A.

Meanwhile, as shown in FIG. 4B, in addition to comprising sensing element 122A (Y), in some examples sensor 204 also may comprise acceleration sensing element 164, having orientation X (X-axis) which is generally perpendicular to sensing element 122A. As implanted, this X-axis orientation is generally perpendicular to a superior-inferior (S-I) orientation of the chest wall 102A, and generally perpendicular to an anterior-posterior (A-P) orientation of the chest wall 102A. In some such examples, sensing element 164 may sense rotational movement of chest wall 102A (as represented by directional arrow B5) in a plane defined by the anterior-posterior orientation (A-P) and by the lateral-medial orientation (L-M), according to changes in an inclination angle (as represented via directional arrow B4) of sensing element 164. Each of the respective sensing elements 162 (Z), 164 (X) may provide additional sensing of rotational movement of the chest wall 102A to provide further respiration information.

With further reference to FIGS. 4A, 4B, and 5, in some examples, sensor 204 may comprise all three sensing elements 122A (Y), 162 (Z) and 164 (X).

As schematically represented in the diagram 250 of FIG. 5, the sensed acceleration signal information from each of the three sensing elements 162, 122A, 164 of sensor 204 may be combined to provide composite rotational change information (252). In some examples, the composite rotational change information 252 may sometimes be referred to as a virtual vector representing the overall rotational movement (e.g. according to at least two orthogonal axes) caused by breathing. In some such examples, the composite rotational change information 252 corresponds to sensing the AC component of the multi-dimensional acceleration vector (e.g. a virtual vector) with respect to gravity.

In some examples, at least two of the three orthogonally-arranged sensing elements may be used to perform determination of composite rotational movement and therefore respiration information at least based on an AC component of a multi-dimensional acceleration vector produced by the n single-axis sensing elements.

In some such examples associated with FIG. 5, the virtual vector corresponding to the composite rotational change (252) may exhibit higher sensitivity to respiration than any single vector of a physical sensing element 122A (Y), sensing element 162 (Z), or sensing element 164 (X). In some such examples, the virtual vector (252) may exhibit a higher signal-to-noise ratio (e.g. signal quality) than any single physical vector, such as single sensing element 122A (Y) or single sensing element 162 (Z) or single sensing element 164 (X) by virtue of combining the signals of the multiple sensing elements.

In some such examples, the virtual vector (e.g. 252) effectively excludes non-physiologic motion of the chest wall. At least some examples of such non-physiologic motion may comprise motion of a vehicle (e.g. car, airplane, etc.) within which the patient is riding, of patient swinging in a hammock, and the like. Accordingly, determining respiration information via the virtual vector in such example methods and/or devices may produce respiration information which is generally insensitive to non-physiologic motion of the patient.

In some examples, respiration detection may be based on a sum of two of the vectors from among the three orthogonally-arranged sensing elements 322A, 5062, 5064 in FIG. 56C. In some examples, respiration detection may be based on a sum of signals from all three orthogonally-arranged sensing elements 322A, 5062, 5064 in FIG. 56C.

In some examples, respiration detection may be determined by looking independently at each of the three vectors (e.g. 322A, 5062, 5064) or from among the three vectors.

In some examples, a method and/or device may employ control portion 4000 (FIG. 25A) to select the virtual vector (e.g. 252) or a physical vector from one of the sensing elements 122A, 162, or 164 for use in determine respiration information. In some such examples, the method and/or device may evaluate the robustness of the determined respiration information and automatically convert operation among the virtual vector (e.g. 252 in FIG. 5) and any one of the physical vectors (e.g. 122A/Y, 162/Z, 164/X) to consistently use the most robust, accurate signal source in determining respiration information.

In association with the examples of at least FIGS. 4A, 4B, 5, in some examples the signal-to-noise ratio of a virtual vector and/or physical vector may be enhanced via excluding noise, such as later described in association with at least noise model parameter 2470 (FIG. 24E), method 5550 (FIG. 37A), and/or method 5555 (FIG. 37B).

In some examples, the above-described measuring of rotational movement (of a portion of a chest wall via acceleration sensing) per sensing element 162 (Z-axis) may be likened to a pitch parameter, measuring rotational movement per sensing element 122A (Y-axis) may be likened to a yaw parameter, and measuring rotational movement per sensing element 164 (X-axis) may be likened to a roll parameter. Because of variances in anatomy from patient to patient, the particular implant orientation, and/or the particular implant location (e.g. front vs. side of the chest), the pitch parameter, yaw parameter, and/or roll parameter may bear a rough or general correspondence to the ideal definition for such respective parameters in which the pitch parameter may correspond to rotational movement of the portion of the chest wall in a first plane defined by an anterior-posterior orientation and by a superior-inferior orientation of the patient's body. Similarly, the yaw parameter may roughly or generally correspond to rotational movement of the portion of the chest wall in a second plane defined by the anterior-posterior orientation and by a lateral-medial orientation of the patients' body. Similarly, the roll parameter may roughly or generally correspond to rotational movement of the portion of the chest wall in a third plane defined by the lateral-medial orientation and by the superior-inferior orientation of the patient's body.

In examples in which the patient's body position corresponds to a primary sleeping position (e.g. generally horizontal), then the magnitude of changes in the AC signal component from rotational movement (B3) sensing element 162 (Z axis) during breathing will be negligible and the magnitude of changes in the AC signal component from rotation (arrow B4) of sensing element 164 (X axis) during breathing may be relatively small at least compared the magnitude of changes in the AC signal component of sensing element 122A (Y-axis) during breathing (as described in association with FIGS. 1-3).

Figure 7:
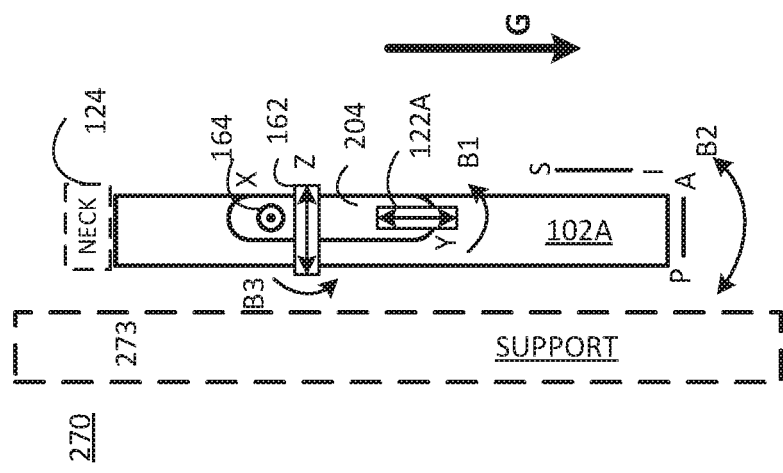
FIG. 7 is a diagram including a side view schematically representing an example method and/or example device for detecting respiration with a patient relative to an upright support.
Figure 6A:
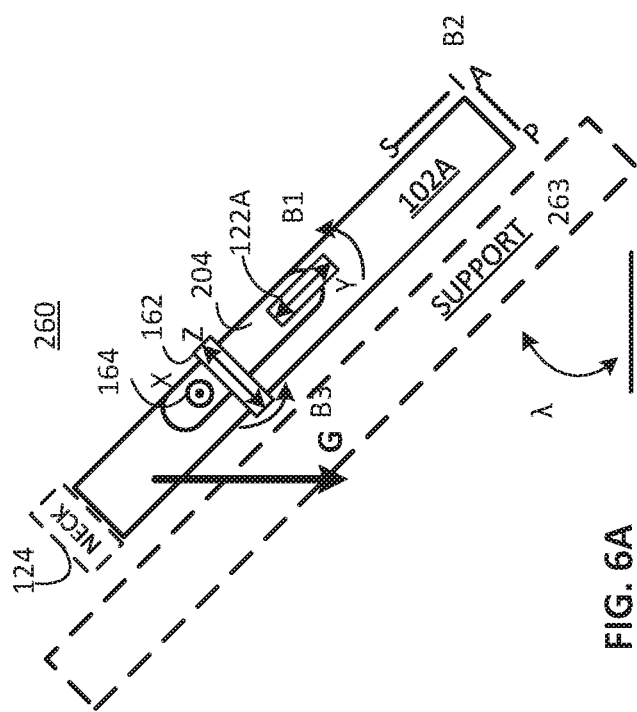
FIG. 6A is a diagram including a side view schematically representing an example method and/or example device for detecting respiration with a patient relative to an angled support.

However, in some example situations the patient's body position may correspond to a secondary or alternate sleep position, such as sitting upright against a support 273 (e.g. ordinary chair, airplane chair, etc.) as shown in FIG. 7 or in a partially reclined position (e.g. torso is 45 degrees from horizontal) against a support 263 (e.g. recliner chair, recliner bed, etc.) which is at angle (λ) relative to generally horizontal (e.g. floor) as shown in FIG. 6A. In some such examples, such as the partially reclined position in FIG. 6A, at least the respective sensing element 162 (Z axis) may yield significant magnitude of changes in the AC signal component during breathing instead of and/or in addition to sensed changes in the AC signal component of sensing element 122A (Y-axis) during breathing. In this example, the sensing element 122A may comprise a first angular orientation (like YR1 in FIG. 2 for peak expiration) which is 45 degrees (a in FIG. 6B) relative to the gravity vector G (and which is 45 degrees relative to a generally horizontal plane, which typically is a primary sleep position). While the first orientation (e.g. YR1) of the sensing element 122A may not be generally perpendicular to the gravity vector G as in FIG. 2, at the first orientation of 45 degrees (a in FIG. 6B) relative to the gravity vector G, the acceleration sensing element 122A still exhibits sufficient sensitivity in the AC signal component to produce meaningful measurements in changes of the inclination angle (e.g. Ω in FIG. 2) of sensing element 122A between the first and second orientations (e.g. YR1 and YR2) during breathing to enable determining respiration information.

In this example, the sensing element 162 may comprise a first orientation (like YR1 in FIG. 2) which extends at an angle of 135 degrees (8 in FIG. 6C) relative to the gravity vector G (and which is 45 degrees relative to a generally horizontal plane, which typically is a primary sleep position). While the sensing element 162 may not be generally perpendicular to the gravity vector G (as was sensing element 122A in the example of FIG. 2), at the first orientation of 135 degrees (θ in FIG. 6C) relative to the gravity vector G, the acceleration sensing element 162 exhibits sufficient sensitivity in the AC signal component to produce meaningful measurements in changes of the inclination angle (like Ω in FIG. 2) of sensing element 162 between its first orientation (peak expiration) and second orientation (peak inspiration) during breathing to enable determining respiration information.

In a manner similar to that shown in FIG. 5, the sensed rotational movement from at least the multiple sensing elements (e.g. 162/Z-axis and 122A/Y-axis in FIGS. 6A-6C) may be combined to yield a composite value of sensed rotational movement of sensor 204 in order to produce sensing of a respiratory waveform while the patient is in the partially reclined position.

Figure 6C:
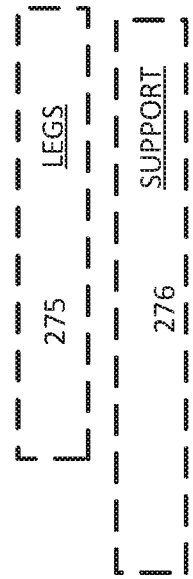
FIGS. 6B and 6C are each a diagram schematically representing an example method and/or example device including a sensing element extending at a particular angle relative to a gravity vector.
Figure 6B:
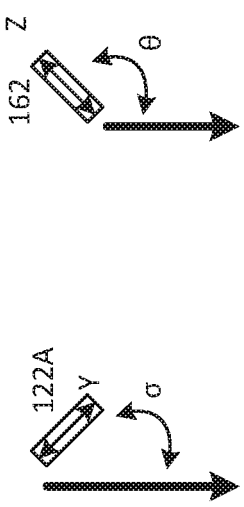

It will be further understood that, in some examples, the sensing element 164 (X-axis) also may be used in addition to sensing elements 122A, 162 (and in a manner similar to that described for sensing elements 122A, 162 in FIGS. 6A-6C) to provide further sensing by which the determination of respiration information can be made, with the rotational sensing information being combined, similar to that shown in FIG. 5. With this in mind and with further reference to at least the examples of FIGS. 6A-6C and 7, it will be understood that employing a three axis accelerometer (in which the three axes are orthogonally-arranged) will ensure that at least one of the three axes will have an output signal of magnitude sufficient to reliably determine respiration (e.g. based on rotational movement of the sensor in correspondence with rotational movement of a portion of the chest wall during breathing as described in various examples).

It will be understood that in some examples, the particular angle λ of reclination in FIG. 6A may be angles other than 45 degrees, and may be variable over time in some instances, depending on the type and manner of support 263 (e.g. adjustable bed, chair). In some such examples, a determination of respiration information may be based on the particular respective sensing element(s) (e.g. 122A (Y-axis), 162 (Z-axis), 164 (X-axis)) having the orientation(s) closest to being generally perpendicular to the gravity vector G for the particular angle λ at a particular point in time.

Moreover, in this example arrangement of FIGS. 6A-7, if and/or when the patient moves to another sleeping position, such as generally horizontal position (e.g. FIG. 2), then the sensing element 122A (or sensing element 164) may become the sole or primary signal source for detecting respiration in some examples.

Accordingly, example arrangements of multiple single-axis acceleration sensing elements in orthogonal relationship to each other may provide robust sensing of respiration which enables adaptability in response to a patient moving among different sleep positions within a single treatment period or among multiple, different treatment periods.

As previously noted, FIG. 7 schematic represents at least a chest wall 102A of a patient's body in a generally vertically upright position, such as if the patient were sitting on a support 276 with their torso against a vertical support 273. In this example arrangement, both the acceleration sensing elements 162 (Z-axis) and 164 (X-axis) of sensor 204 may have a first orientation which is generally perpendicular (or reasonably close to being generally perpendicular) to gravity vector G, whereas the acceleration sensing element 122A (Y-axis) of sensor 204 has a general orientation which is generally parallel to gravity vector G. Accordingly, for substantially similar reasons presented with respect to FIGS. 2-6C, one or both of the sensing elements 162 (Z-axis), 164 (X-axis) may provide the most sensitive sensing elements by which respiration information determination may be performed. In particular, upon rotational movement of the patient's chest wall 104A during breathing within a treatment period, rotational movement of Z-axis sensing element 162 between a first orientation (e.g. like YR1 in FIG. 2) and a second orientation (e.g. like YR2 in FIG. 2) may be sensed as range of values of an AC signal component from which a respiratory waveform (including respiratory phase timing/details) may be determined as shown in FIG. 3. Moreover, rotational movement of X-axis sensing element 164 may provide similar information and may be used to determine respiration information. The respiration information may be determined solely from the Z-axis sensing element 162, solely from the X-axis sensing element 164, or from a combination of information sensed via both of the Z-axis sensing element 162 and the X-axis sensing element 164. While the Y-axis sensing element 122A would generally be expected to produce negligible or minimal respiration information (because of being parallel to the gravity vector G), in some examples, information sensed from Y-axis sensing element 122A may be combined with rotational information sensed via the sensing elements 162, 164.

Figure 8:
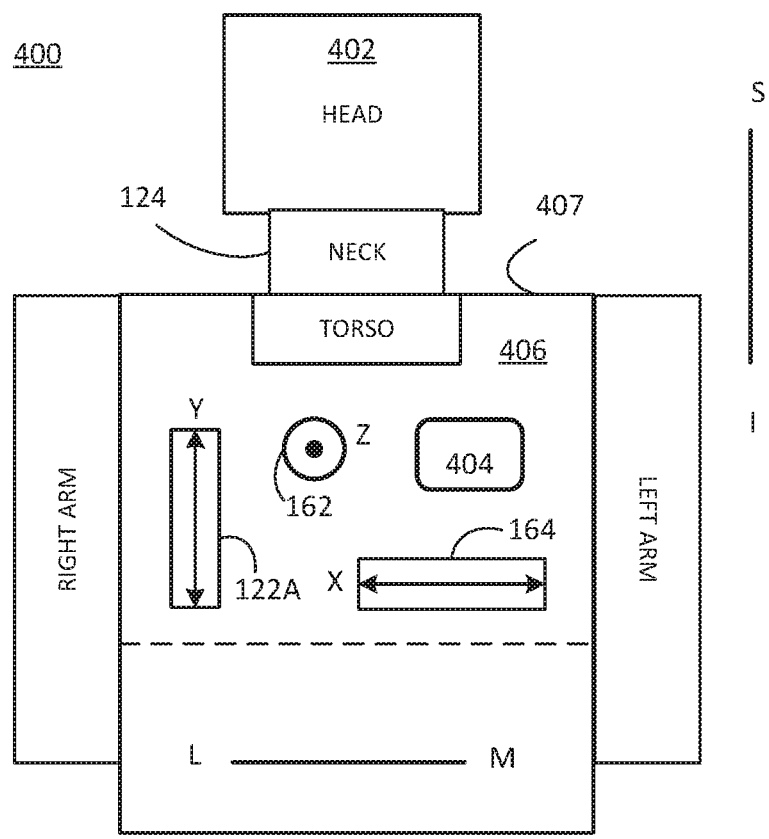
FIG. 8 is a diagram including a front view schematically representing an example method and/or example device in which different sensing elements of an acceleration sensor are oriented relative to a patient's body.
Figure 9:
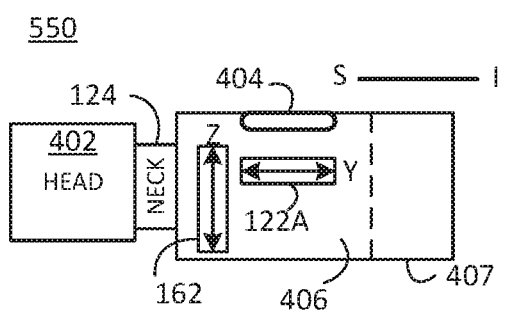
FIG. 9 is a diagram including a side view schematically representing an example method and/or example device in which different sensing elements of an acceleration sensor are oriented relative to a patient's body.

FIG. 8 is a diagram 400 including a front view schematically representing different measurement axes of an example sensor 404 and/or related example method. In some examples, the sensor 404 may comprise at least some of substantially the same features and attributes as the sensors, sensing elements, and related example methods as previously described in association with FIGS. 1-7. As shown in FIG. 8, sensor 404 is implanted within a wall of chest region 406 of torso 407 below a neck 124 and head 402. The sensor 404 comprises multiple sensing elements 122A (Y-axis orientation), 162 (Z-axis orientation), 164 (X-axis orientation), which may be independent such as three separate single-axis accelerometers, or these sensing elements may be combined into a single arrangement, such as a three-axis accelerometer. FIG. 9 is diagram 550 including a side view schematically representing the sensor 404 of FIG. 8, highlighting the orientation of the sensing elements 122A, 162.

Figure 10A:
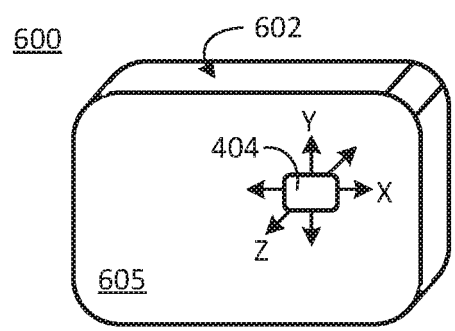
FIG. 10A is a diagram including a front view schematically representing an example method and/or example device including an implantable medical device comprising an acceleration sensor.

FIG. 10A is diagram 600 including an isometric view schematically representing an implantable device 602 comprising an accelerometer-based sensor 404, which may comprise at least some of substantially the same features and attributes as the sensors, sensing elements, and related example methods as previously described in association with FIGS. 1-9. It will be understood that the sensor (and sensing elements) described in FIGS. 1-9 may be implemented as being on or within device 602. In some examples, sensor 404 is enclosed within a sealed housing (e.g. can) of the device 602. However, as described further later in association with at least FIG. 20, the sensor 404 may be external to the housing 605 of device 602, whether located on the housing or extending from the housing 605 on a lead.

With further reference to FIG. 10A, in some examples, device 602 may comprise an implantable device, which includes circuitry and power elements to operate the sensor 404 to sense physiologic phenomenon, such as but not limited to respiration information. In some examples, the circuitry and power may be implemented within or as part of a control portion 4000 and/or related portions, elements, functions, parameters, engines, as further described later in association with at least FIGS. 24A-24F. Among other attributes, via the control portion, the device 602 may be used to monitor and/or diagnose physiologic phenomenon, patient conditions (e.g. respiratory health, cardiac health, etc.), with one such patient condition including sleep disordered breathing (SDB). In some examples, device 602 may comprise an implantable pulse generator (IPG), which may implement neurostimulation in association with respiration detection in order to treat sleep disordered breathing and/or other patient health conditions. In some such examples, the device 602 may also sense translational movements of the chest wall and/or associated body tissue in order to sense, monitor, diagnose, etc. the various physiologic phenomenon, patient conditions, etc. whether the sensed translational movement is obtained instead of, or in addition to, the sensed rotational movement of the portion of the chest wall.

In some examples, the sensor 404 may be mounted or otherwise formed on an external surface (e.g. case) 605 of the device 602 (e.g. IPG), or the sensor 404 may be enclosed within an interior of the device 602 (e.g. IPG), i.e. within the case.

With the examples of FIGS. 1-10A in mind, it will be understood that in some examples the sensor signal which will be used to determine respiration information may be selected from among multiple sensing elements, such as but not limited to, the individual axis of the three-axis accelerometer. Accordingly, at least some example methods and/or devices as described in association with at least FIGS. 10B-10L further describe such selection.

Accordingly, as shown at 800 in FIG. 10B, some example methods and/or devices for determining respiration information may comprise arranging the acceleration sensor as n number of orthogonally-arranged single axis acceleration sensing elements. As shown at 805 in FIG. 10C, in some examples the method comprises identifying, via the sensing, which of the n single axis acceleration sensing elements exhibits a reference angular orientation, during breathing, closest to being generally perpendicular to the gravity vector. In some such examples, as shown at 810 in FIG. 10D, the method comprises determining the reference angular orientation of each n axis acceleration sensing elements as an inclination angle of a measurement axis of each respective n axis acceleration sensing elements relative to the gravity vector.

In some examples associated with FIGS. 10A-10D, as shown at 820 in FIG. 10E, the method comprises implementing the sensing via sensing a AC signal component of the respective acceleration sensing elements while excluding (or at least minimizing) a DC signal component of the respective acceleration sensing elements.

With reference to the example method in at least 805 in FIG. 10C, the example method may comprise performing the determination of respiration information, via the sensed rotational movement, using the identified sensing element as shown at 830 in FIG. 10F. In some such examples, the method comprises performing the determination, via the sensed rotational movement, comprises using at least two of the acceleration sensing elements.

In some such examples as previously described in FIGS. 10B-10F, one example method comprises, as shown at 835 in FIG. 10G, determining the respiration information comprises sensing an AC signal component of the identified sensing element within a range of angular orientations of the identified sensing element, wherein a first end of the range of orientations corresponds to a peak expiration and an opposite second end of the range of orientations corresponds to a peak inspiration. In some examples, the first end of the range of orientations corresponds to the reference angular orientation.

As shown at 840 in FIG. 10H, in some examples of determining respiration information, the method comprises: (1) identifying which of the n single axis acceleration sensing elements exhibits a reference angular orientation, during breathing, within a range of about 45 degrees to about 135 degrees relative to the gravity vector; (2) sensing, for each respective identified acceleration sensing element, a range of angular orientations relative to the gravity vector, wherein a first end of the range of orientations corresponds to a peak expiration and an opposite second end of the range of orientations corresponds to a peak inspiration; and (3) determining which of the identified acceleration sensing elements exhibits a greatest range of angular orientations. In some examples, method 840 further comprises, as shown at 845 in FIG. 10I, performing the determination of respiration information, via the sensed rotational movement, using the identified acceleration sensing element determined to exhibit the greatest range of angular orientations.

In some such examples, such as at 840, the method may comprise performing the determination, via the sensed rotational movement, comprises using all of the identified acceleration sensing elements. In some examples of at least method 800 (FIG. 10B) and the associated aspects in FIGS. 10C-10I, the variable n equals 3.

With further reference to the example method shown at 800 in FIG. 10B, in some examples, as shown at 860 in FIG. 10J, some example methods comprise identifying which of the n single axis acceleration sensing elements, during breathing, exhibits a greatest range of values for an AC signal component. In some such examples, as shown at 870 in FIG. 10K, the method comprises performing the determination of respiration information, via the sensed rotational movement, using the identified acceleration sensing element determined to exhibit the greatest range of values of the AC signal component.

With regard to example methods in at least FIGS. 10J and/or 10K, the example method may comprise determining a sensing signal for each n axis acceleration sensing elements as an inclination angle of a measurement axis of each respective n axis acceleration sensing elements relative to the gravity vector, in a manner similar to that previously shown at 810 in FIG. 10D.

With regard to example methods in at least FIGS. 10J and/or 10K, one example method (as shown at 880 in FIG. 10L) may further comprise determining the respiration information via sensing an AC signal component of the identified sensing element during breathing, wherein a first end of a range of values of the sensed AC signal component corresponds to a peak expiration and an opposite second end of the range of values of the sensed AC signal component corresponds to a peak inspiration.

FIG. 11 is a diagram 1000 schematically representing a side view of a patient's chest in which is implanted an example device 602 and/or at which example method is performed. As shown in FIG. 11, device 602 has been chronically, subcutaneously implanted to be coupled relative to a portion 1002A of a patient's chest wall 1005 of chest 1001. In the particular example shown, the chest wall portion 1002A corresponds to an anterior portion of the rib cage/chest 1001. Meanwhile, the non-bony structures (e.g. fascia, muscle, etc.) overlying the rib cage, and within which the device 602 may be inserted, are omitted from FIG. 11 for illustrative simplicity and clarity.

In some examples, device 602 may comprise at least some of substantially the same features and attributes as device 602 in FIG. 10A, with sensor 404 comprising at least some of substantially the same features and attributes as the sensing elements described in association with FIGS. 1-10A.

As shown in FIG. 11, during breathing, the chest wall portion 1002A (shown in solid lines) rises into the position shown in dashed lines 1002B as the rib cage expands upon inspiration and then chest wall portion 1002A falls into the position shown in solid lines as the rib cage contracts during expiration, with the cycle repeating itself with each breath. As further shown in FIG. 11, when the rib cage is in a contracted state (e.g., peak expiration), the sensor 404 is in a first orientation (as represented by solid line indicator YR1) in a manner similar to that shown in FIGS. 2-3. When the rib cage in an expanded state (e.g. peak inspiration), the sensor 404B is in a second orientation (as represented by dashed line indicator YR2) in a manner similar to that shown in FIGS. 2-3. In one aspect, some inferiorly-located portions of chest wall (e.g. 1002A, which expands to position shown at 1002B) exhibit significant movement whereas other more superiorly-located chest wall portions 1008 may remain relatively stationary, such that the chest wall exhibits rotational movement which is sensed by sensor 404 and which is representative of respiratory behavior of the patient. Accordingly, by employing sensor 404 to measure an inclination angle (Ω) during such rotational movement of the chest wall portion 1002A during breathing, a suitable respiratory information signal may be obtained.

It will be understood that the device 602 (and sensor 404) is not limited to being implanted strictly at the location of the chest wall (along the superior-inferior orientation) depicted in FIG. 11, but may be closer to the superior end 1008 of the chest wall provided that a sufficient range of rotational movement of the chest wall (between inspiration and expiration) is detectable via sensor 404. Likewise, in some examples, the device 602 (and sensor 404) may be closer to the inferior end 1006 of the chest wall.

Moreover, it will be understood that while device 602 as shown in solid lines is depicted in a generally horizontal orientation within the FIG. 11, this representation does not limit the implantation of device 602 to such an orientation. In addition, as previously noted, the effectiveness of the device 602 (including sensor 404) to detect respiration information is not limited to having an exactly horizontal orientation but rather effectuated by the change in angular orientation (e.g. YR1 to YR2, and vice versa) of the inclination angle (Ω in FIG. 2) of the sensor 404, as previously described.

Figure 12:
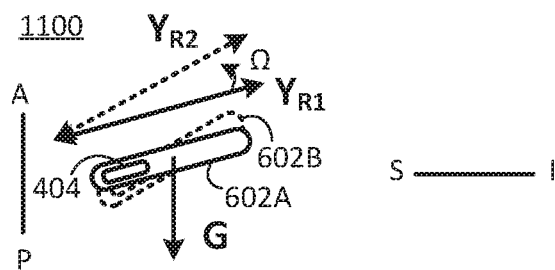
FIG. 12 is a diagram including a side view schematically representing different angular orientations upon rotation of an acceleration sensor relative to a gravity vector.

FIG. 12 is a diagram which schematically represents device 602 (including sensor 404) which is deployed in a manner consistent with at least FIGS. 1-11. Among other things, FIG. 12 demonstrates that in at least some instances the device 602, and therefore sensor 404) may be implanted such that it is has an orientation YR1 which is not generally parallel to a superior-inferior orientation (S-I) of the patient's chest (and body). Rather, in at least some examples, the orientation YR1 shown in FIG. 12 may result from the natural angle of the portion of chest wall at which the device 602 (and sensor 404) is implanted. Nevertheless, with regard to at least a primary sleep position in which the patient is generally horizontal (e.g. supine, prone, side-laying) the example methods and/or example devices remain effective in detecting respiration information because the primary mechanism of obtaining the respiration information is based on observing the change in value of the AC signal component associated with the measured inclination angle (Ω) through the range of rotational movement between first angular orientation YR1 (e.g. peak expiration) and second angular orientation YR2 (e.g. peak inspiration). Accordingly, provided that the first angular orientation YR1 at the time of measuring the signal extends at an appropriate angle relative to the gravity vector G (as extensively described in association with at least FIGS. 1-11) sufficient to obtain an AC signal component which is substantially sensitive to changes in an inclination angle (e.g. Ω in FIG. 2) of the sensor 404 (e.g. sensing element 122A in FIG. 2), then suitable determination of respiration information can be made.

Figure 13:
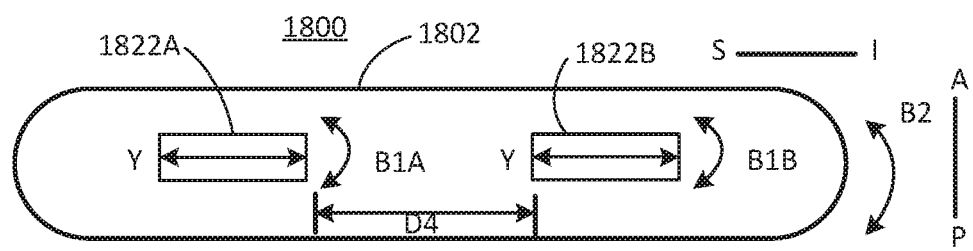
FIGS. 13, 14, 15A are each a diagram including a side view schematically representing an implantable medical device including two spaced apart, acceleration sensors and arranged in different configurations relative to each other.

FIG. 13 is a diagram 1800 including a side view schematically representing an example implantable device 1802 and/or example method. In some examples, the example device 1802 (and/or example methods) may comprise at least some of substantially the same features and attributes as the sensors (e.g. 404), sensing elements (e.g. 122A), devices (e.g. 602) and related example methods as previously described in association with FIGS. 1-12, except further comprising a second sensing element 1822B within device 1802 in addition to a first sensing element 1822A (like 122A in at least FIG. 2). The two sensing elements 1822A and 1822B are spaced apart by a distance D4 within the device 602. In some examples, the multiple sensing elements 1822A, 1822B provide multiple sources of respiration information for redundancy and/or to provide more robust sensing.

In some such examples, each sensor 1822A, 1822B may experience slightly different rotational movement and this difference signal may be used to increase sensitivity to angular movement such as occurs during respiration while reducing sensitivity to translational movement such as occurs due to non-respiratory muscle movement, in order to better determine respiration information. For instance, in some example, because the two separate accelerometers (e.g. 1822A, 1822B) are aligned along the same axis (in at least some examples), the two output signals could be subtracted from one another for an estimate of a true gyroscopic or rotational signal of the device (as opposed to the relative projection of the gravity vector). In some instances, two low gain signals (one from each accelerometer) may be added together for greater signal magnitude, may be averaged for reduction of sensor noise, and/or may be subtracted for a common-mode rejection.

Figure 14:
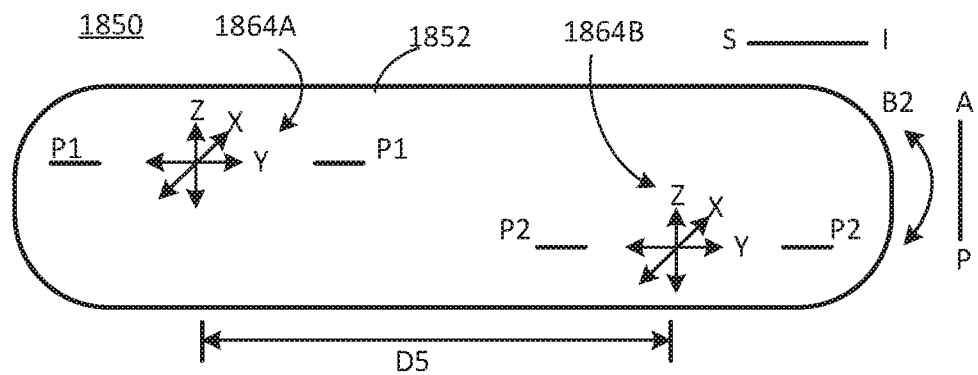

FIG. 14 is a diagram 1850 including a side view schematically representing an example implantable device 1852A and/or example method. In some examples, the example device 1852A (and/or example methods) may comprise at least some of substantially the same features and attributes as the sensors (e.g. 404), sensing elements (e.g. 122A), devices (e.g. 602) and related example methods as previously described in association with FIGS. 1-12, except further comprising two spaced apart, orthogonally-arranged multiple axes accelerometer sensors 1862A, 1862B which are spaced apart by a distance D5. In some examples, each sensor 1862A, 1862B comprises a three-axis accelerometer with each accelerometer having the same orientation within the device 1852A, e.g. the Y-axis sensing element of accelerometer sensor 1862A is generally parallel to the Y-axis sensing element of accelerometer sensor 1862B. In some examples, the respective accelerometer sensors 1862A, 1862B are in same plane (P1), i.e. the Y-axis sensing element of accelerometer sensor 1862A extends in the same plane (P1) as the Y-axis sensing element of accelerometer sensor 1862B. In some examples, this arrangement of providing two spaced apart three-axis accelerometer sensors may provide at least some information approximately the function of a gyroscope, while consuming less power. In addition, by having two separate and independent three-axis accelerometers, the arrangement may provide more robust signal capture.

However, as further shown in FIG. 14, in some examples the respective accelerometer sensors 1862A, 1862B extend in different planes (P1 and P2) within device 1852A, i.e. at least one axis sensing element (e.g. Y) of accelerometer sensor 1862A extends in a first plane (P1) which is different than a second plane (P2) in which a corresponding axis sensing element (e.g. Y) of accelerometer sensor 1862B extends. In some examples, this arrangement may enhance signal fidelity. It will be understood that in some examples another axis sensing element (e.g. X) of one accelerometer sensor 1862A also may extend in a plane different from the corresponding axis sensing element (e.g. X) of the second accelerometer sensor 1862B.

Figure 15A:
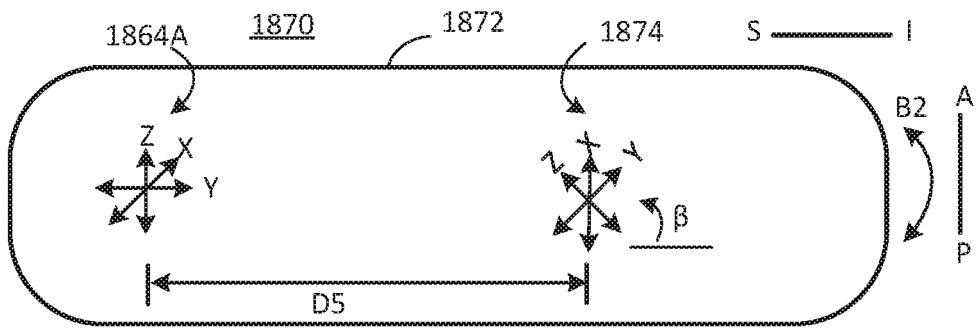

FIG. 15A is a diagram 1870 including a side view schematically representing an example implantable device 1872 and/or example method. In some examples, the example device 1872 (and/or example methods) may comprise at least some of substantially the same features and attributes as the sensors (e.g. 404), sensing elements (e.g. 122A), devices (e.g. 602) and related example methods as previously described in association with FIGS. 1-14, except further comprising two spaced apart, orthogonally-arranged multiple axes accelerometers 1864A, 1874 which are spaced apart by a distance D5 and which have different orientations within device 1872. In some examples, each sensor 1864, 1874 comprises a three-axis accelerometer with each accelerometer having different orientations within the device 1872, such as the one axis sensing element (e.g. Y) of accelerometer sensor 1874 not being generally parallel to the corresponding Y-axis sensing element of accelerometer sensor 1864A, but rather the Y-axis sensing element of sensor 1874 extending at an angle (β) relative to the Y-axis sensing element of sensor 1864A. In some examples this angle may comprise about 45 degrees.

In some examples, this angle (β) (by which the orientation of second accelerometer sensor 1874 is offset relative to first accelerometer sensor 1864A) may fall within a range of about −70 degrees to about 70 degrees and/or within a range in which the sensitivity of the AC signal component of the sensing element(s) (e.g. Y-axis sensing element, etc.) to changes in the inclination angle (e.g. Ω in FIG. 2, 11) remains sufficiently accurate and/or of a magnitude to reliably capture respiration information (including respiratory morphology) of the patient during breathing.

In some examples, this example arrangement provides for more robust sensing of respiratory information at least because, regardless of the particular implant angle (e.g. angle of device and sensor relative to the superior-inferior orientation of chest) and/or of the particular patient body position at the time of sensing, at least one of the three sensing axes of the first accelerometer 1864A and at least one of the three sensing axes of the second accelerometer 1874 will extend in an orientation having a sufficiently high sensitivity of an AC signal component of an acceleration signal to enable reliably and accurately measuring a change in inclination angle (Ω in FIG. 2) of (at least) the at least one sensing axes between a first angular orientation (e.g. YR1 in FIG. 2) and a second angular orientation (e.g. YR2 in FIG. 2).

Figure 15B:
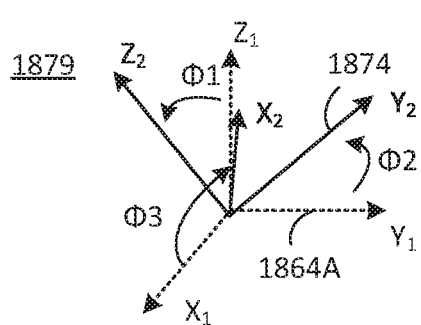
FIG. 15B is a diagram schematically representing an offset of angular orientation of the respective sensing elements of two spaced apart accelerometers.

It will be further understood that the second three-axis accelerometer 1874 may be secured within device 602 at an offset angle (β) relative to the secured position of first three-axis accelerometer 1864A within device 1852 for more than one axis (e.g. Y), such as being offset for two axes (e.g. Y, Z or Y, X) or three axes (e.g. Y, X, and Z), as shown in FIG. 15B.

For example, FIG. 15B is a diagram 1879 juxtaposing the respective axes (Z2, Y2, X2) of the sensor 1874 (shown in solid lines) relative to the respective axes (Z1, Y1, X1) of sensor 1864A (shown in dashed lines) to schematically represent a degree (φ1, φ2, φ3) by which each of the respective axes (Z2, Y2, X2) of the sensor 1874 (shown in solid lines) may be offset from the respective axes (Z1, Y1, X1) of sensor 1864 (shown in dashed lines). In some examples, angle φ1, φ2, φ3 all have the same value (e.g. 45 degrees, 50 degrees, 60 degrees, etc.) while in some examples, some of the angles (e.g. φ1) may have a value (e.g. 40 degrees) which is different than a value (e.g. 60 degrees) of another angle (e.g. φ2).

Figure 16:
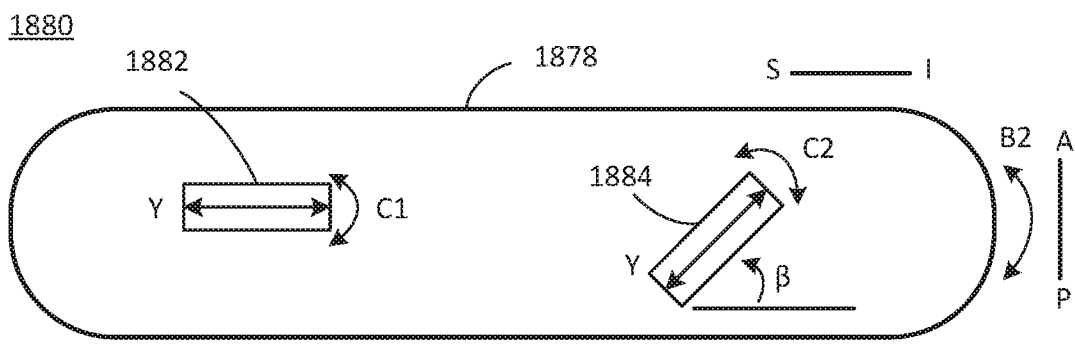
FIGS. 16 and 17 are each a diagram including a side view schematically representing an implantable medical device including two spaced apart, acceleration sensors and arranged in different configurations relative to each other.

FIG. 16 is diagram 1880 including a side view schematically representing an example implantable device 1801 and/or example method. In some examples, the example device 1878 (and/or example methods) may comprise at least some of substantially the same features and attributes as the sensors (e.g. 404), sensing elements (e.g. 122A), devices (e.g. 602) and related example methods as previously described in association with FIG. 1-15B, except further comprising two spaced apart single axis accelerometer sensing elements 1882, 1884 which are spaced apart by a distance D5 (like in FIGS. 14, 15A) and which have different orientations within device 1878. In some examples, each sensing element 1882, 1884 comprises a single-axis accelerometer with each accelerometer having different orientations within the device 1882, e.g. the acceleration sensing element 1882 (e.g. Y) being not generally parallel to the acceleration sensing element 1884 (e.g. Y) but rather the sensing element 1884 extending at an angle (β) relative to the sensing element of sensor 1882. Other than comprising two single axis acceleration sensors instead of two three-axis acceleration sensors (FIG. 15), the device 1882 may comprise at least some of substantially the same feature and attributes as device 1872 in FIGS. 15A-15B.

Figure 17:
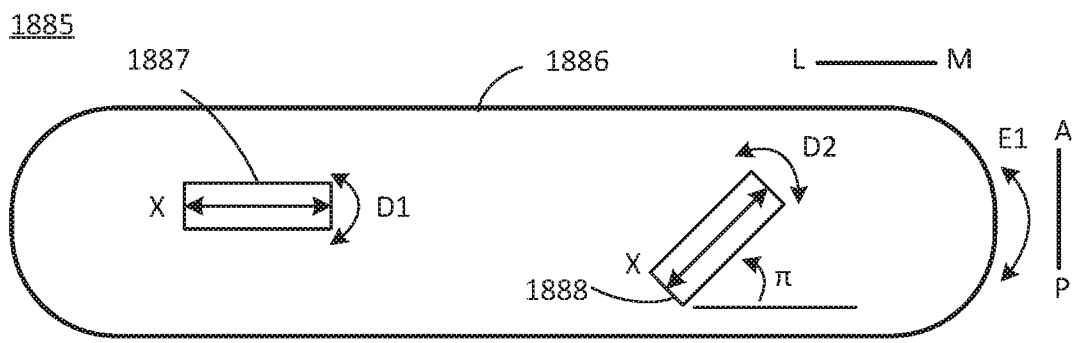

In a manner similar to the example of device 1878 in FIG. 16, in some examples, an implantable device 1886 as shown in FIG. 17 may comprise the same type of example arrangement to provide two single-axis acceleration sensing elements (1887, 1888) where the offset angle (π) is implemented relative to an x-axis extending in the lateral-medial orientation (L-M) of the patient's chest.

Figure 18A:
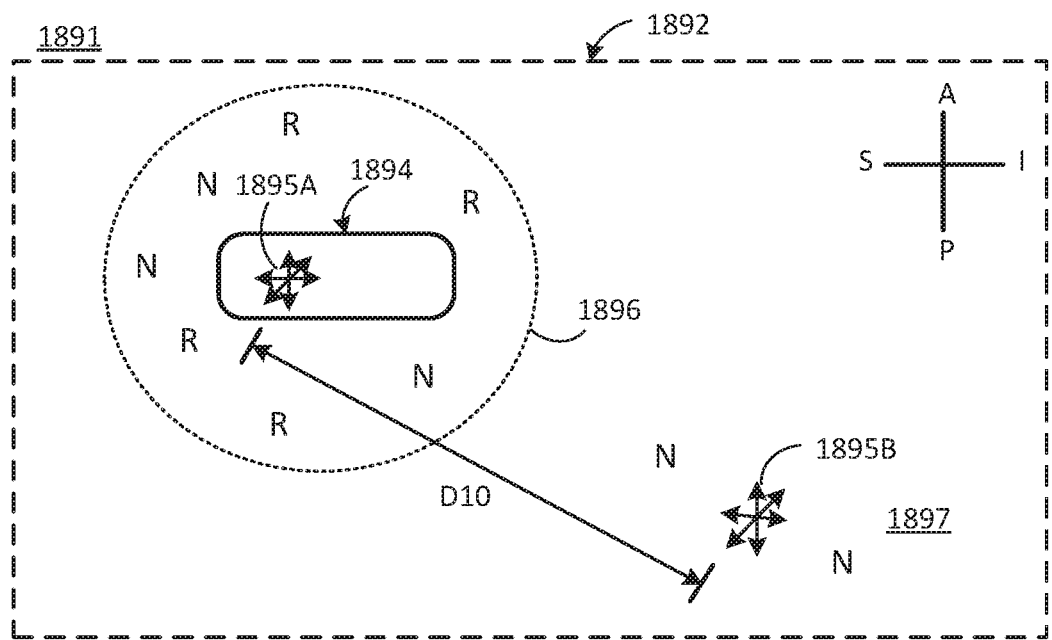
FIG. 18A is diagram schematically representing an example method and/or example device for detecting noise using two spaced apart accelerometers with one accelerometer in an implantable medical device to sense respiration and the other accelerometer spaced apart from the respiration sensing region.

FIG. 18A is a diagram including a top plan view schematically representing an example method 1891 (and/or device) including two separate acceleration sensors 1895A, 1895B, which are implanted within a patient's body 1892. In some examples, both the first and second acceleration sensors 1895A, 1895B comprise at least some of substantially the same features as the acceleration sensor described in association with at least FIGS. 1-17, etc. In some examples, the respective sensors 1895A, 1895B are spaced apart by a distance D10 such that a first acceleration sensor 1895A is positioned within a region 1896 of the patient's body 6302 in which the first acceleration sensor 1895A readily senses respiration (R) of the patient while the second acceleration sensor 1895B is implanted within the patient's body 1892 in a region 1897 which does not readily sense the patient's respiratory behavior (R). However, the distance D10 corresponds to a distance at which both the respective first and second acceleration sensors 1895A, 1895B are positioned in the patients' body 1892 in a manner in which they both experience substantially the same noise (N) which is substantially the same.

In view of this arrangement, the second signal sensed via the second acceleration sensor 6364B (which senses noise without respiratory information) can be subtracted from the first signal sensed via first acceleration sensor 6364B (which senses both respiration and noise) to produce an effective signal which represents sensed respiratory information without the noise N common to both regions 6310, 6313 of the patient's body.

Figure 24F:
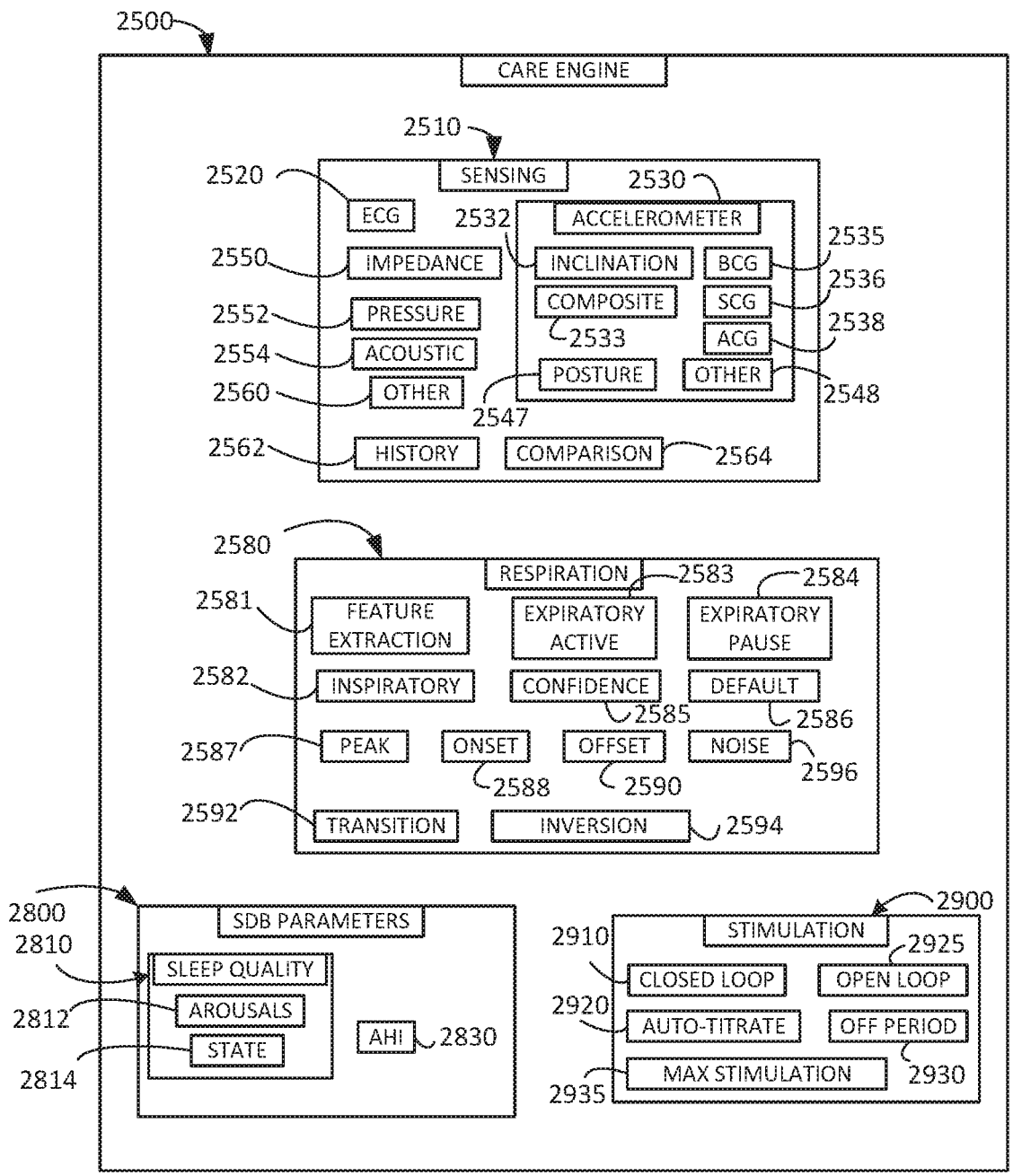
FIG. 24F is a block diagram schematically representing an example care engine.

In some such examples, the sensing arrangement described in association with FIG. 18A may comprise one example implementation of subtracting or other neutralizing noise according to the noise model parameter 2470 in FIG. 24E, the noise model 2596 in FIG. 24F, example method 5520 in FIG. 37A, and/or example method 5555 in FIG. 37B. In this way, more accurate and effective detection of respiratory information may be obtained.

Figure 18B:
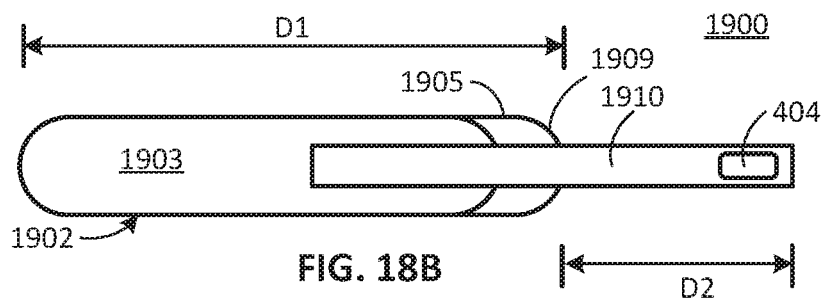
FIG. 18B is a diagram including a top view schematically representing an example implantable pulse generator including a lead comprising an accelerometer.

FIG. 18B is a diagram 1900 including a top view schematically representing an example implantable device 1902. In some examples, device 1902 may comprise at least some of substantially the same sensing elements (e.g. 122A), devices (e.g. 602) and related example methods as previously described in association with FIG. 1-18A, except comprising placement of the acceleration-based sensor 404 externally to the housing 1905 of the implantable device 1902. In some such examples, the sensor 404 may comprise a portion of a lead 1910 which is coupled (e.g. electrically and mechanically) relative e of substantially the same features and attributes as the sensors (e.g. 404 to the implantable device 1902 via a feedthrough portion 1903. In some examples, the lead 1910 (including sensor 404) may extend a distance D2 from edge 1909 of housing 1905, which is about the same as or less than a greatest dimension (e.g. D1) of the housing 1905. Via this example arrangement, the sensor 404 (e.g. accelerometer and/or other) may be located externally from the housing 1905 of device 1902 yet still be close enough to the housing 1905 such that both the lead 1910 (including sensor 404) and the device 1902 may be implanted within a single (e.g. same) subcutaneous pocket, such as (but not limited to) a pocket within the pectoral region.

However, in some examples, the lead 1910 may be longer than distance D2 and be placed subcutaneously via tunneling such that the lead 1910 (and sensor 404) extends beyond a subcutaneous pocket in which the device 1902 is implanted.

Figure 19:
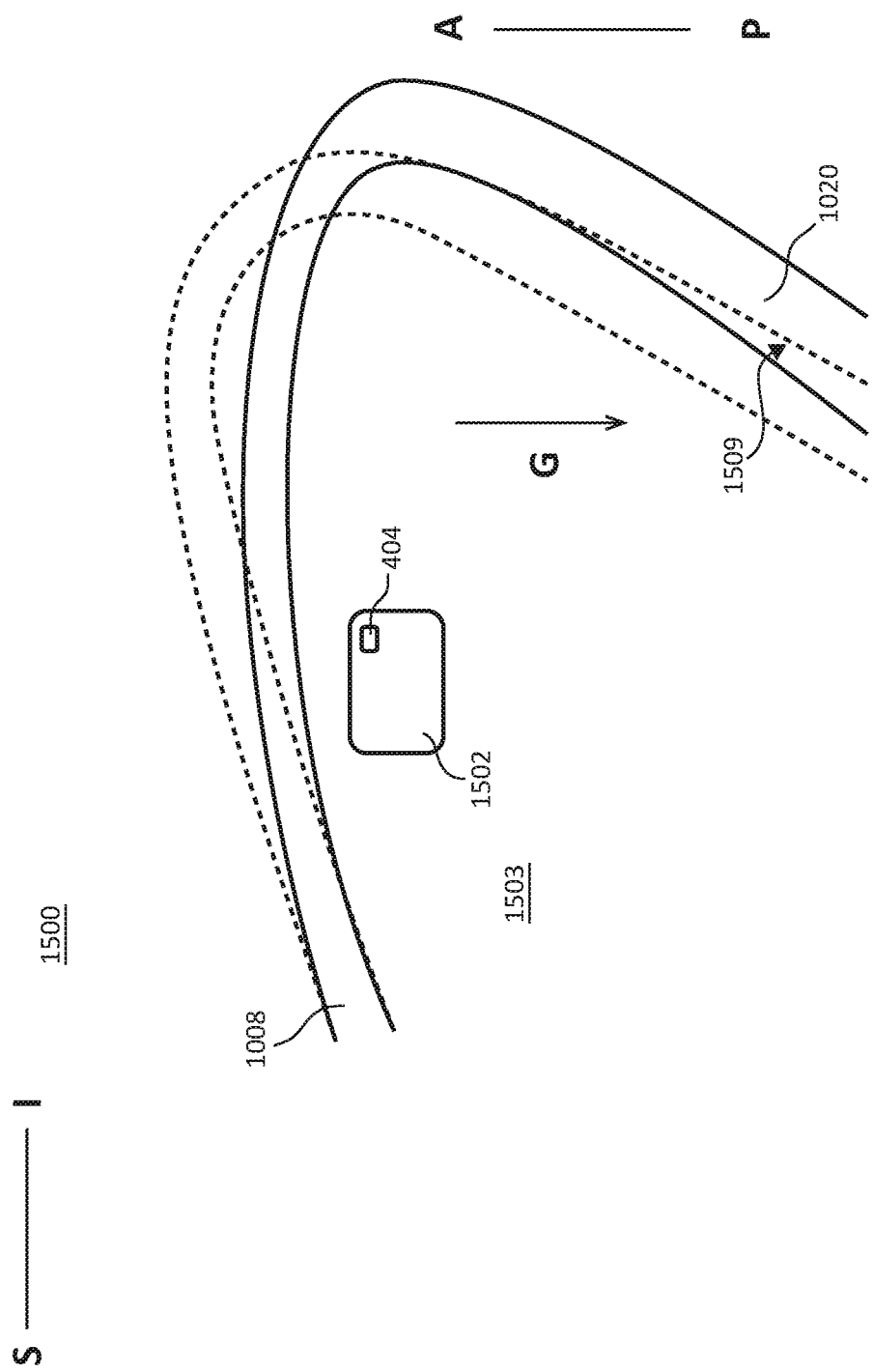
FIGS. 19 and 20 are each a diagram including a side view of a patient's chest and which schematically represents an example method of determining respiration information based on sensing rotational movement of the chest, via a sensor mounted on a side of the chest.

As described in association with FIGS. 19-22, in some examples an implantable device 1502 may be implanted on a side portion of the patient's rib cage and used in an example method to detect respiration information. In some examples, the example device 1502 and/or example method may comprise at least some of substantially the same features and attributes as the sensors (e.g. 404), sensing elements (e.g. 122A), devices (e.g. 602) and related example methods as previously described in association with FIG. 1-18B, except for at least device 1502 being implanted on the side portion 1503 of the patient's rib cage 1509 as shown in FIG. 19. Among other attributes, placement of device 1502 on a side portion 1503 of the patient's rib cage 1509 may enhance sensing a bucket-handle-type rotational movement of the rib cage during breathing (as represented via directional arrow BH in FIGS. 20-22), which may result in a significant change in an inclination angle measurable via an acceleration sensing element 611 having a primary orientation in lateral-medial orientation (L-M) of the rib cage. In some examples, such example arrangements may be particularly useful in an example method such as FIGS. 6A-6C and 7 in which an x-axis orientation acceleration sensing element has a measurement axis aligned generally parallel to a lateral-medial orientation (L-M) of the rib cage, and the patient's body is in a fully vertically upright position (FIG. 7) or a partially vertically upright position (FIG. 6A).

Figure 21:
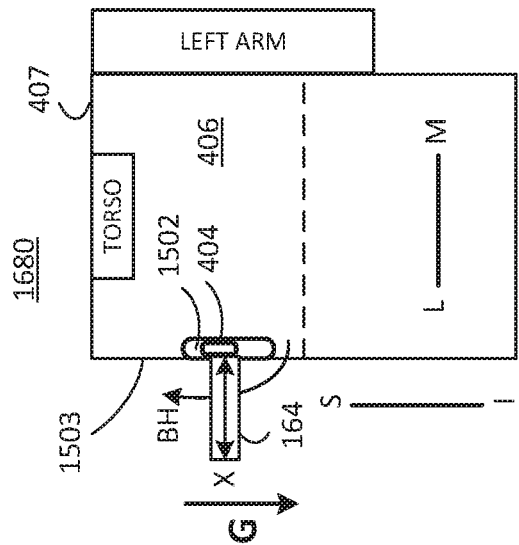
FIG. 21 is a diagram including a front view schematically representing an example method of sensing respiration via a sensor on a side portion of a patient's chest.
Figure 22:
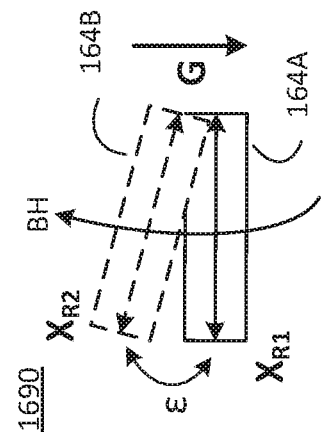
FIG. 22 is a diagram schematically representing an example method of determining respiration information via sensing rotation of a sensing element in relation to rotation of a side of a patient's chest.
Figure 20:
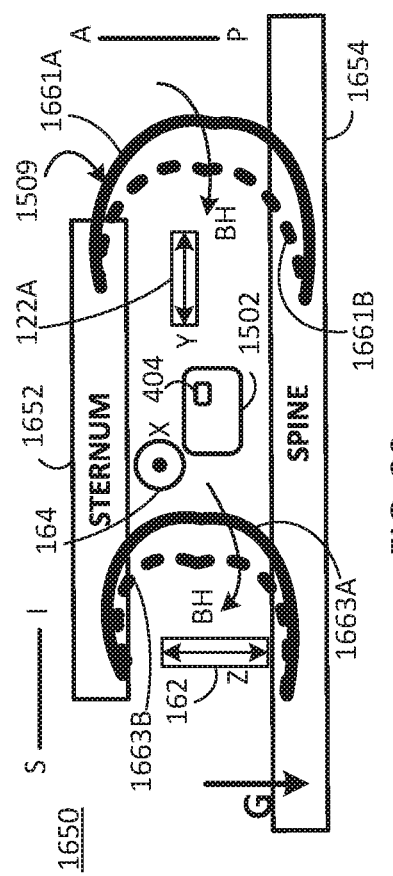

FIG. 20 is a diagram including a side view schematically representing an example device 1502 (FIG. 19-20) mounted on a side portion 1503 (e.g. lateral portion) of a patient's rib cage 1509. As shown in FIG. 21, during breathing example ribs 1661A, 1663A (shown in solid lines) rotationally move from a first position (e.g. peak expiration) to a second position 1661B, 1663B (shown in dashed lines) corresponding to peak inspiration, as represented via directional arrow BH. As further shown in FIG. 20, the example ribs 1661A, 1663A extend in a curved manner between a sternum 1652 at a front of the rib cage 1509 (e.g. chest) and a spine 1654 at a back or rear of the rib cage 1509. As previously noted, in some sleeping positions the particular implant location may position at least some of the acceleration sensing elements (e.g. along a lateral-medial (L-M) orientation) to enhance sensing respiration information, including respiration morphology.

It will be understood that the ribs will return from their position (dashed lines1661B, 1663B) at peak inspiration to the position shown in solid lines 1661A, 1663A corresponding to peak expiration, as the patient's respiratory cycle repeats cycles of inspiration followed by expiration.

FIG. 21 is a diagram 1680 including a front view schematically representing the example device 1502 of FIGS. 19-20 implanted along a side portion 1503 of the patient's ribcage 1509 and illustrating an orientation of rotational movement, according to a bucket-handle-type of motion (arrow BH) along the side portion 1503 of the rib cage 1509 during breathing. In some examples, as previously mentioned and as shown in FIG. 21, at least an X-axis acceleration sensing element 611 of sensor 404 of device 1502 may extend generally perpendicular to such bucket-handle-type (BH) of rotational movement of the side portion 1503 of rib-cage 1509.

As further shown in FIG. 21, in situations in which the patient may be sleeping in a partially upright position (FIG. 6) or a fully upright position (FIG. 7) and sleeping, the x-axis acceleration sensing element 164 (of a side-mounted device 1502 of FIGS. 19-21) may be the sensing element (of a three-axis accelerometer or of multiple accelerometers) which exhibits the highest sensitivity for an AC signal component in measuring an inclination angle of sensing elements during breathing. In some such example arrangements, as shown in the diagram 1690 of FIG. 22, the x-axis acceleration sensing element 611 may move between a first orientation XR1 (shown as 164A in solid lines) corresponding to peak expiration and a second orientation XR2 (shown as 164B in dashed lines) corresponding to peak inspiration in order to sense an inclination angle (E) through a range of motion during breathing, with the sensed signal being proportional to and representative of respiration morphology of the patient.

With further reference to FIGS. 19-22, in some examples, an implant location of an example device (e.g. 602 in FIG. 11, 1502 in FIGS. 19-21) may comprise a hybrid location on a front/top of chest and on a side of chest, such as front "corner" of the rib cage. In some such example arrangements, this "corner" implant location may capture some of both a bucket-handle-type rotational movement (side of rib cage) as in FIGS. 19-22 and a rise-fall-type rotational movement on front of chest as in FIGS. 1-18B.

It will be understood that in some example implementations, such rotational movement sensing (to determine respiration information) may be performed via sensing element(s) at both a front or top portion of a chest (e.g. FIG. 11) and a lateral portion of a chest (e.g. FIGS. 19-22), In some such examples, the rotational sensing information from both sensing locations may be combined to provide more robust and/or accurate respiration determination. However, some example methods and/or devices may use sensed rotational movement (caused by breathing) from just one of the sensing locations based on which sensing location produces the most robust and/or useful respiration information at a given point in time, and the particular sensing location (e.g. top/front portion or lateral portion) being used (to determine respiration information) at any particular point in time may vary.

Figure 23A:
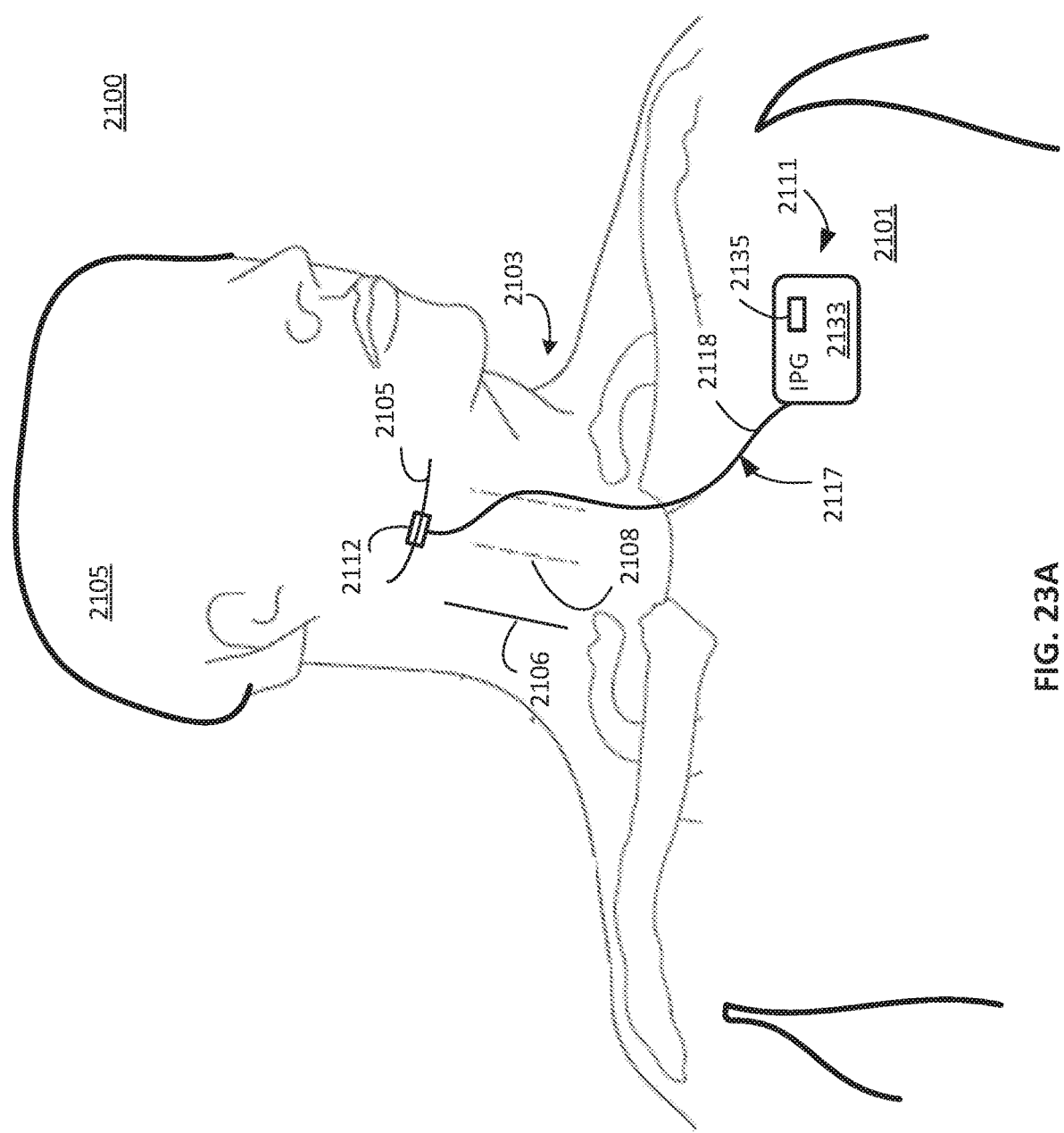
FIGS. 23A and 23B each are a diagram including a front view schematically representing an example method and/or example device including a medical device, including an accelerometer, implanted in a patient's chest.

FIG. 23A is a diagram including a front view of an example device 2111 (and/or example method) implanted within a patient's body 2100. In some examples, the device 2111 may comprise an implantable device 2133 such as (but not limited to) an implantable pulse generator (IPG) with device 2133 including a sensor 2135. In some examples, sensor 2135 may comprise a sensor (e.g. 104A, 122A, 162, 164, 204, 404, etc.) having at least some of substantially the same features and attributes as previously described in association with at least FIGS. 1-22. Via such example sensing arrangements, the device 2133 may determine respiration information via sensing rotational movement of the patient's chest wall during breathing, such as but not limited to when in a sleeping body position during a treatment period.

As further shown in FIG. 23A, device 2111 comprises a lead 2117 including a lead body 2118 for chronic subcutaneous implantation (e.g. via tunneling) and to extend to a position adjacent a nerve (e.g. hypoglossal nerve 2105 and/or phrenic nerve 2106). The lead 2117 may comprise a stimulation electrode to engage the nerve (e.g. 2105, 2106) for stimulating the nerve to treat a physiologic condition, such as sleep disordered breathing like obstructive sleep apnea, central sleep apnea, multiple-type sleep apneas, etc. The device 2133 may comprise circuitry, power element, etc. to support control and operation of both the sensor 2135 and the stimulation electrode 2112 (via lead 2117). In some examples, such control, operation, etc. may be implemented, at least in part, via a control portion (and related functions, portions, elements, engines, parameters, etc.) such as described later in association with at least FIGS. 24A-27.

With regard to the various examples of the present disclosure, in some examples, delivering stimulation to an upper airway patency nerve 2105 (e.g. a hypoglossal nerve) via the stimulation electrode 2112 is to cause contraction of upper airway patency-related muscles, which may cause or maintain opening of the upper airway (2108) to prevent and/or treat obstructive sleep apnea. Similarly, such electrical stimulation may be applied to a phrenic nerve 2106 via the stimulation electrode 2112 to cause contraction of the diaphragm as part of preventing or treating at least central sleep apnea. It will be further understood that some example methods may comprise treating both obstructive sleep apnea and central sleep apnea, such as but not limited to, instances of multiple-type sleep apnea in which both types of sleep apnea may be present at least some of the time. In some such instances, separate stimulation leads 2117 may be provided or a single stimulation lead 2117 may be provided but with a bifurcated distal portion with each separate distal portion extending to a respective one of the hypoglossal nerve 2105 and the phrenic nerve 2106.

In some such examples, the contraction of the hypoglossal nerve and/or contraction of the phrenic nerve caused by electrical stimulation comprises a suprathreshold stimulation, which is in contrast to a subthreshold stimulation (e.g. mere tone) of such muscles. In one aspect, a suprathreshold intensity level corresponds to a stimulation energy greater than the nerve excitation threshold, such that the suprathreshold stimulation may provide for higher degrees (e.g. maximum, other) upper-airway clearance (i.e. patency) and sleep apnea therapy efficacy.

In some examples, a target intensity level of stimulation energy is selected, determined, implemented, etc. without regard to intentionally establishing a discomfort threshold of the patient (such as in response to such stimulation). Stated differently, in at least some examples, a target intensity level of stimulation may be implemented to provide the desired efficacious therapeutic effect in reducing sleep disordered breathing (SDB) without attempting to adjust or increase the target intensity level according to (or relative to) a discomfort threshold.

In some examples, the treatment period (during which stimulation may be applied at least part of the time) may comprise a period of time beginning with the patient turning on the therapy device and ending with the patient turning off the device. In some examples, the treatment period may comprise a selectable, predetermined start time (e.g. 10 p.m.) and selectable, predetermined stop time (e.g. 6 a.m.). In some examples, the treatment period may comprise a period of time between an auto-detected initiation of sleep and auto-detected awake-from-sleep time. With this in mind, the treatment period corresponds to a period during which a patient is sleeping such that the stimulation of the upper airway patency-related nerve and/or central sleep apnea-related nerve is generally not perceived by the patient and so that the stimulation coincides with the patient behavior (e.g. sleeping) during which the sleep disordered breathing behavior (e.g. central or obstructive sleep apnea) would be expected to occur.

In some examples the initiation or termination of the treatment period may be implemented automatically based on sensed sleep state information, which in turn may comprise sleep stage information.

To avoid enabling stimulation prior to the patient falling asleep, in some examples stimulation can be enabled after expiration of a timer started by the patient (to enable therapy with a remote control), or enabled automatically via sleep stage detection. To avoid continuing stimulation after the patient wakes, stimulation can be disabled by the patient using a remote control, or automatically via sleep stage detection. Accordingly, in at least some examples, these periods may be considered to be outside of the treatment period or may be considered as a startup portion and wind down portion, respectively, of a treatment period.

In some examples, stimulation of an upper airway patency-related nerve may be performed via open loop stimulation. In some examples, the open loop stimulation may refer to performing stimulation without use of any sensory feedback of any kind relative to the stimulation.

In some examples, the open loop stimulation may refer to stimulation performed without use of sensory feedback by which timing of the stimulation (e.g. synchronization) would otherwise be determined relative to respiratory information (e.g. respiratory cycles). However, in some such examples, some sensory feedback may be utilized to determine, in general, whether the patient should receive stimulation based on a severity of sleep apnea behavior.

Conversely, in some examples and as previously described in relation to at least several examples, stimulation of an upper airway patency-related nerve may be performed via closed loop stimulation. In some examples, the closed loop stimulation may refer to performing stimulation at least partially based on sensory feedback regarding parameters of the stimulation and/or effects of the stimulation.

In some examples, the closed loop stimulation may refer to stimulation performed via use of sensory feedback by which timing of the stimulation (e.g. synchronization) is determined relative to respiratory information, such as but not limited to respiratory cycle information, which may comprise onset, offset, duration, magnitude, morphology, etc. of various features of the respiratory cycles, including but not limited to the inspiratory phase, expiratory active phase, etc. In some examples, the respiration information excludes (i.e. is without) tracking a respiratory volume and/or respiratory rate. In some examples, stimulation based on such synchronization may be delivered throughout a treatment period or throughout substantially the entire treatment period. In some examples, such stimulation may be delivered just during a portion or portions of a treatment period.

In some examples of "synchronization", synchronization of the stimulation relative to the inspiratory phase may extend to a pre-inspiratory period and/or a post-inspiratory phase. For instance, in some such examples, a beginning of the synchronization may occur at a point in each respiratory cycle which is just prior to an onset of the inspiratory phase. In some examples, this point may be about 200 milliseconds, or 300 milliseconds prior to an onset of the inspiratory phase.

In some examples in which the stimulation is synchronous with at least a portion of the inspiratory phase, the upper airway muscles are contracted via the stimulation to ensure they are open at the time the respiratory drive controlled by the central nervous system initiates an inspiration (inhalation). In some such examples, in combination with the stimulation occurring during the inspiratory phase, example implementation of the above-noted pre-inspiratory stimulation helps to ensure that the upper airway is open before the negative pressure of inspiration within the respiratory system is applied via the diaphragm of the patient's body. In one aspect, this example arrangement may minimize the chance of constriction or collapse of the upper airway, which might otherwise occur if flow of the upper airway flow were too limited prior to the full force of inspiration occurring.

In some such examples, the stimulation of the upper airway patency-related nerve may be synchronized to occur with at least a portion of the expiratory period.

With regard to at least the methods of treating sleep apnea as previously described in association with at least FIGS. 1-22, at least some such methods may comprise performing the delivery of stimulation to the upper airway patency-related first nerve without synchronizing such stimulation relative to a portion of a respiratory cycle. In some instances, such methods may sometimes be referred to as the previously described open loop stimulation.

In some examples, the term "without synchronizing" may refer to performing the stimulation independently of timing of a respiratory cycle. In some examples, the term "without synchronizing" may refer to performing the stimulation while being aware of respiratory information but without necessarily triggering the initiation of stimulation relative to a specific portion of a respiratory cycle or without causing the stimulation to coincide with a specific portion (e.g. inspiratory phase) of respiratory cycle.

In some examples, in this context the term "without synchronizing" may refer to performing stimulation upon the detection of sleep disordered breathing behavior (e.g. obstructive sleep apnea events) but without necessarily triggering the initiation of stimulation relative to a specific portion of a respiratory cycle or without causing the stimulation to coincide with the inspiratory phase. At least some such examples may be described in Wagner et al., STIMULATION FOR TREATING SLEEP DISORDERED BREATHING, published as US 2018/0117316 on May 3, 2018, and which is incorporated by reference herein in its entirety.

In some examples, while open loop stimulation may be performed continuously without regard to timing of respiratory information (e.g. inspiratory phase, expiratory phase, etc.) such an example method and/or system may still comprise sensing respiration information for diagnostic data and/or to determine whether (and by how much) the continuous stimulation should be adjusted. For instance, via such respiratory sensing, it may be determined that the number of sleep disordered breathing (SDB) events are too numerous (e.g. an elevated AHI) and therefore the intensity (e.g. amplitude, frequency, pulse width, etc.) of the continuous stimulation should be increased or that the SDB events are relative low such that the intensity of the continuous stimulation can be decreased while still providing therapeutic stimulation. It will be understood that via such respiratory sensing, other SDB-related information may be determined which may be used for diagnostic purposes and/or used to determine adjustments to an intensity of stimulation, initiating stimulation, and/or terminating stimulation to treat sleep disordered breathing. It will be further understood that such "continuous" stimulation may be implemented via selectable duty cycles, train of stimulation pulses, selective activation of different combinations of electrodes, etc.

In some examples of open loop stimulation or closed loop stimulation, some sensory feedback may be utilized to determine, in general, whether the patient should receive stimulation based on a severity of sleep apnea behavior. In other words, upon sensing that a certain number of sleep apnea events are occurring, the device may implement stimulation.

Some non-limiting examples of such devices and methods to recognize and detect the various features and patterns associated with respiratory effort and flow limitations include, but are not limited to: Christopherson et al., U.S. Pat. No. 8,938,299, SYSTEM FOR TREATING SLEEP DISORDERED BREATHING, issued Jan. 20, 2015; Christopherson et al., U.S. Pat. No. 5,944,680, titled RESPIRATORY EFFORT DETECTION METHOD AND APPARATUS; and Testerman U.S. Pat. No. 5,522,862, titled

METHOD AND APPARATUS FOR TREATING OBSTRUCTIVE SLEEP APNEA.

Moreover, in some examples various stimulation methods may be applied to treat obstructive sleep apnea, which include but are not limited to: Ni et al., SYSTEM FOR SELECTING A STIMULATION PROTOCOL BASED ON SENSED RESPIRATORY EFFORT, which issued as U.S. Pat. No. 10,583,297 on 3/10/2020; Christopherson et al. U.S. Pat. No. 8,938,299, SYSTEM FOR TREATING SLEEP DISORDERED BREATHING, issued Jan. 20, 2015; and Wagner et al., STIMULATION FOR TREATING SLEEP DISORDERED BREATHING, published as US 2018/0117316 on May 3, 2018, each of which is hereby incorporated by reference herein in its entirety.

In some examples, the example stimulation element(s) 2112 shown in FIG. 23A may comprise at least some of substantially the same features and attributes as described in Bonde et al. U.S. Pat. No. 8,340,785, SELF EXPANDING ELECTRODE CUFF, issued on Dec. 25, 2102 and Bonde et al. U.S. Pat. No. 9,227,053, SELF EXPANDING ELECTRODE CUFF, issued on Jan. 5, 2016, Johnson et al. U.S. Pat. No. 8,934,992, NERVE CUFF issued on Jan. 13, 2015, and Rondoni et al. CUFF ELECTRODE, WO 2019/032890 published on Feb. 14, 2019, and filed as U.S. application Ser. No. 16/485,954 on Aug. 14, 2019, each which are incorporated by reference herein in their entirety. Moreover, in some examples a stimulation lead 2117, which may comprise one example implementation of a stimulation element, may comprise at least some of substantially the same features and attributes as the stimulation lead described in U.S. Pat. No. 6,572,543 to Christopherson et al., and which is incorporated by reference herein in its entirety.

In some examples, the stimulation electrode 2112 may be delivered transvenously, percutaneously, etc. In some such examples, a transvenous approach may comprise at least some of substantially the same features and attributes as described in Ni et al., Transvenous Method of Treating Sleep Apnea, issued as U.S. Pat. No. 9,889,299 on Feb. 13, 2018, and which is hereby incorporated by reference. In some such examples, a percutaneous approach may comprise at least some of substantially the same features and attributes as described in Christopherson et al., Percutaneous Access For Systems and Methods Of Treating Sleep Apnea, issued as U.S. Pat. No. 9,486,628 on Nov. 8, 2016, and which is hereby incorporated by reference.

Figure 23B:
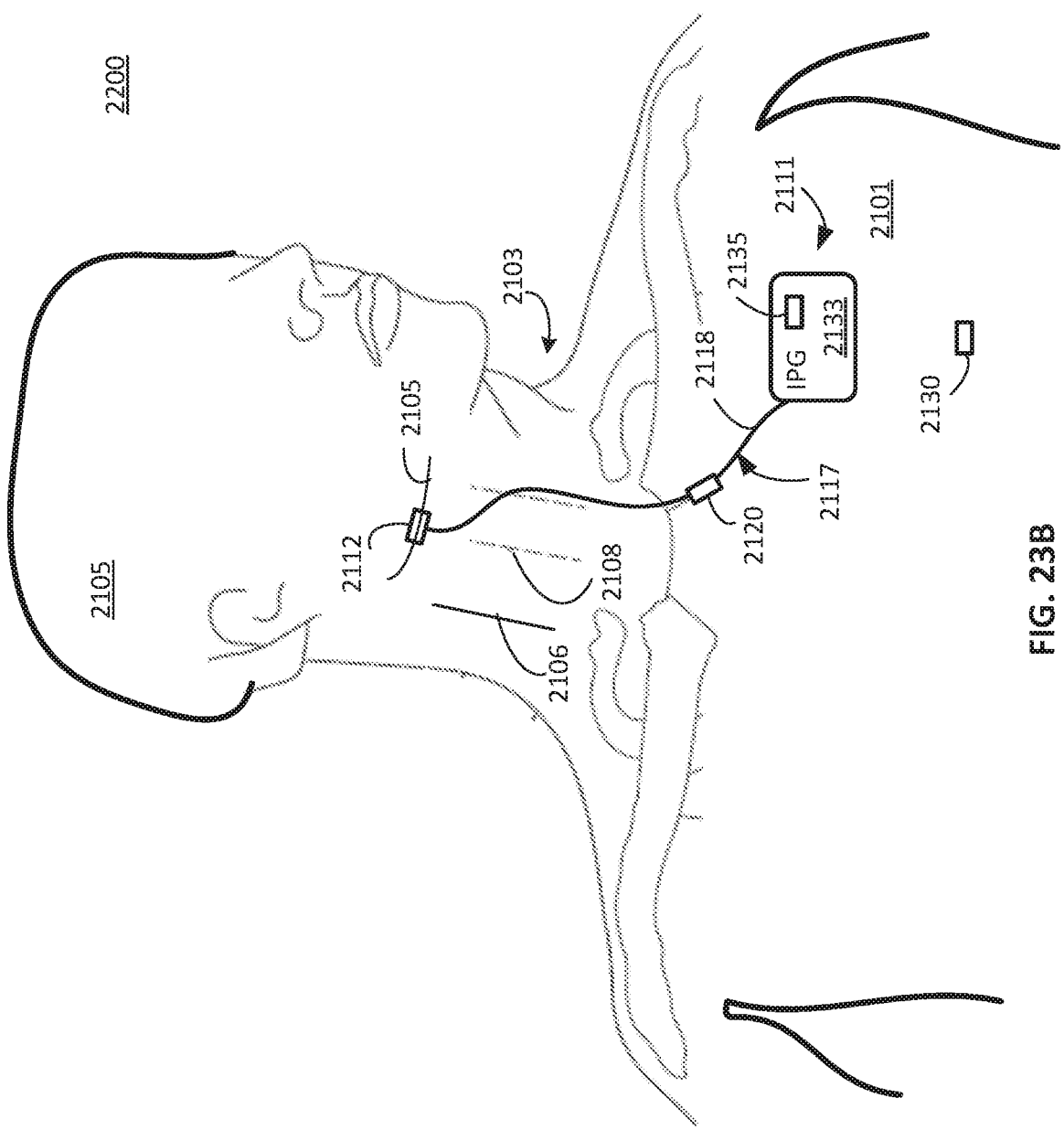

As shown in the diagram of FIG. 23B, in some examples device 2111 (FIG. 23A) may be implemented with additional sensors 2120, 2130, etc. to sense additional physiologic information, such as but not limited to, further respiratory information via sensing transthoracic bio-impedance, pressure sensing, etc. in order to complement the respiration information sensed via acceleration sensor 2135 (FIG. 23A). In some examples, one or both of the sensors 2120, 2130 may comprise sensor electrodes. In some examples, stimulation electrode 2112 also may act, in some examples, as a sensing electrode. In some examples, at least a portion of housing of the device 2133 also may comprise a sensor or at least an electrically conductive portion (e.g. electrode) to work in cooperation with sensing electrodes (e.g. 2120, 2130, and/or 2112) to implement at least some sensing arrangements to sense bioimpedance, ECG, etc.

Figure 23C:
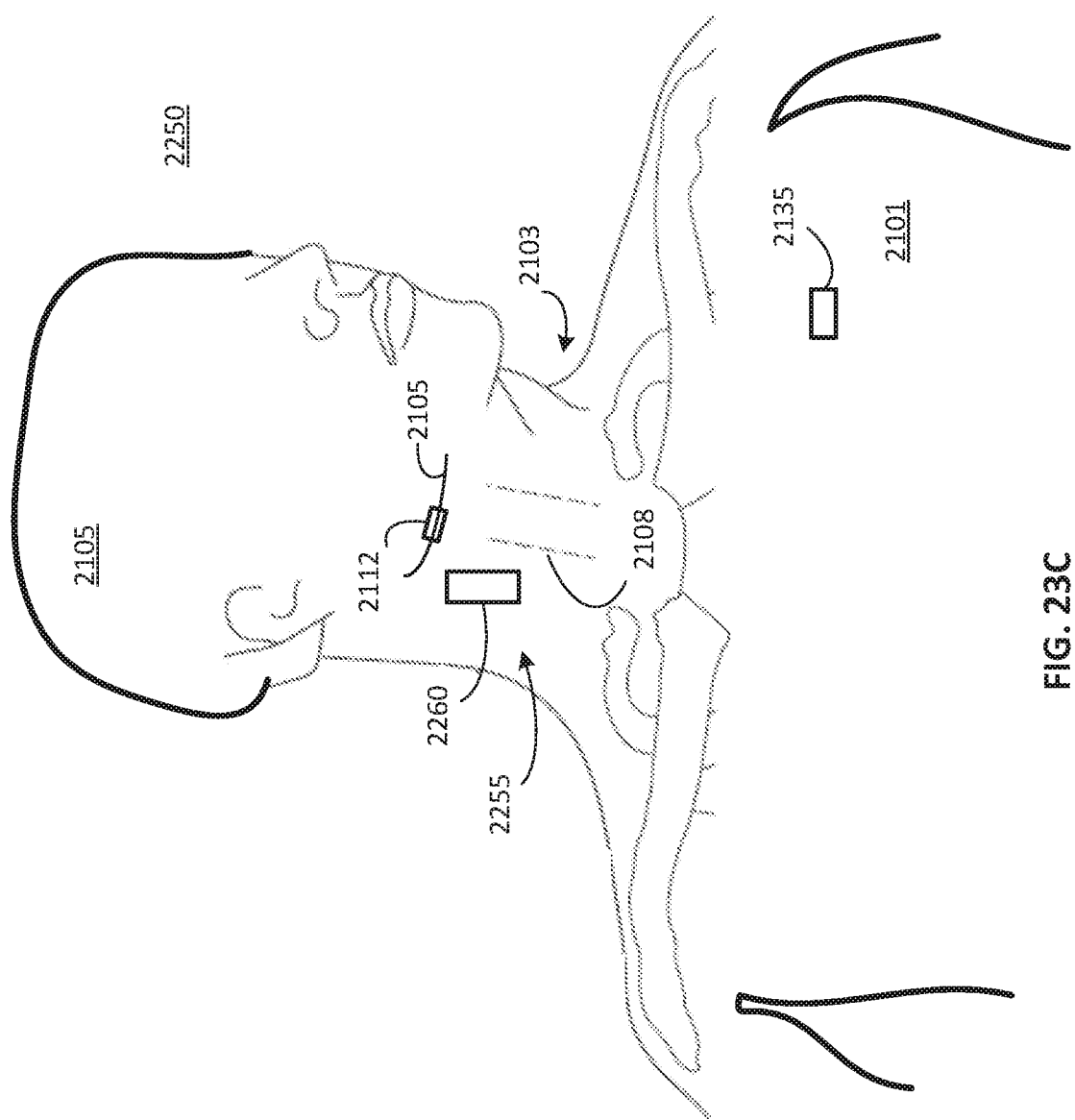
FIG. 23C is a diagram including a front view schematically representing an example method and/or example device including a microstimulator and an accelerometer implanted in a patient's chest to determine respiration information.

FIG. 23C is a diagram schematically representing an example treatment device 2255 comprising at least some of substantially the same features and attributes as the treatment device (and/or example method) 2811 in FIG. 23A or 23B, except with the IMD 2133 implemented as a microstimulator 2260. In some examples, the microstimulator 2260 may be chronically implanted (e.g. percutaneously, subcutaneously, transvenously, etc.) in a head-and-neck region 2103 as shown in FIG. 23C, or in a pectoral region 2101. In some examples, as part of the treatment device 2255, the microstimulator 2260 may be in wired or wireless communication with stimulation electrode 2112. In some examples, as part of the treatment device 2255, the microstimulator 2260 also may incorporate sensor 2135 or be in wireless or wired communication with a sensor 2135 located separately from a body of the microstimulator 2260. As noted in prior examples, the sensor 2135 may comprise an acceleration sensor and/or other type of sensor. When wireless communication is employed for sensing and/or stimulation, the microstimulator 2260 may be referred to as a leadless implantable medical device for purposes of sensing and/or stimulation. In some examples, the microstimulator 2260 may be in close proximity to a target nerve 2105.

In some examples, the microstimulator 2260 (and associated elements) and/or treatment device 2255 may comprise at least some of substantially the same features and attributes as described and illustrated in Rondoni et al, MICRO-STIMULATION SLEEP DISORDERED BREATHING (SDB) THERAPY DEVICE, published May 26, 2017 as WO 2017/087681, and filed as U.S. application Ser. No. 15/774,471 on May 8, 2018, both of which are incorporated by reference herein.

Moreover, with further reference to FIG. 24F, in some examples the above-mentioned electrocardiogram (ECG), as well as ballistocardiograph sensing (BCG) 2535, seismocardiograph sensing (SCG) 2536, and/or accelerocardiograph sensing (ACG) 2538 may be employed in combination with the sensing of acceleration-based inclination angles (based on rotational movement of the rib cage during breathing) described throughout the various, as noted in association with at least sensing portion 2510 of care engine 2500. In one aspect, the ECG, SCG, BCG, and/or ACG sensing may be used to perform sensing of Respiratory Sinus Arrhythmia (RSA) and by which respiration detection may be performed. In some such examples, the sensed RSA may be used to identify an inspiratory phase, expiratory active phase, and/or expiratory pause phase of a respiratory cycle and/or may be used to distinguish the respective phases from each other. In some such examples, such identifying and/or such distinguishing may be performed via the identifying an R-R interval to determine the sensed RSA, in which the R-R interval is shorter during inspiration and the R-R interval is faster during expiration.

FIG. 24A is a block diagram schematically representing example method 2300. In some examples, method 2300 may be implemented via at least some of the devices, sensors, sensing elements, etc. as previously described in association with FIGS. 1-23B. In some examples, the example method 2300 may be at least partially implemented within, and/or via, control portion 4000 in FIG. 25A, control portion 4020 in FIG. 25B, user interface 4040 in FIG. 26, care engine 2500 in FIG. 24F. In some such examples, the example method may be implemented as part of (and/or via) sensing portion 2510 and/or respiration portion 2580 of care engine 2500 in FIG. 24F.

As shown at 2310 in FIG. 24A, the example method 2300 comprises sensing acceleration signal(s) from a sensor(s) implanted within a patient's body in a position, such as in the chest region, to detect respiration information. In some examples, just a single sensing element (e.g. 122A in FIG. 2) may be used to provide just a single sensed acceleration signal or in some examples, multiple sensing elements may be used to provide separate multiple sensed acceleration signals. The multiple sensing elements may be separate from, and independent of, each other, or may be co-located as part of a single device, such as a three-axis accelerometer.

As further shown at 2314, filtering is applied separately to the sensed signal(s) (2310) to produce a respective separate inclination angle signal (2321X, 2321Y, 2321Z) for each corresponding acceleration signal (e.g. X-axis, Y-axis, Z-axis). It will be understood that if just one single-axis sensing element is employed, then just one inclination angle signal will be present at 2320. As previously described through various examples, the inclination angle signal represents the physiologic phenomenon of the patient's breathing with a value and/or shape of the inclination angle signal varying through the different phases of a respiratory cycle (e.g. inspiratory phase, expiratory active phase, expiratory pause phase) as the patient breathes. It will be further noted that while some examples may comprise tracking inclination angle signal for multiple axes (X, Y, Z), some example methods may focus on an axis which is closest to being generally perpendicular to the gravity vector.

In some examples, in addition to applying filtering (at 2314) as described above to produce a respective separate inclination angle signal (2321X, 2321Y, 2321Z) for each corresponding acceleration signal (e.g. X-axis, Y-axis, Z-axis), the filtering may further comprise subtracting (e.g. filtering, excluding) noise from the signal to increase the signal-to-noise ratio for the respiratory features of interest. In some examples, such noise filtering may be implemented as described later in association with noise model parameter 2470 in FIG. 24E. It will be understood that in some examples, such noise filtering may be applied in other ways and/or at other times within the example method (and/or arrangement) in FIG. 24A.

As further shown at 2340 in FIG. 24A, method 2300 comprises performing a feature extraction a signal-by-signal basis (2341X, 2341Y, 2341Z) to identify within each inclination angle signal (2321X, 2321Y, 2321Z) features indicative of respiration (and/or other features pertinent to respiratory detection, patient health, etc). As shown at 2350, in some examples the method identifies at least respiratory phase information including (but not limited to) the features of an inspiratory phase 2352, an expiratory active phase 2354, and an expiratory pause phase 2356. It will be understood that each feature (e.g. phase 2352, 2354, 2356) may comprise a start (i.e. onset), an end (e.g. offset), a duration, magnitude, and/or both a "start and end" of each respective feature. In some instance, a particular feature may be sometimes be referred to as a fiducial or similar terms, such as a start of a phase (e.g. inspiration) comprising a fiducial.

As shown at 2330, a confidence factor may be applied to each of the feature extraction elements (2341X, 2341Y, 2341Z), such as an X-axis confidence factor 2331X, Y-axis confidence factor 2331Y, and Z-axis confidence factor 2331Z. At least some aspects of applying a confidence factor are described later in association with at least FIG. 24B.

In some examples, upon performing feature extraction (2341X, 2341Y, 2341Z) of respiratory phase information to each inclination angle signal, the resulting extracted feature signals are combined (e.g. fused together) at 2345 to produce (i.e. determine) a composite sensed respiratory signal including respiratory phase information (2350) including inspiratory phase 2352, expiratory active phase 2354, and expiratory pause phase 2354. In some examples, the different extracted feature signals may be combined (e.g. fused) as an average of the respective features, a median of the respective features, or weighting (linear or non-linear) according to a confidence factor (e.g. 2331X, 2331Y, 2331Z). At least some aspects of the confidence factor(s) are described later in association with at least FIG. 24B. In some such examples, the composite sensed respiratory signal may correspond to the virtual vector as previously described in association with at least FIG. 5, composite parameter 2533 in FIG. 24F, and throughout various examples of the present disclosure.

As further shown in FIG. 24A, from the determined respiratory phases (2352, 2354, 2354), additional respiratory parameters 2360 may be determined. For example, an (overall) expiratory phase may comprise a sum or combination of the expiratory active phase (2354) and the expiratory pause phase (2356). In addition, a respiratory period may be determined from a sum of duration of the inspiratory phase 2352 and a duration of the (overall) expiratory phase, including both the active and pause phases 2354, 2356. Meanwhile, the respiratory rate (RR) may computed as 1/respiratory period. Additional parameters may comprise a computed I/E ratio, such as inspiratory phase duration ($T_I$ in FIG. 3) divided by an expiratory phase duration ($T_{EA}$ plus $T_{EP}$ in FIG. 3).

In some examples, assuming a given body position or posture and excluding translational motion along the axes (e.g. X, Y, Z), some additional parameters may be determined from the extracted features (including respiratory phase information at 2350) with such additional parameters comprising: an approximation of a tidal volume as being proportional to acceleration; an approximation of respiratory flow as being proportional to a derivative of the acceleration signal with respect to time; and/or an approximation of minute ventilation as being proportional to a result of a multiplication of the computed volume and the computed respiratory rate (described above).

In some examples, determinations relating to feature extraction (2340 in FIG. 24A) may further comprise the following parameters. For instance, in some examples of feature extraction, a signal midpoint may be determined, which comprises an average of previous "n" positive peak values and previous "n" negative peak values, where "n" is 1 or more. In some examples of feature extraction, a signal midpoint crossing may be determined, which comprises a sample at which the signal midpoint is crossed. In some examples, the signal midpoint crossing may involve hysteresis with a hysteresis threshold being determined by a fixed threshold, a fraction of recent "n" peak-to-peak values, a fraction of signal root-mean-square (RMS) value, and/or a dynamic threshold with linear decay or exponential decay. In some examples of feature extraction, a peak midpoint area may be determined which comprises an integral (e.g. sum) of all points from a previous signal midpoint crossing to a current signal midpoint crossing.

In some examples, determination of the expiratory active phase (2354 in FIG. 24A) is at least partially based on: (1) a detected peak following Peak-Midpoint Area above mean of "n" recent Peak-Midpoint Areas, wherein the expiratory pause phase 2356 creates a relatively larger Peak-Midpoint area, which allows determination of respiratory phase in a way that is insensitive to signal inversion; (2) an absolute value of a derivative (current sample minus previous sample) above a threshold; and/or (3) an absolute value of a derivative of the signal above a threshold for a time threshold.

In some examples, determination of the expiratory pause phase (2354 in FIG. 24A) is at least partially based on: (1) a previous phase detected as an expiratory active phase 2354; (2) an absolute value of derivative of the signal below a threshold; and/or (3) an absolute value of derivative of the signal below a threshold for a time threshold.

In some examples, determination of the inspiratory phase (2352 in FIG. 24A) is at least partially based on: (1) a previous phase detected as expiratory pause phase; (2) an absolute value of derivative of the signal above a threshold; and/or (3) an absolute value of derivative of the signal above a threshold for a time threshold.

With further reference to FIG. 24A, in some examples determining respiration information (via sensing acceleration signals to detect rotational movements of the ribcage during breathing), the example method 2300 may utilize default respiratory phase values as shown at 2390 instead of using the sensed acceleration signals 2310. For instance, in cases in which the sensed acceleration signal quality is poor (i.e. inadequate), the current respiratory phases of the patient may not be known from the current sensed acceleration signals or recent sensed acceleration signals. In some examples, the default respiratory phase values (2390) are assigned a confidence level or factor 2391, which may have a low value to ensure that extracted features (2341X, 2341Y, 2341Z) are used when the sensed acceleration signal quality is adequate. Accordingly, when the sensed acceleration signal is of sufficient quality as determined by the signal-to-noise ratio of the signal, then method 2300 may ignore the default respiratory phase values at 2390. The signal-to-noise ratio may be determined by a comparison with a typical signal morphology, a comparison with a typical signal frequency content, or by other means.

With further reference to the default respiratory phase values portion 2390 in FIG. 24A, in some examples the default respiratory phase values (2390) may be determined using at least one of the following: (1) mean respiratory phase time values of the overall human population; (2) the patient's historical or recent mean/median respiratory phase and/or phase time values; and (3) intentionally applying a longer respiratory rate or a shorter respiratory rate to decrease the chance that an appreciable number of consecutive stimulation "off" times may align with inspiration.

Accordingly, via the default respiratory phase values, some example methods may comprise substituting, upon the sensor obtaining an inadequate signal, stored respiratory information comprising historical respiration information for at least one of: the patient's respiratory cycle information; and multiple-patient respiratory cycle information. In some such examples, the patient's respiratory cycle information comprises a respiratory period, and an example method comprises: creating a modified respiratory period by adding a random time value to the respiratory period of the patient's respiratory cycle information; and implementing the substituting of the stored respiratory information using the modified respiratory period. In some examples, the random time value may comprise about 0 to about 1 second. In some examples, the random time value may comprise other time periods. In some examples, adding the random time value may cause a result similar that noted above (in regard to the default respiratory phase values) by which the example method may intentionally apply a longer respiratory rate or a shorter respiratory rate to decrease the chance that an appreciable number of consecutive stimulation "off" times may align with inspiration.

In some examples, the method may comprise substituting, upon the sensor obtaining an inadequate signal, stored respiratory information comprising respiratory cycle information including at least one of: a first respiratory rate substantially faster than the patient's average respiratory rate; and a second respiratory rate substantially slower than the patient's average respiratory rate. In some such examples, the terms substantially faster and/or substantially slower may correspond to a difference on the order of 5 percent difference, 10 percent difference, and the like.

FIG. 24B is a block diagram schematically representing an example confidence factor portion 2400, which may be employed at 2330 in example method 2300 and/or as part of (or via) control portion 4000 in FIG. 25A. It will be understood that all or just some of the factors (e.g. different combinations or a single factor) in confidence factor portion 2400 may be applied at 2330 in method 2300 in FIG. 24A. In some examples, a confidence factor may be implemented as an estimated probability of correctness.

As shown in FIG. 24B, in some examples confidence factor portion 2400 comprises a first factor portion 2410 comprising a signal-to-noise ratio parameter 2412, a threshold parameter 2414, and a recent history parameter 2416. Accordingly, in some examples, via signal-to-noise ratio information (parameter 2412), a confidence level may be determined for each extracted feature (at 2340 in FIG. 24A) and/or for each inclination angle signal (at 2320 in FIG. 24A). In some examples, at 2414 method 2300 comprises the confidence comprising an amount by which a value (e.g. of a feature, of the inclination signal, etc.) exceeds a threshold. Stated differently, if a value of the inclination signal such as for a particular axis (e.g. Y-axis in FIG. 2) exceeds a threshold by a significant amount, then the method can apply a high value confidence factor to the Y-axis feature extraction (2341Y in FIG. 24A) such that determination of the respiratory phase information (2350 in FIG. 24A) may depend primarily on the Y-axis inclination signal (2321Y in FIG. 24A) as compared to other axes (e.g. X or Z) inclination signals, if present. In some examples, the confidence factor may be applied per recent history parameter 2416 according to a difference between a current value of an extracted feature and a mean value of "n" recent extracted features.

In some examples, each of the confidence parameters in first factor portion 2410 may be applied quantitatively according to a look-up table, multiplication factor (e.g. 1.5, 2×, etc.), and the like.

In some examples, confidence factor portion 2400 may comprise a second factor portion 2420 by which confidence in a value of a particular extracted feature (2341X, 2341Y, 2341Z) may be increased or decreased based on posture (2422) at the time of sensing, heart rate (2424), and/or sleep stage (2426). As further shown in third factor portion 2430 of FIG. 24B, such confidence factors in second factor portion 2420 may be weighted and/or calibrated according to particular patient-based factors, such as patient preferences (e.g. feedback) 2432, clinician input 2434, and/or other information such sleep study information. Further parameters which may comprise part of second confidence factor portion 2420 may include sensed body temperature, time of day, etc.

In some examples, the various parameters, etc. of the respective first, second, and third portions of confidence factor portion 2400 may be used together in different combinations and/or organized in different groupings (or no groupings) than shown in FIG. 24B.

FIG. 24C is a block diagram schematically representing an example feature extraction portion 2450, which may comprise functions, settings, etc. which may act as part of the implementation of the feature extraction at 2340 in method 2300 of FIG. 24A. As shown via parameter 2452 at 2450 in FIG. 24C, in some examples a threshold factor may be applied by a user or clinician to adjust thresholds used in performing feature extraction of the inspiratory phase 2352 (e.g. inhalation threshold), of the expiratory active phase 2354 (e.g. exhalation threshold), and/or of the expiratory pause phase 2356 (e.g. exhalation threshold). As shown via parameter 2454 at 2450 in FIG. 24C, in some examples a sensitivity factor may be applied by a user or clinician to adjust thresholds used in performing feature extraction of the inspiratory phase 2352 (e.g. inhalation sensitivity), of the expiratory active phase 2354 (e.g. exhalation sensitivity), and/or of the expiratory pause phase 2356 (e.g. exhalation sensitivity). In some examples, the sensitivity factor may comprise an invert function to adjust thresholds using in a peak-midpoint calculation of the expiratory active phase 2354.

In some examples, in determining the respiratory phase information (2390) example method 2300 also may comprise predicting an inspiratory phase (e.g. 2352 in FIG. 24A), as shown at 2460 in FIG. 24D. The prediction of the inspiratory phase may be used to increase a likelihood of implementing actions (e.g. start of stimulation, etc.) which are to be synchronized with a start of the inspiratory phase 2352. Stated differently, predicting the inspiratory phase 2352 as at 2460 in FIG. 24D may decrease a chance that detection of a start of the inspiratory phase might be missed. Moreover, in some example methods and/or example devices, electrical stimulation of a nerve (e.g. hypoglossal nerve) may be initiated prior to a start of inspiration to ensure that the upper airway is open prior to the pressure applied on the upper airway once the actual inspiratory phase commences. In addition, starting electrical stimulation prior to the actual inspiratory phase also may provide some assurance in cases in which prediction of the inspiratory phase may be incorrect or may experience an insufficient signal-to-noise ratio. In some such examples, example methods and/or devices may initiate the stimulation a predetermined period of time prior to an onset of the inspiratory phase. In some examples, the predetermined period of time has a duration less than a duration of the expiratory pause according to an average duration of an expiratory pause phase, according to a duration of the preceding expiratory pause phase, etc. In some examples, the predetermined period of time may comprise an absolute amount of time (e.g. start 0.5 seconds) and in some examples, the predetermined period of time may comprise a relative amount of time, such as 10% of the preceding respiratory period. As mentioned in association with other examples regarding synchronization, in some examples the predetermined period of time may be about 200 milliseconds, or 300 milliseconds.

In some examples, the inspiratory phase prediction function (2460) in FIG. 24D may comprise predicting a start of the inspiratory phase via timing based on: (1) an expiratory active phase 2354 of the most recent (e.g. immediately preceding) respiratory cycle; (2) an expiratory pause phase 2356 of the most recent (e.g. immediately preceding) respiratory cycle; and/or (3) an inspiratory phase of one or more previous respiratory cycles and/or the respiratory rate of one or more previous respiratory cycles. In some examples, in determining the timing (of the inspiratory phase and/or respiratory rate of previous respiratory cycles), the method may utilize a mean value, a median value, linear extrapolation, and/or non-linear extrapolation of the respective inspiratory phase or respiratory rate.

With further reference to inspiratory phase prediction 2460 in FIG. 24D, in some examples, determining the timing (of the inspiratory phase and/or respiratory rate of previous respiratory cycles), the use of values from previous respiratory cycles may also enhance an accuracy of feature extraction (2340 in FIG. 24A). For instance, accuracy of timing peak detection may be enhanced by using data before and after the peak. In another instance, using values from previous respiratory cycles may make an example method (of detecting respiration) less susceptible to a noisy signal during a particular respiratory cycle, patient limb movements, bed partner movements, etc.

In some examples, a method may increase accuracy of determining respiration from a sensed acceleration signal (of rotational movement at a portion of a chest wall) by removing noise from the sensed signal according to a noise model, which is shown in association with at least noise model parameter 2470 in FIG. 24E.

In some such examples, the method comprises constructing the noise model from identifying characteristics (e.g. signal morphology, frequency content, etc.) within the sensed signal which are caused by and/or associated with conditions, phenomenon, etc. other than respiration-related behavior of the patient (and/or cardiac-related behavior, etc.) and which are considered noise relative to the signal of interest regarding patient respiration. In just one example, one source of noise (which may form at least part of a noise model) may comprise movement, behavior, etc. from another person (i.e. partner) sleeping in the same bed, which may be picked up by the sensed signal for the patient. In some instances, such motion may sometimes be referred to as non-patient-physiologic motion. Other sources of noise, which form at least part of a noise model, may comprise additional/other non-patient-physiologic motion, such as but not limited to motion of a vehicle in which the patient is present such as when the patient is traveling a car, airplane, spaceship, etc. Other types of non-patient-physiologic motion which may be considered as noise (and which form at least part of a noise model) may comprise movement of a patient support surface, such as a hammock, swings, etc. Another type of noise, which may form at least part of the noise model, may comprise a physical position of the patient such as being in a very tall building in motion due to wind, a location experiencing vibration or movement such that the motion of the patient may affect the sensed acceleration signal and otherwise hinder accurate determination of respiration information per the type of rotational sensing in the examples of the present disclosure.

By constructing a noise model from these non-patient characteristics, and subtracting the noise model from the sensed acceleration signal of the patient, a more accurate sensed respiration signal may be determined. In some instances, the subtraction may be performed by filtering the noise and/or by excluding sensor element signals including such noise.

In some examples, such noise may be filtered or excluded from the sensed acceleration signals (of rotational movement of a respiratory body portion, such as a chest wall) without use of a formal noise model.

In some examples, at least some of the features and attributes of use of a noise model, which may increase a signal-to-noise ratio of the signal of interest (respiration information), may be implemented at least partially within or via filtering 2314 in method 2300 as shown in FIG. 24A.

In some examples, the prediction of the inspiratory phase (e.g. 2460 in FIG. 24D) also may be performed according to cross-referencing (e.g. similarity) the inspiratory phase of a previous respiratory cycle relative to stored reference morphology of the inspiratory phase.

FIG. 24F is a block diagram schematically representing an example care engine 2500. In some examples, the care engine 2500 may form part of a control portion 4000, as later described in association with at least FIG. 25A, such as but not limited to comprising at least part of the instructions 4011 and/or information 4012. In some examples, the care engine 2500 may be used to implement at least some of the various example devices and/or example methods of the present disclosure as previously described in association with FIGS. 1-23B and/or as later described in association with FIGS. 25A-46. In some examples, the care engine 2500 (FIG. 24F) and/or control portion 4000 (FIG. 25A) may form part of, and/or be in communication with, a pulse generator (e.g. 2133 in FIG. 23A-23B).

As shown in FIG. 24, in some examples the care engine 2500 comprises a sensing portion 2510, a respiration portion 2580, a sleep disordered breathing (SDB) parameters portion 2600, and/or a stimulation portion 2900.

In one aspect, at least the sensing portion 2510 of care engine 2500 in FIG. 24 directs the sensing of information, and/or receives, tracks, and/or evaluates sensed information obtained via one or more of the sensors, sensing elements, sensing modalities, etc. as previously described in association with at least FIGS. 1-24D, with care engine 2500 employing such information to determine respiration information, among other actions, functions, etc. as further described below.

In some examples, the sensing portion 2510 may comprise an ECG parameter 2520 to direct ECG sensing, obtain sensed ECG information, etc. to obtain cardiac information and/or some respiration information, which may be used together with respiration information determined via sensing according to the examples in FIGS. 1-24D and 25A-46. In some examples, the ECG information is sensed via at least some of the sensing electrodes (e.g. 2112, 2120, 2130, etc.) as previously described in association with at least FIG. 23B.

In some examples, the sensing portion 2510 may comprise an accelerometer portion 2530. In some examples, the accelerometer portion 2530 directs acceleration-based sensing, obtains/receives acceleration signal information, etc. to obtain at least respiration information and/or other information (cardiac, posture, etc.). In some examples, such acceleration sensing may be implemented according to at least some of substantially the same features and attributes as described in Dieken et al., ACCELEROMETER-BASED SENSING FOR SLEEP DISORDERED BREATHING (SDB) CARE, published as U.S. 2019-0160282 on May 30, 2019, and which is incorporated by reference herein in its entirety.

In some examples, the acceleration sensing may be used to determine and/or receive inclination information (parameter 2532 in FIG. 24F), such as the changes in inclination angle of the acceleration sensing elements, which is indicative of rotational movement of the patient's chest wall, which in turn provides respiration information, as extensively described throughout examples of the present disclosure. As noted elsewhere, sensing of rotational movement (to determine respiration information) is not limited solely to the chest (e.g. chest wall) but may comprise other or additional respiratory body portions, such as but not limited to the abdomen (e.g. abdominal wall).

As represented via composite parameter 2533 in FIG. 24F, in some examples, the rotational movement information from at least two of three acceleration sensing elements (e.g. 122A/Y, 162/Z, 164/X) may be combined to produce composite rotational movement information (252), such as previously described in association with at least FIG. 5. In some instances, the rotational movement information from the combined acceleration sensing signals may sometimes be referred to as a virtual vector, e.g. a virtual rotational movement vector. Via such examples, at least two of the three orthogonally-arranged sensing elements may be used to perform determination of the respiration information at least based on an AC component of a multi-dimensional acceleration vector produced by the orthogonally-arranged, single-axis sensing elements.

In some examples, the sensing portion 2510 in FIG. 24F may comprise a posture parameter 2547 to direct sensing, received sensed information, etc. regarding posture, which also may comprise sensing of body position, activity, etc. of the patient. Among other uses, in one example implementation, the posture information may support posture parameter 2422 in confidence factor portion 2400 in FIG. 24B and/or in application of confidence factors at 2330 of example method in FIG. 24A.

This sensed posture information may be indicative of respiration information in some instances. However, in some example methods and/or devices, via sensing portion 2510, respiration information may be determined without using posture information or body position information. Instead, respiration information may be determined by sensing a change in value of the inclination angle of one or more acceleration sensing elements as the sensing elements move in synchrony with the rotational movements of the chest during breathing, as described throughout examples of the present disclosure. This sensing of rotational movement does not depend on, or involve, determining a posture of the patient.

Nevertheless, as described elsewhere herein, in some examples posture may be considered as one of several parameters when determining respiration information. For instance, sensing an upright posture typically is associated with a wakeful state, such as standing or walking. However, as noted elsewhere, a person could be in an upright sitting position (FIG. 7) and still be in a sleep state (e.g. sleeping a chair). Conversely, sensing a supine or lateral decubitus (i.e. laying on a side) posture typically is considered a sleeping body position or posture. However, a patient might be in such a position without being asleep. Accordingly, posture may be just one parameter used in determining respiration information when in a sleeping body position during a treatment period. Moreover, sensing posture may not be limited to sensing a static posture but extend to sensing simple changes in posture (or body position), which may be indicative of a sleep state/sleep stage at least because certain changes in posture (e.g. from supine to upright) are mostly likely indicative of a wake state. Similarly, more complex or frequent changes in posture and/or body position may be further indicative of a wake state, whereas maintaining a single stable posture for an extended period time may be indicative of a sleep state.

Among other types and/or ways of sensing information, via the accelerometer portion 2530 in FIG. 24F, the accelerometer sensor(s) described herein (and/or other accelerometers) may be employed to sense or obtain ballistocardiograph (BCG) sensing 2534, seismocardiograph (SCG) sensing 2536, and/or accelerocardiograph (ACG) sensing 2538. This sensed information may be used to at least partially determine or confirm respiration information, with such sensed information including heart rate and/or heart rate variability. Among other implementations, such heart rate and/or heart rate variability information may be used as part of implementing heart rate parameter 2424 in confidence factor portion 2400 in FIG. 24B and/or at confidence portion 2330 in FIG. 24A.

In some examples, the sensing portion 2510 may comprise an impedance sensing parameter 2550, which may direct sensing of and/or received sensed information regarding transthoracic impedance or other bioimpedance of the patient. In some examples, the impedance sensor 2550 may use a plurality of sensing elements (e.g. electrodes) spaced apart from each other across a portion of the patient's body, such as electrodes 2120, 2130, 2112, surface of device 2133, etc. in FIG. 23B. In some such examples, one of the sensing elements may be mounted on or form part of an external surface (e.g. case) of an implantable pulse generator (IPG) or other implantable sensing monitor, which other sensing elements (e.g. electrodes 2120, 2130 in FIG. 23B) may be located at a spaced distance from the sensing element of the IPG or sensing monitor. In at least some such examples, the impedance sensing arrangement integrates all the motion/change of the body (e.g. such as respiratory effort, cardiac motion, etc.) between the sense electrodes (including the case of the IPG when present). Some examples implementations of the impedance measurement circuit will include separate drive and measure electrodes to control for electrode to tissue access impedance at the driving nodes.

In some examples, the sensing portion 2510 may comprise a pressure sensing parameter 2552, which senses respiratory information, such as but not limited to respiratory cyclical information. In some such examples, the respiratory pressure sensor may comprise at least some of substantially the same features and attributes as described in Ni et al., US2011/0152706, METHOD AND APPARATUS FOR SENSING RESPIRATORY PRESSURE IN AN IMPLANTABLE STIMULATION SYSTEM, published US2011/0152706 on Jun. 23, 2011, and which is incorporated herein by reference in its entirety. In some examples, the pressure sensor 2552 may be located in direct or indirect continuity with respiratory organs or tissue supporting the respiratory organs in order to sense respiratory information. In some examples, one of the sensors 2120, 2130, etc. in FIG. 23B may comprise a pressure sensor.

In some examples, sensing portion 2510 may comprise an acoustic sensing parameter 2554 to direct sensing of, and/or receive sensed acoustic information, such as but not limited to cardiac information (including heart sounds), respiratory information, snoring, etc.

In some examples, the sensing portion 2510 of care engine 2500 (FIG. 24F) comprises other parameter 2548 to direct sensing of, and/or receive, track, evaluate, etc. sensed information other than the previously described information sensed via the sensing portion 2510.

In some examples, one sensing modality within sensing portion 2510 may be implemented via another sensing modality within sensing portion 2510.

In some examples, sensing portion 2510 of care engine 2500 may comprise a history parameter 2562 by which a history of sensed physiologic information is maintained, and which may be used via comparison parameter 2564 to compare recent sensed physiologic information with older sensed physiologic information.

As shown in FIG. 24F, in some examples, care engine 2500 may comprise a respiration portion 2580. In at least some examples, in general terms respiration portion 2580 may direct determining respiration information, including sensing of, and/or receiving, tracking, and/or evaluating respiratory morphology, including phase information, general patterns and/or specific fiducials within a respiratory signal. In some examples, the respiration portion 2580 may operate in cooperation with, or as part of sensing portion 2510 in FIG. 24F, which particularly includes (among other things) obtaining or sensing acceleration signal information to sense rotational movement of a patient's chest. Accordingly, in some examples the respiration portion 2580 comprises a feature extraction portion 2581 to determine respiratory morphology (including phase information) from the sensed acceleration signals regarding rotational movement of the chest wall. In some examples, the feature extraction portion 2581 may be implemented via at least some of the features and attributes as the previously described examples in FIGS. 24A-24D. With this in mind, as further shown in FIG. 24F, at least some aspects of such respiratory morphology determined, monitored, received, etc. via respiration portion 2580 may comprise inspiration phase morphology (parameter 2582), expiration active phase morphology (parameter 2583), and/or expiratory pause phase morphology (parameter 2584). In some examples, the respective inspiration morphology parameter 2582, expiratory active morphology parameter 2584, and/or expiratory pause morphology may comprise amplitude, duration, peak (2586), onset (2588), and/or offset (2590) of the respective inspiratory and/or expiratory phases of the patient's respiratory cycle. With this in mind, in some examples determining the respiratory morphology comprises identifying within the respiratory morphology a respiratory period, which includes the inspiratory phase, the expiratory active phase, and the expiratory pause phase. Accordingly, the respiratory period corresponds to a duration of a respiratory cycle, with this duration comprising a sum of a duration of the inspiratory phase, a duration of the expiratory active phase, and a duration of the expiratory pause phase. In some examples, the detected respiration morphology may comprise transition morphology (2592) such as an inspiration-to-expiration transition and/or an expiration-to-inspiration transition.

In some examples, the detected respiration morphology comprises detection (within the respiratory waveform morphology) of a start of the inspiratory phase, i.e. onset of inspiration. In some examples, this start of the inspiratory phase also may correspond to an expiration-to-inspiration transition. In some examples, a method of detecting the start of the inspiratory phase within the detected respiratory waveform morphology further comprises performing the detection without identifying an end (e.g. offset) of the inspiratory phase, which may enhance the accuracy of identification (of the start of the inspiratory phase) in the presence of noise, in contrast to identification of more than one phase transition (e.g. inspiratory-to-expiratory or expiratory-to-inspiratory) per respiratory cycle where each transition may be subject to mis-identification due to noise. In some examples, the end (e.g. offset) of the inspiratory phase corresponds to a start (e.g. onset) of the expiratory active phase.

In some examples, the respiration portion 2580 may identify (within the respiratory waveform morphology) a respiratory peak pressure, which predictably occurs a short interval after the end of inspiration and which may be used in aspects of respiration detection and related parameters. In one aspect, this arrangement may enhance the accuracy of identification (of an inspiratory-to-expiratory transition, end of inspiration, etc.) in the presence of noise due to the ease of identification of the relatively high mathematical derivative of the pressure signal associated with the interval following the end of inspiration.

In some examples, the respiration portion 2580 may identify (within the respiratory waveform morphology) an end of expiration, which may be used in some aspects of respiration detection and related parameters.

In some examples, as further shown in FIG. 24F, the respiration portion 2580 may comprise a confidence parameter 2585 to apply a selectable confidence factor (e.g. level) to different aspects of a filtered, sensed acceleration signal in order to determine the specific respiratory phase information (e.g. inspiration, expiratory active, expiratory pause). In some examples, the confidence parameter 2585 may be implemented, at least in part, via the confidence factor portion 2400 in FIG. 24B and/or as at 2330 in FIG. 24A.

In some examples, as further shown in FIG. 24F, the respiration portion 2580 may comprise a default parameter 2586 to use default respiratory phase information in place of a sensed acceleration signal when the sensed signal quality is poor. In some examples, the default parameter 2586 may be implemented, at least in part, via the default respiratory phase portion 2390 in FIG. 24A.

In some examples, as further shown in FIG. 24F, the respiration portion 2580 may comprise a slope inversion parameter 2594 to enhance tracking of the phases (e.g. inspiratory, etc.) of the determined respiration information regardless of whether the signal may be inverted relative to a default positive slope, as previously described in various examples of the present disclosure such that the respiration information may be reliably determined regardless of the patient's rotation in space and/or relative to the gravity vector (in at least some examples). In this regard, it will be noted that the determination of and/or use of the respiration information does not depend on which polarity the signal exhibits, but rather depends, at least partially, on the morphology of the respective phases (e.g. inspiratory, expiratory active, expiratory pause).

In some examples, as shown in FIG. 24F, the respiration portion 2580 may comprise a noise parameter 2596 by which noise is filtered or extracted from the acceleration signal to increase the signal-to-noise ratio for the rotational movement information. In some such examples, the noise parameter 2596 may be implemented via use of a noise model, such as but not limited to the example noise model parameter 2470 in FIG. 24E. In some such examples, the noise parameter 2596 may be implemented in association with at least some aspects of the feature extraction, as previously described in association with at least FIGS. 24A and 24C.

As further shown in FIG. 24F, in some examples the care engine 2500 comprises a SDB parameters portion 2800 to direct sensing of, and/or receive, track, evaluate, etc. parameters particularly associated with sleep disordered breathing (SDB) care. For instance, in some examples, the SDB parameters portion 2800 may comprise a sleep quality portion 2810 to sense and/or track sleep quality of the patient in particular relation to the sleep disordered breathing behavior of the patient. Accordingly, in some examples the sleep quality portion 2810 comprises an arousals parameter 2812 to sense and/or track arousals caused by sleep disordered breathing (SDB) events with the number, frequency, duration, etc. of such arousals being indicative of sleep quality (or lack thereof).

In some examples, the sleep quality portion 2810 comprises a state parameter 2814 to sense and/or track the occurrence of various sleep states (including sleep stages) of a patient during a treatment period or over a longer period of time.

In some examples, the SDB parameters portion 2800 comprises an AHI parameter 2830 to sense and/or track apnea-hypopnea index (AHI) information, which may be indicative of the patient's sleep quality. In some examples, the AHI information is obtained via a sensing element, such as one or more of the various sensing types, modalities, etc., which may be implemented as described in various examples of the present disclosure.

As further shown in FIG. 24F, in some examples care engine 2500 comprises a stimulation portion 2900 to control stimulation of target tissues, such as but not limited to an upper airway patency nerve (e.g. hypoglossal nerve) and/or a phrenic nerve, to treat sleep disordered breathing (SDB) behavior. In some examples, the stimulation portion 2900 comprises a closed loop parameter 2910 to deliver stimulation therapy in a closed loop manner such that the delivered stimulation is in response to and/or based on sensed patient physiologic information.

In some examples, the closed loop parameter 2910 may be implemented using the sensed information to control the particular timing of the stimulation according to respiratory information, in which the stimulation pulses are triggered by or synchronized with specific portions (e.g. inspiratory phase) of the patient's respiratory cycle(s). In some such examples and as previously described, this respiratory information may be determined via the sensors, sensing elements, devices, sensing portions (e.g. 2510) as previously described in association with at least FIGS. 1-24F.

In some examples in which the sensed physiologic information enables determining at least respiratory phase information, the closed loop parameter 2910 may be implemented to initiate, maintain, pause, adjust, and/or terminate stimulation therapy based on (at least) the determined respiratory phase information (2390).

In some examples, the stimulation is started prior to an onset of the inspiratory phase (2352 in FIG. 24A) and the stimulation is stopped exactly at the end of the inspiratory phase or stopped just after the end of the inspiratory phase.

As further shown in FIG. 24F, in some examples the stimulation portion 2900 comprises an open loop parameter 2925 by which stimulation therapy is applied without a feedback loop of sensed physiologic information. In some such examples, in an open loop mode the stimulation therapy is applied during a treatment period without (e.g. independent of) information sensed regarding the patient's sleep quality, sleep state, respiratory phase, AHI, etc. In some such examples, in an open loop mode the stimulation therapy is applied during a treatment period without (i.e. independent of) particular knowledge of the patient's respiratory cycle information.

However, in some such examples, some sensory feedback may be utilized to determine, in general, whether the patient should receive stimulation based on a severity of sleep apnea behavior.

As further shown in FIG. 24F, in some examples the stimulation portion 2900 comprises an auto-titration parameter 2920 by which an intensity of stimulation therapy can be automatically titrated (i.e. adjusted) to be more intense (e.g. higher amplitude, greater frequency, and/or greater pulse width) or to be less intense within a treatment period.

In some such examples and as previously described, such auto-titration may be implemented based on sleep quality, which may be obtained via sensed physiologic information, in some examples. It will be understood that such examples may be employed with synchronizing stimulation to sensed respiratory information (i.e. closed loop stimulation) or may be employed without synchronizing stimulation to sensed respiratory information (i.e. open loop stimulation).

In some examples, at least some aspects of the auto-titration parameter 2920 may comprise, and/or may be implemented, via at least some of substantially the same features and attributes as described in Christopherson et al.

U.S. Pat. No. 8,938,299, SYSTEM FOR TREATING SLEEP DISORDERED BREATHING, issued Jan. 20, 2015, and which is hereby incorporated by reference in its entirety.

In some examples, as further shown in FIG. 25A, the stimulation portion 2900 of care engine 2500 may comprise an "off period" function 2930 by which a user or clinician may adjust the time that stimulation will remain off and which may be expressed as a percentage of the previous "on period." In some examples, the "off period" for stimulation coincides with the expiratory active phase 2354 (FIG. 24A). However, in some examples, once enabled by the user or clinician, the "off period" (i.e. no stimulation) setting is implemented regardless of detected phases (e.g. 2352, 2354, 2356 in FIG. 24A).

In some examples, as further shown in FIG. 25A, the stimulation portion 2900 of care engine 2500 may comprise a "maximum stimulation" function 2930 which may be used by a patient or clinician to adjust a maximum time for an "on period" of stimulation for a given stimulation cycle, after which an "off period" takes place. The "on period" may extend for a selectable, predetermined period of time. In some examples, the "on period" for stimulation coincides with the inspiratory phase 2352 (FIG. 24A). In some such examples, once enabled by the user or clinician, the "on period" of stimulation is implemented regardless of detected phases (e.g. 2352, 2354, 2356 in FIG. 24A).

FIG. 25A is a block diagram schematically representing an example control portion 4000. In some examples, control portion 4000 provides one example implementation of a control portion forming a part of, implementing, and/or generally managing sensors, sensing element, respiration determination elements, stimulation elements, power/control elements (e.g. pulse generator), elements, devices, user interfaces, instructions, information, engines, elements, functions, actions, and/or methods, as described throughout examples of the present disclosure in association with FIGS. 1-24 and 25B-52.

In some examples, control portion 4000 includes a controller 4002 and a memory 4010. In general terms, controller 4002 of control portion 4000 comprises at least one processor 4004 and associated memories. The controller 4002 is electrically couplable to, and in communication with, memory 4010 to generate control signals to direct operation of at least some of the sensors, sensing element, respiration determination elements, stimulation elements, power/control elements (e.g. pulse generators), devices, user interfaces, instructions, information, engines, elements, functions, actions, and/or methods, as described throughout examples of the present disclosure. In some examples, these generated control signals include, but are not limited to, employing instructions 4011 and/or information 4012 stored in memory 4010 to at least determining respiration information of a patient. Such determination of respiration information may comprise part of directing and managing treatment of sleep disordered breathing such as obstructive sleep apnea, hypopnea, and/or central sleep apnea. In some instances, the controller 4002 or control portion 4000 may sometimes be referred to as being programmed to perform the above-identified actions, functions, etc. such that the controller 4002, control portion 4000 and any associated processors may sometimes be referred to as being a special purpose computer, control portion, controller, or processor. In some examples, at least some of the stored instructions 4011 are implemented as, or may be referred to as, a care engine, a sensing engine, respiration determination engine, monitoring engine, and/or treatment engine. In some examples, at least some of the stored instructions 4011 and/or information 4012 may form at least part of, and/or, may be referred to as a care engine, sensing engine, respiration determination engine, monitoring engine, and/or treatment engine.

In response to or based upon commands received via a user interface (e.g. user interface 4040 in FIG. 26) and/or via machine readable instructions, controller 4002 generates control signals as described above in accordance with at least some of the examples of the present disclosure. In some examples, controller 4002 is embodied in a general purpose computing device while in some examples, controller 4002 is incorporated into or associated with at least some of the sensors, sensing element, respiration determination elements, stimulation elements, power/control elements (e.g. pulse generators), devices, user interfaces, instructions, information, engines, functions, actions, and/or method, etc. as described throughout examples of the present disclosure.

For purposes of this application, in reference to the controller 4002, the term "processor" shall mean a presently developed or future developed processor (or processing resources) that executes machine readable instructions contained in a memory. In some examples, execution of the machine readable instructions, such as those provided via memory 4010 of control portion 4000 cause the processor to perform the above-identified actions, such as operating controller 4002 to implement the sensing, monitoring, determining respiration information, stimulation, treatment, etc. as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium), as represented by memory 4010. In some examples, the machine readable instructions may comprise a sequence of instructions, a processor-executable machine learning model, or the like. In some examples, memory 4010 comprises a computer readable tangible medium providing non-volatile storage of the machine readable instructions executable by a process of controller 4002. In some examples, the computer readable tangible medium may sometimes be referred to as, and/or comprise at least a portion of, a computer program product. In other examples, hard wired circuitry may be used in place of or in combination with machine readable instructions to implement the functions described. For example, controller 4002 may be embodied as part of at least one application-specific integrated circuit (ASIC), at least one field-programmable gate array (FPGA), and/or the like. In at least some examples, the controller 4002 is not limited to any specific combination of hardware circuitry and machine readable instructions, nor limited to any particular source for the machine readable instructions executed by the controller 3002.

In some examples, control portion 4000 may be entirely implemented within or by a stand-alone device.

In some examples, the control portion 4000 may be partially implemented in one of the sensors, sensing element, respiration determination elements, monitoring devices, stimulation devices, apnea treatment devices (or portions thereof), etc. and partially implemented in a computing resource separate from, and independent of, the apnea treatment devices (or portions thereof) but in communication with the apnea treatment devices (or portions thereof). For instance, in some examples control portion 4000 may be implemented via a server accessible via the cloud and/or other network pathways. In some examples, the control portion 4000 may be distributed or apportioned among multiple devices or resources such as among a server, an apnea treatment device (or portion thereof), and/or a user interface.

In some examples, control portion 4000 includes, and/or is in communication with, a user interface 4040 as shown in FIG. 26.

FIG. 25B is a diagram schematically illustrating at least some example arrangements of a control portion 4020 by which the control portion 4000 (FIG. 25A) can be implemented, according to one example of the present disclosure. In some examples, control portion 4020 is entirely implemented within or by an IPG assembly 4025, which has at least some of substantially the same features and attributes as a pulse generator (e.g. power/control element) as previously described throughout the present disclosure. In some examples, control portion 4020 is entirely implemented within or by a remote control 4030 (e.g. a programmer) external to the patient's body, such as a patient control 4032 and/or a physician control 4034. In some examples, the control portion 4000 is partially implemented in the IPG assembly 4025 and partially implemented in the remote control 4030 (at least one of patient control 4032 and physician control 4034).

FIG. 26 is a block diagram schematically representing user interface 4040, according to one example of the present disclosure. In some examples, user interface 4040 forms part or and/or is accessible via a device external to the patient and by which the therapy system may be at least partially controlled and/or monitored. The external device which hosts user interface 4040 may be a patient remote (e.g. 4032 in FIG. 25B), a physician remote (e.g. 4034 in FIG. 25B) and/or a clinician portal. In some examples, user interface 4040 comprises a user interface or other display that provides for the simultaneous display, activation, and/or operation of at least some of the sensors, sensing element, respiration determination elements, stimulation elements, power/control elements (e.g. pulse generators), devices, user interfaces, instructions, information, engines, functions, actions, and/or method, etc., as described in association with FIGS. 1-52. In some examples, at least some portions or aspects of the user interface 4040 are provided via a graphical user interface (GUI), and may comprise a display 4044 and input 4042.

FIG. 27 is a block diagram 4300 which schematically represents some example implementations by which an implantable device (IMD) 4310 (e.g. implantable device 606, an implantable pulse generator 2133, implantable sensing monitor, and the like) may communicate wirelessly with external devices outside the patient. As shown in FIG. 27, in some examples, the IMD 4310 may communicate with at least one of patient app 4330 on a mobile device 4320, a patient remote control 4340, a clinician programmer 4350, and a patient management tool 4336. The patient management tool 4336 may be implemented via a cloud-based portal 4362, the patient app 4330, and/or the patient remote control 4340. Among other types of data, these communication arrangements enable the IMD 4310 to communicate, display, manage, etc. the respiration determination information as well as to allow for adjustment to the various elements, portions, etc. of the example devices and methods if and where needed.

FIGS. 28A-46 are a series of block diagrams and/or flow diagrams schematically representing various example methods. In some examples, the various methods in FIGS. 28A-46 may be implemented via at least some of the sensors, sensing element, respiration determination elements, stimulation elements, power/control elements (e.g. pulse generators), devices, user interfaces, instructions, information, engines, functions, actions, and/or methods, as previously described in association with FIGS. 1-27. In some examples, the various methods in FIGS. 28-46 may be implemented via elements other than those previously described in association with FIGS. 1-27.

In some examples, one or more of the example methods in FIGS. 28A-46 may be employed together in various combinations. In some examples, one or more of the example methods in FIGS. 28-46 may be employed as part of, and/or together with, the example methods and devices previously described in association with FIGS. 1-27.

As shown at 5000 in FIG. 28A, some example methods comprise implantably securing an acceleration sensor at a first portion of a respiratory body portion of a patient; and determining respiration information via sensing, via the acceleration sensor, rotational movement at the first portion of the respiratory body portion caused by breathing. In some examples, the respiratory body portion may comprise a chest (e.g. thorax), such as but not limited to, a chest wall, such as described in association with at least FIGS. 1-46. In some examples, the respiratory body portion may comprise an abdomen, such as but not limited to, an abdominal wall, such as described in association with at least FIGS. 47-52 and throughout examples of the present disclosure. It will be understood that the respiratory body portion is not necessarily limited to the chest and/or abdomen but in some examples may comprise any other body portion of a patient which exhibits rotational movement caused by breathing and from which sensing of respiration information may be obtained, such as but not limited to, respiration morphology.

As shown at 5020 in FIG. 28B, some example methods comprise implantably securing an acceleration sensor at a first portion of a chest wall of a patient; and determining respiration information via sensing, via the acceleration sensor, rotational movement at the first portion of the chest wall caused by breathing.

As shown at 5100 in FIG. 29, some example methods comprise sensing the rotational movement relative to an earth gravitational field (e.g. gravity vector G).

As shown at 5150 in FIG. 30, some example methods comprise sensing the rotational movement according to at least one of three independent orthogonal axes.

As shown at 5200 in FIG. 31, some example methods comprise combining sensed rotational movement from at least two of the three independent orthogonal axes. Via such combining, the example method may produce composite rotational information (e.g. FIG. 5) for determining respiration information. In some examples, such combining also may be implemented according to the previously described example methods to perform determination of the composite rotational movement and therefore respiration information at least based on an AC component of a multi-dimensional acceleration vector produced by the n single-axis sensing elements.

As shown at 5250 in FIG. 32, some example methods comprise tracking changes in a value of a first signal, for a first body position during a treatment period, of at least one measurement axis during at least one respiratory period.

As shown at 5300 in FIG. 33, some example methods comprise determining respiration information without separately identifying measurement information from the sensor regarding translational motion of the chest wall. Via this arrangement, in some example methods/devices, determining the respiration information per acceleration sensing (of the rotational movement at the portion of the chest wall)

according to a greatest range of angular orientations (or greatest range of values of the AC signal component) may be performed without directly considering translational motion in determining the respiration information. In some examples, a magnitude of an AC signal component corresponding to rotational movement (of a portion of the chest wall) may be substantially greater than a magnitude of an AC signal component corresponding to translation movement (of the portion of the chest wall). In some examples, at least in this context, the term "substantially greater than" comprises a difference which is 50 percent greater, 100 percent greater, 150 greater, and the like. In some examples, at least in this context, the term "substantially greater than" comprises at least one order of magnitude difference. Accordingly, in at least some such examples, even if some translation movement is sensed, the sensed rotational movement dominates the AC signal component when measuring the inclination angle of the acceleration sensor during rotational movement of the portion of the chest wall during breathing.

As shown at 5400 in FIG. 34, some example methods comprise sensing the rotational movement without calibrating the measured inclination angle regarding differences between an ideal reference orientation and an actual implant orientation.

As shown at 5450 in FIG. 35, some example methods comprise identifying the rotational movement as at least one of a pitch parameter, yaw parameter, and a roll parameter.

As shown at 5500 in FIG. 36, some example methods comprise selecting an implant location to maximize a magnitude of the sensed rotational movement during breathing. In some examples, the implant location, implant orientation, etc. may be selected to ensure a sufficiently high degree of the sensed rotational movement during breathing to accurately and/or reliably determine respiration information (e.g. respiration morphology) even if, and/or when, the sensed rotational movement may not be a maximum obtainable value.

As shown at 5550 in FIG. 37A, some example methods comprise determining respiration information, via the sensed rotational movement, while excluding at least one of cardiac noise, muscle noise, and measurement noise. In particular, a sensed acceleration signal is filtered to recover low-frequency respiration signal information while rejecting cardiac noise, measurement noise, and muscle noise. This filtering may employ linear filters, such as low pass filters, high pass filters, band pass filters, and/or may employ non-linear filters, such as median filters and Kalman filters.

As shown at 5555 in FIG. 37B, some example methods comprise increasing a signal-to-noise ratio of sensed respiratory information via building a noise model and subtracting the noise model from the sensed acceleration signal. In some examples, the noise model may comprise at least some of substantially the same features and attributes as the noise model previously described at 2470 in FIG. 24E, and which may be used (in some examples) as part of enhancing determination of respiration information in the example method (and/or arrangement) 2300 in FIG. 24A. As previously described, in some examples the noise model may be built via identifying characteristics (e.g. morphology, frequency content, etc.) within sensed acceleration signals of the patient which are caused by various types of activities, positions, environments, etc. which are unrelated to determining respiration information but which may otherwise affect a magnitude and/or direction of the sensed acceleration signal. Once built, the noise model may be subtracted from the sensed acceleration signals, thereby increasing a signal-to-noise ratio of the respiratory features (e.g. morphology) within the sensed acceleration signal(s).

As shown at 5600 in FIG. 38, some example methods comprise measuring the at least one acceleration signal as measuring an inclination angle of a first measurement axis aligned generally perpendicular to an earth gravity vector.

As shown at 5650 in FIG. 39, some example methods comprise performing the acceleration sensing of rotational movement without determining a body position occurring during (e.g. at the time of) the sensing of rotational movement.

As shown at 5700 in FIG. 40, some example methods comprise performing the sensing of rotational movement (of a portion of chest wall), during each of several different sleeping body positions, without determining each respective different sleeping body position at the time of sensing of the rotational movement.

As shown at 5750 in FIG. 41, some example methods comprise determining respiratory morphology, including respiratory phase information, based on a profile over time of the respective determined range of values.

As shown at 5800 in FIG. 42, some example methods comprise determining, from the sensed rotational movement, respiratory morphology comprising an inspiratory phase, an expiratory active phase, and an expiratory pause phase.

As shown at 5850 in FIG. 43, some example method comprise identifying a confidence factor for the determined inspiratory phase, an expiratory active phase, and an expiratory pause phase.

As shown at 5900 in FIG. 44, some example methods comprise further determining the confidence factor based on additional criteria comprising posture information, heart rate information and/or sleep state information.

As shown at 5950 in FIG. 45, some example methods comprise implementing extraction of the respective inspiratory phase, expiratory active phase, and expiratory pause phase via applying a selectable inspiratory threshold, selectable expiratory active phase threshold, and/or selectable expiratory pause phase threshold.

As shown at 6000 in FIG. 46, some example methods comprises arranging the acceleration sensor to include at least two orthogonal axes, each of which produces at least a portion of the respiration information from the sensed rotational movement depending on a first body position of the patient.

Examples described in association with at least FIGS. 47-52 address determining respiration information via sensing at a respiratory body portion other than the chest, such as but not limited to the abdomen. In some examples, such determination of respiration information may employ at least some of substantially the same features and attributes as previously described in association with FIGS. 1-46, except being applied in the context of the abdomen instead of the chest.

With this in mind, it be further understood that in some examples, sensing in both the chest region and the abdominal region may be performed to determine respiration information and/or to treat sleep disordered breathing. Sensing at the abdomen and sensing at the chest may be performed simultaneously, alternatively, or dependent on the particular physiologic conditions encountered, such as whether central sleep apnea is present, obstructive sleep apnea is present, or whether a multi-type sleep apnea (e.g. both aspects of central and obstructive sleep apnea) is present.

As shown at 7000 in FIG. 47, some example methods comprise implantably securing an acceleration sensor at a first portion of an abdomen of a patient; and determining respiration information via sensing, via the acceleration sensor, rotational movement at the first portion of the abdomen caused by breathing. In some such examples, the abdomen comprises an abdominal wall, which may comprise at least one of an anterior abdominal wall, a lateral abdominal wall, and a posterior abdominal wall, or combinations thereof. In some such examples, in addition to acceleration sensing, at least some of the forms of sensing as previously described in association with at least sensing portion 2510 in FIG. 24F may be used to determine respiration information.

FIG. 48 is a diagram 7120, including a side view, schematically representing an example method and/or example sensor 104A. As shown in FIG. 48, in some examples the sensor 104A may comprise a sensing element 122A, which is arranged to measure an inclination angle ($\Omega$) upon rotational movement of the sensing element 122A caused by breathing. In some examples, the method and/or example sensor 104A in FIG. 48 may comprise at least some of substantially the same features and attributes as the example method and/or example sensor 104A as previously described in association with at least FIG. 2, except for being implantably secured at the abdomen to sense rotational movement at the abdomen which is indicative of respiratory information.

The sensor 104A, may be secured on top of, or to, muscle layer(s) of the abdominal wall, while in some examples, sensor 104A may be secured subcutaneously without being secured on top of the muscle layer(s) of abdominal wall or without secure to the muscle layer(s) of abdominal wall. In some such examples, the sensor 104A may be secured to non-bony anatomy at the abdomen.

As represented in FIG. 48, upon rotational movement of at least a portion of the abdominal wall 7102A during breathing, the sensing element 122A may rotationally move between a first angular orientation YR1 (shown in solid lines) and a second angular orientation YR2 (shown in dashed lines). In some such examples, the first angular orientation YR1 (shown in solid lines) of sensing element 122A may correspond to a peak expiration of a respiratory cycle (e.g. abdominal wall in collapsed state) and the second angular orientation YR2 (shown in dashed lines) of sensing element 122A may correspond to a peak inspiration of the respiratory cycle (e.g. abdominal wall in expanded state). In a manner similar to that previously described in association with at least FIGS. 1-3, it will be understood that sensing element 122A moves through a range of angular orientations (between at least the first angular orientation YR1 and second angular orientation YR2) and that the respective first and second angular orientations YR1, YR2 generally represent ends of the range and are not fixed positions.

With reference to at least FIG. 48, it will understood that the sensing element 122A moves with at least a portion of the abdominal wall 102A as depicted in dashed lines. Accordingly, sensing element 122A does not move relative to the abdominal wall 102A, but rather the sensing element 122A rotationally moves along with (e.g. in synchrony with) the rotational movement of at least the portion of the abdominal wall 7102A (in which the sensor 104A, including sensing element 122A), is implanted) during breathing. As represented in dashed lines 7410 in FIG. 48, the sensor 404 may comprise a sensing element 122A (Y-axis), a sensing element 162 (Z-axis), and/or a sensing element 164 (X-axis) having at least some of the features and attributes, as previously described in association with at least FIGS. 1-46.

It will be further understood that the example methods and/or example devices described in FIGS. 47-48 may be implemented, at least in part, according to any one or all of the various examples described in association with FIGS. 1-46, except for the method and/or device in FIGS. 47-48 being applied to sense respiration information via rotational movement of the abdomen caused by breathing instead of via rotational movement of the chest caused by breathing. Accordingly, in some examples, the sensing element 122A comprises an accelerometer, which may comprise a single axis accelerometer in some examples or which may comprise a multiple-axis accelerometer in some examples. Via the accelerometer, the sensing element 122A can determine absolute rotation of sensor 104A (and therefore rotation of the portion of the abdominal wall 7102A) with respect to gravity (e.g. earth gravity vector G), rather than instantaneous changes in rotation. In some examples, element 122A may comprise a single axis accelerometer to measure (at least) a value of, and changes in the value of, the above-noted inclination angle ($\Omega$) associated with movement of at least a portion the abdominal wall 102 caused by breathing. It will be understood that the use of sensing element 122A may comprise at least some of substantially the same features and attributes of sensing and determining respiration information (such as via sensing rotational movement) as described in association with at least FIGS. 3-46.

Figure 49:
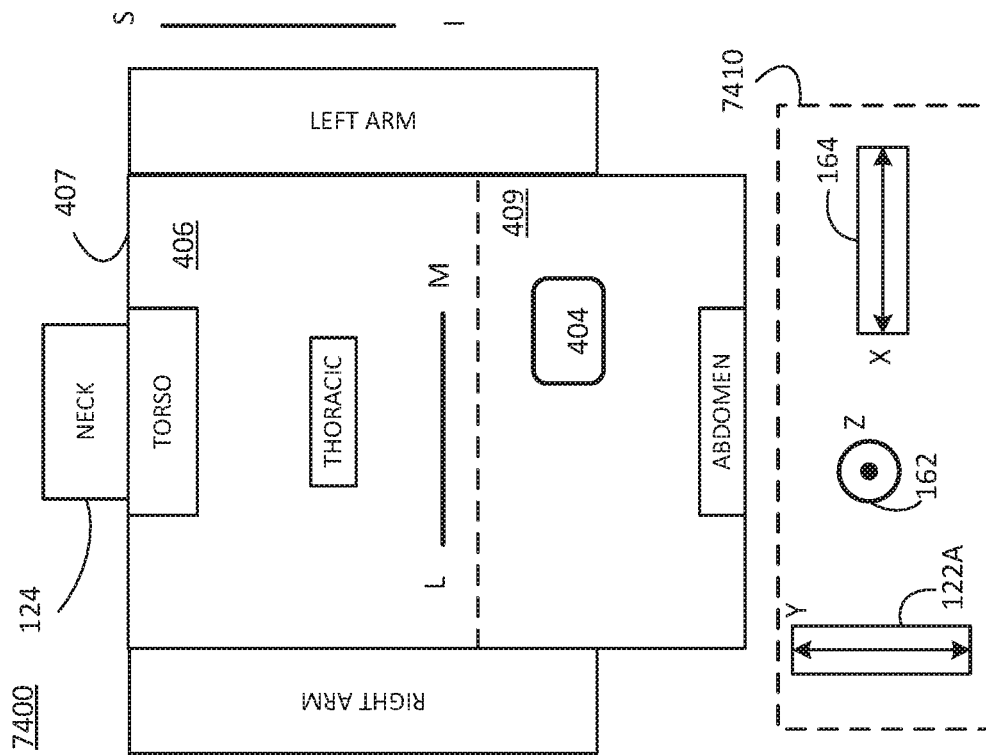
FIG. 49 is a diagram, including a front view, schematically representing an example method and/or example device for detecting respiration via multiple sensing elements of an acceleration sensor at an abdominal wall.

In some examples, as shown in FIG. 49, a sensor 404 (such as in FIG. 8) may be implanted in the abdomen 409 to sense rotational movement at the abdomen to determine respiration information in a manner similar to that previously described in association with at least FIGS. 1-46 (except for the abdomen instead of the chest).

In some examples, the respiration information sensed at the abdomen 409 may be used in an example method to stimulate a breathing-related nerve, such as an upper-airway-patency-related nerve (e.g. hypoglossal nerve) to treat obstructive sleep apnea, to stimulate a phrenic nerve to treat central sleep apnea, or to stimulate both such nerves to treat multiple-type sleep apnea.

Figure 50:
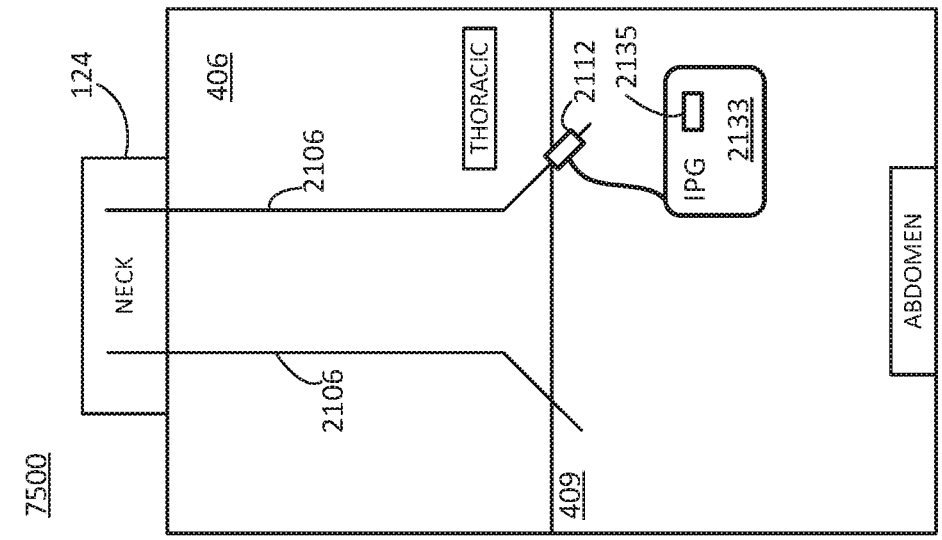
FIG. 50 is a diagram, including a front view, schematically representing an example method and/or example device for treating sleep disordered breathing via a medical device implanted at an abdomen to stimulate a phrenic nerve in the abdomen and including an acceleration sensor.

Accordingly, as shown in FIG. 50, in some examples, an acceleration sensor (e.g. 404 in FIG. 49) may be supported by or otherwise associated with an implantable pulse generator (IPG) 2133 (FIGS. 23A-23B) subcutaneously implanted in the abdomen 409. The sensor 404 may be implemented as an accelerometer 2135, as previously described in association with at least FIGS. 23A-23B. Accordingly, via the accelerometer 2135, example methods and/or devices may determine respiration information. In some example methods and/or devices, a stimulation electrode 2112 is implantable in the abdomen 409 and supported by the IPG 2133 to be coupled in some manner relative to the phrenic nerve to stimulate the phrenic nerve 2106, such as at an abdominal location. The stimulation electrode 2112 may be a cuff electrode, a paddle electrode, a transvenously deliverable electrode, etc. In some such examples, the stimulation electrode(s) may comprise the sole stimulation elements of the example methods/devices, such that no stimulation electrode is provided to stimulate an upper-airway-patency-related nerve. The example methods and/or devices for such acceleration sensing and/or stimulation in association with FIG. 50 may comprise at least some of substantially the same features and attributes as previously described in association with at least FIGS. 1-46. In some examples in which the acceleration sensor is implanted within the abdominal region to determine respiration information, other sensing modalities may be implanted in the abdominal region as well and/or may be implanted elsewhere, such as in the head-and-neck region and/or in the thoracic region (e.g. pectoral region) as previously described in association with at least FIGS. 1-46. For instance, some example methods and/or devices may employ an abdominally-implanted acceleration sensor (to at least partially determine respiration information) and cardiac-related sensors (e.g. impedance, ECG, etc.) in the thoracic region 406.

Figure 51:
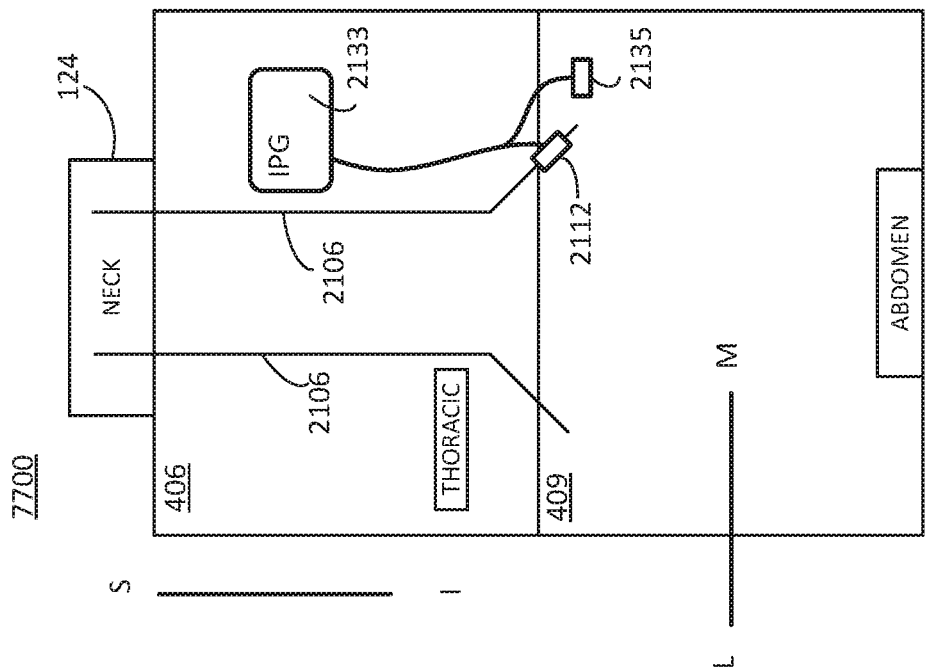
FIG. 51 is a diagram, including a front view, schematically representing an example method and/or example device for treating sleep disordered breathing via a medical device implanted in a pectoral region to stimulate a phrenic nerve in the abdomen and an acceleration sensor implanted in the abdomen.

As shown in FIG. 51, in some examples an acceleration sensor (e.g. accelerometer 2135 or single acceleration sensing element) may be implanted in the abdominal region 409 and a stimulation electrode 2112 may be implanted to be coupled to the phrenic nerve 2106 to stimulate the phrenic nerve. This example may comprise at least some of substantially the same features and attributes as in FIG. 50, except with IPG 2133 being implanted in a thoracic region such as the pectoral region with a single lead 7710 extending from the IPG 2133 to support the accelerometer 2135 and the stimulation electrode 2112.

As shown in FIG. 52, in some examples an acceleration sensor (e.g. accelerometer 2135) may be implanted in a thoracic (e.g. pectoral region) and a stimulation electrode 2112 may be coupled relative to a phrenic nerve 216 in a head-and-neck region 124 or a thoracic region of the patient's body.

In some examples, both a pulse generator 2133 and associated stimulation electrode 2112 for stimulating the phrenic nerve 2106 may be located in a head-and-neck region, such as when the pulse generator 2133 and stimulation electrode 2112 together take the form of a microstimulator. In some such examples, one stimulation electrode may be implanted in a head-and-neck region to stimulate an upper-airway-patency-related nerve (e.g. hypoglossal nerve) and another separate stimulation electrode may be implanted in the head-and-neck region to stimulate the phrenic nerve. In some such examples, both nerves may be stimulated (although not necessarily simultaneously) in a method of treating multi-type sleep apnea.

Figure 53:
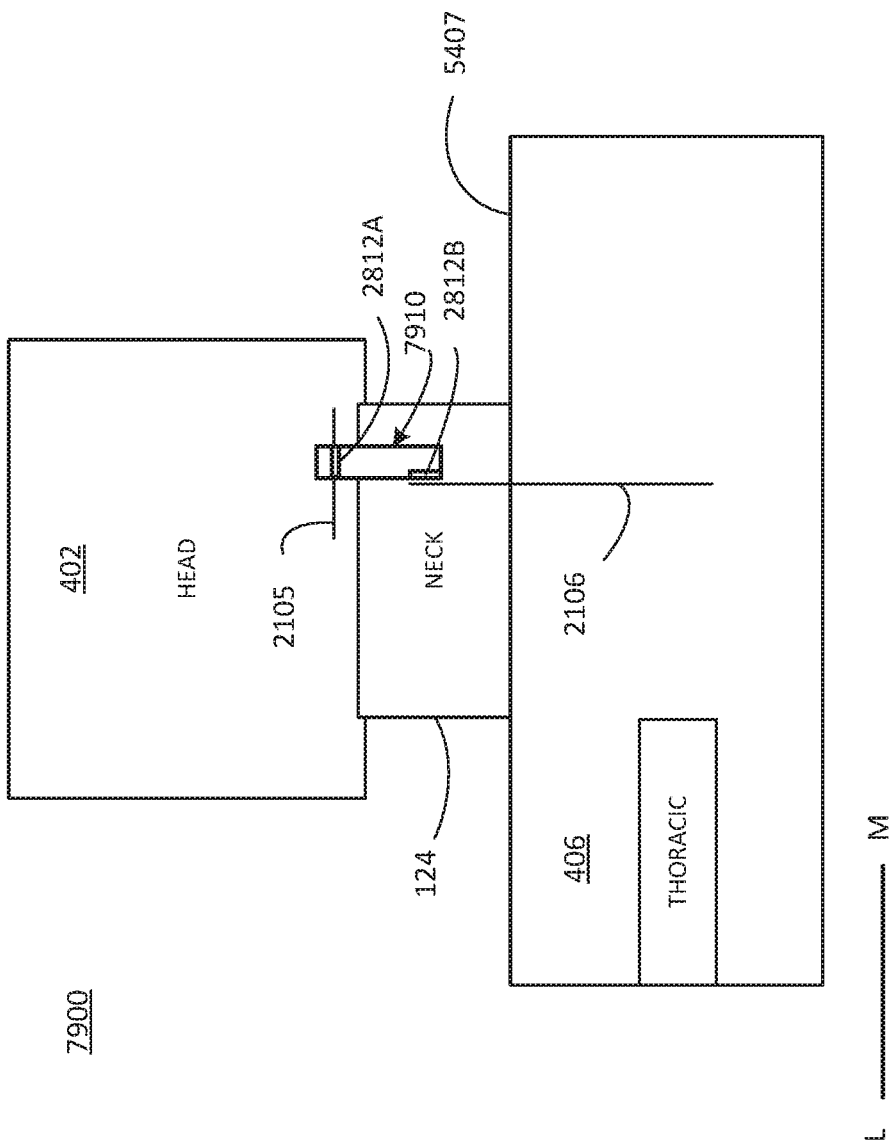
FIG. 53 is a diagram, including a front view, schematically representing an example method and/or example device for treating sleep disordered breathing via a microstimulator implanted in a head-and-neck region to stimulate a phrenic nerve in the head-and-neck region.

As shown in FIG. 53, in some example devices 7900 (and/or example methods), both a pulse generator 2833 and associated stimulation electrode 2812 for stimulating the phrenic nerve 2106 may be located in a head-and-neck region, such as when the pulse generator 2833 and stimulation electrode 2812 together take the form of a microstimulator 7910. In some such examples, one stimulation electrode 2812A of the microstimulator 7910 may be implanted in a head-and-neck region to stimulate an upper-airway-patency-related nerve 2105 (e.g. hypoglossal nerve) and another separate stimulation electrode 2812B of the microstimulator 7910 may be implanted in the head-and-neck region to stimulate the phrenic nerve 2106. In some such examples, both nerves may be stimulated (although not necessarily simultaneously) in a method of treating multi-type sleep apnea. In some examples, the microstimulator 7910 in FIG. 53 may comprise at least some of substantially the same features and attributes as the microstimulator 2260 previously described in association with at least FIG. 23C.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. A method comprising:
    implantably securing a device comprising an acceleration sensor at a respiratory body portion of a patient;
    arranging the acceleration sensor as a plurality of orthogonally-arranged, single-axis acceleration sensing elements;
    determining respiration information via sensing, via the acceleration sensor, rotational movement associated with the respiratory body portion caused by breathing, wherein determining the respiration information comprises determining respiratory waveform morphology;
    identifying via a control portion of the device, during breathing, which respective acceleration sensing element exhibits a greatest range of values for an AC signal component;
    performing the determination of respiration information, via the sensed rotational movement, using only the identified acceleration sensing element determined to exhibit the greatest range of values of the AC signal component; and
    delivering electrical stimulation, via an implantable electrode, to a breathing-related nerve based on the determined respiratory waveform morphology, and wherein the breathing-related nerve comprises at least one of an upper airway patency-related nerve and a phrenic nerve.

2. The method of claim 1, wherein the respiratory body portion comprises at least one of a chest wall and an abdominal wall.

3. The method of claim 1, wherein the securing at the respiratory body portion comprises mechanically coupling the acceleration sensor relative to the respiratory body portion.

4. The method of claim 1, comprising:
    sensing the rotational movement via the acceleration sensor relative to an earth gravity vector.

5. The method of claim 4, comprising
    performing the sensing during a first sleeping body position within a treatment period without determining the first sleeping body position via the sensing.

6. The method of claim 4, wherein the sensing comprises:
    sensing the rotational movement independently in three orthogonal axes.

7. The method of claim 1, comprising:
    performing the determination of respiratory waveform morphology without employing an absolute magnitude of an AC signal component from the acceleration sensor.

8. The method of claim 1, wherein determining the respiratory waveform morphology comprises identifying, within the respiratory waveform morphology, an inspiratory phase.

9. The method of claim 8, comprising:
    determining a confidence factor associated with at least one of the identified inspiratory phase and the sensor signal.

10. The method of claim 8, comprising:
    predicting an onset of the inspiratory phase at least partially based on at least one of:
        historical inspiratory phase information and/or historical respiratory rate information;
        immediately preceding expiratory active phase information; and
        immediately preceding expiratory pause phase information.

11. The method of claim 1, comprising:
    substituting, upon the acceleration sensor obtaining an inadequate signal, stored respiratory information comprising historical respiration information for at least one of:

the patient's respiratory cycle information; and
multiple-patient respiratory cycle information.

12. The method of claim 1, comprising:
substituting, upon the acceleration sensor obtaining an inadequate signal, stored respiratory information comprising respiratory cycle information including at least one of:
  a first respiratory rate substantially faster than the patient's average respiratory rate; and
  a second respiratory rate substantially slower than the patient's average respiratory rate.

13. A method comprising:
implantably securing a device comprising an acceleration sensor at a respiratory body portion of a patient;
determining respiration information via sensing, via the acceleration sensor, rotational movement associated with the respiratory body portion caused by breathing;
wherein determining the respiration information comprises determining, via a control portion of the device, respiratory waveform morphology;
wherein determining the respiratory waveform morphology comprises identifying, within the respiratory waveform morphology, an inspiratory phase;
wherein determining the respiration information via sensing the rotational movement comprises:
  identifying the inspiratory phase regardless of a positive slope or a negative slope of the inspiratory phase of the respiratory waveform; and
delivering electrical stimulation, via an implantable electrode, to a breathing-related nerve based on the determined respiratory waveform morphology, and wherein breathing-related nerve comprises at least one of an upper airway patency-related nerve and a phrenic nerve.

14. The method of claim 13, comprising:
synchronizing the delivery of electrical stimulation relative to a first portion of the respiratory waveform morphology.

15. A method comprising:
implantably securing a device comprising an acceleration sensor at a respiratory body portion of a patient;
determining respiration information via sensing, via the acceleration sensor, rotational movement associated with the respiratory body portion caused by breathing;
wherein determining the respiration information comprises determining, via a control portion of the device, respiratory waveform morphology;
wherein determining the respiratory waveform morphology comprises identifying, within the respiratory waveform morphology, an inspiratory phase;
determining, via the control portion, a confidence factor associated with at least one of the identified inspiratory phase and the sensor signal; and
wherein determining the confidence factor associated with the sensor signal comprises:
  determining the confidence factor for each respective signal component of three orthogonal measurement axes of the acceleration sensor,
synchronizing a delivery of electrical stimulation relative to a first portion of the respiratory waveform morphology.

* * * * *